US007332168B2

(12) United States Patent
Zocher et al.

(10) Patent No.: US 7,332,168 B2
(45) Date of Patent: Feb. 19, 2008

(54) COMPOSITION FOR THE ELIMINATION OF AUTOREACTIVE B-CELLS

(75) Inventors: Marcel Zocher, München-Germering (DE); Patrick Bäeuerle, Gauting (DE); Torsten Dreier, München (DE)

(73) Assignee: Micromet AG, Munich (DE)

( * ) Notice: Subject to any disclaimer, the term of this patent is extended or adjusted under 35 U.S.C. 154(b) by 483 days.

(21) Appl. No.: 10/362,591

(22) PCT Filed: Aug. 22, 2001

(86) PCT No.: PCT/EP01/09714

§ 371 (c)(1),
(2), (4) Date: May 12, 2003

(87) PCT Pub. No.: WO02/16414

PCT Pub. Date: Feb. 28, 2002

(65) Prior Publication Data

US 2004/0072749 A1      Apr. 15, 2004

(30) Foreign Application Priority Data

Aug. 22, 2000  (EP) .................................. 00117354

(51) Int. Cl.
*A61K 39/00* (2006.01)
*A61K 35/14* (2006.01)
*C07K 16/46* (2006.01)
*C07K 14/00* (2006.01)

(52) U.S. Cl. ................................ 424/192.1; 530/387.1
(58) Field of Classification Search ............. 424/192.1; 530/387.3
See application file for complete search history.

(56) References Cited

U.S. PATENT DOCUMENTS

| 5,614,611 | A |   | 3/1997  | Chang |   |
|---|---|---|---|---|---|
| 5,714,147 | A |   | 2/1998  | Capon et al. |   |
| 5,837,486 | A |   | 11/1998 | Bodary et al. |   |
| 5,932,448 | A |   | 8/1999  | Tso et al. |   |
| 6,056,952 | A | * | 5/2000  | Rosenberg .............. | 424/93.21 |
| 6,225,448 | B1 | * | 5/2001  | Tao et al. ............... | 530/387.3 |
| 6,569,431 | B2 | * | 5/2003  | von Budingen et al. . | 424/142.1 |

FOREIGN PATENT DOCUMENTS

| JP | 09 077800 A |   | 3/1997 |
|---|---|---|---|
| WO | WO 95/07096 | * | 3/1995 |
| WO | WO 95/24220 A |   | 9/1995 |
| WO | WO 96/34880 A1 |   | 11/1996 |
| WO | WO 98/33912 | * | 8/1998 |
| WO | WO 99/11667 A |   | 3/1999 |
| WO | WO 99/23867 A |   | 5/1999 |
| WO | WO 99/41363 A1 |   | 8/1999 |
| WO | WO 00/01732 A |   | 1/2000 |

OTHER PUBLICATIONS

Van Noort et al, International Reivew of Cytology 178: 127-205, 1998.*
Pedotti et al, Nature Immunology 2(3): 216-222, Mar. 2001.*
Wallace et al in Methods Enzymol 152: 432-439, 1987.*
Database WPI, Week 9722, Derwent Publications Ltd., London, GB; An 1997-241758, XP002196726, "*Phemphigus foliaceus* antigen-IgG constant region fusion protein—linked through the hinge region used to treat penphigus".
Proby et al., "Development of chimeric molecules for recognition and targeting of antigen-specific B cells in *Pemphigus vulgaris*," British Journal of Dermatology, vol. 142, No. 2, Feb. 2000, pp. 321-330, XP002196725, ISSN: 0007-0963.
Schroeder et al., "A recombiant bispecific single chain antibody CD19XCD3 induces rapid B cell lymphoma-directed cytotoxicity of unstimulated human T cells," BLOOD, vol. 92, No. 10, Nov. 15, 1998, p. 511A, XP002115457, ISSN: 0006-4971.
Stefferl et al., "Butyrophilin, a milk protein, modulates the encephalitogenic T cell response to myelin oligodendrocyte glycoprotein in experimental autoimmune encephalomyelitis," Journal of Immunology, vol. 165, No. 5, Sep. 1, 2000, pp. 2859-2865, XP002206101, ISSN: 0022-1767.
Khanna et al., "Antibodies in the sera of acute rheumatic fever patients bind to human cardiac tropomyosin," Journal of Autoimmunity, vol. 10, No. 1, Feb. 1997, pp. 99-106, XP002206102, ISSN: 0896-8411.
Lake et al., "Autoantibodies to the alpha/beta T-cell receptors in human immunodeficiency virus infection: dysregulation and mimicry," Proceedings of the National Academy of Science of the Untied States of America, vol. 91, No. 23, Nov. 8, 1994, pp. 10849-10853, XP002206103, ISN: 0027-8424.
Matsukura et al., "The Goodpasture antigen: common epitopes in the globular domains of collagen IV," NEPHRON, vol. 64, No. 4, 1993, pp. 532-539, XP001088498, ISSN: 0028-2766.
Balding et al., "Cicatricial pemphigoid autoantibodies react with multiple sites on the BP180 extracellular domain," The Journal of Investigative Dermatology, Jan. 1996, vol. 106, No. 1, Jan. 1996, pp. 141-146, XP001087971, ISSN: 022-202X.
Döpp et al., "IgG4 and IgE are the major immunoglobulins targeting the NC16A domain of BP180 in Bullous pemphigoid: serum levels of those immunoglobulins reflect disease activity," Journal of the American Academy of Dermatology, vol. 42, No. 4, Apr. 4, 2000, pp. 577-583, XP001087911, ISSN: 0190-9622.
Dominguez-Lopez et al., "Cellular immune response to *Klebsiella pneumoniae* antigens in patients with HLA-B27+ ankylosing spondylitis," Journal of Rheumatology, vol. 27, No. 6, Jun. 2000, pp. 1453-1460, XP001088217, ISSN: 0315-162X.

(Continued)

*Primary Examiner*—Christina Chan
*Assistant Examiner*—Phuong Huynh
(74) *Attorney, Agent, or Firm*—Foley & Lardner LLP

(57) ABSTRACT

The present invention relates to a composition for the selective elimination of autoreactive B-cells comprising at least one (poly)peptide construct consisting of at least two domains wherein one of said domains comprises an autoreactive antigen or (a) fragments(s) thereof specifically recognized by the Ig receptors of said autoreactive B-cells and wherein one of said domains comprises an effector molecule capable of interacting with and/or of activating NK-cells, T-cells, macrophages, monocytes and/or granulocytes and/ or capable of activating the complement system.

2 Claims, 25 Drawing Sheets

OTHER PUBLICATIONS

Obermayer-Straub et al., "Target proteins in human autoimmunity: cytochromes P450 and UDP-glucuronsyltransferases," Canadian Journal of Gastroenterology=Journal Canadien de Gastroenterologie, vol. 14, No. 5, May 2000, pp. 429-439, XP001088216, ISSN: 0835-7900.

Eystathioy et al., "Human autoantibodies to a novel Golgi protein golgin-67: High similarity with golgin-95/gm 130 autoantigen," Journal of Autoimmunity, vol. 14, No. 2, Mar. 2000, pp. 179-187, XP001088204, ISSN: 0896-8411.

Lock et al., "IgA anti-tissue transglutaminase as a diagnostic marker of gluten sensitive enteropathy," Journal of Clinical Pathology, vol. 52, No. 4, Apr. 1999, pp. 274-277, XP001087690, ISSN: 0021-9746.

Ebringer et al., "HLA molecules, bacteria and autoimmunity," Journal of Medical Microbiology, vol. 49, No. 4, Apr. 2000, pp. 305-311, XP001087834, ISSN: 022-2615.

Link et al., "Production and Characterization of a Bispecific IgG Capable of inducing T-Cell-Mediated Lysis of Malignant B Cells," BLOOD, vol. 81, No. 12, Jun. 1993, pp. 3343-3349, XP002900864, ISSN: 0006-4971.

* cited by examiner

A.

B.

A

B

A

B

A

B

A

B

A

B

Specific binding of MOG-Fc fusion protein to IgM+ B-cells derived from splenocytes from anti-MOG transgenic mice

A

IgM huFc

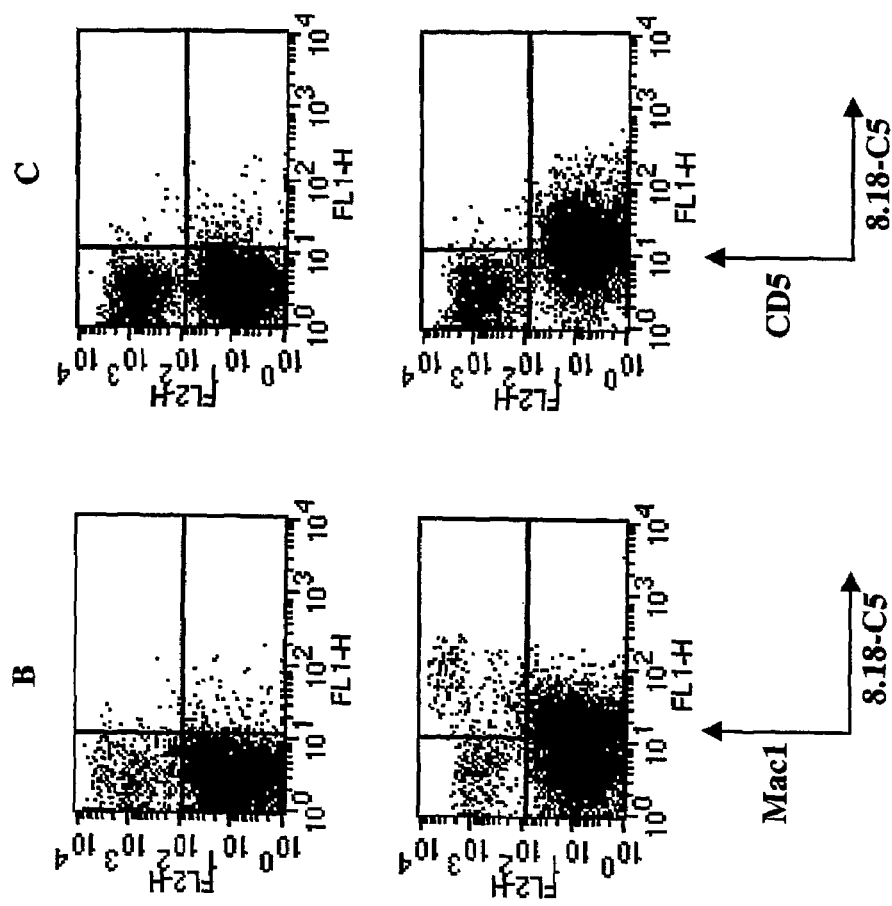
Fig. 14B, C
Selective binding of MOG-Fc fusion protein to wildtype murine splenocytes

COMPOSITION FOR THE ELIMINATION OF AUTOREACTIVE B-CELLS

CROSS REFERENCE TO RELATED APPLICATIONS

This application is a national phase application of PCT/EP01/09714 filed Aug. 22, 2001, which claims priority to EP 00 11 7354.1 filed Aug. 22, 2000, both of which are incorporated in their entirety by reference.

BACKGROUND OF THE INVENTION

1. Field of the Invention

The present invention relates to a composition for the selective elimination of autoreactive B-cells comprising at least one (poly)peptide construct consisting of at least two domains wherein one of said domains comprises an autoreactive antigen or (a) fragment(s) thereof specifically recognized by the Ig receptors of said autoreactive B-cells and wherein one of said domains comprises an effector molecule capable of interacting with and/or activating NK-cells, T-cells, macrophages, monocytes and/or granulocytes. Preferably, said composition comprises at least one (poly)peptide construct consisting of at least two domains, wherein said domain comprising an autoreactive antigen or (a) fragment thereof is MOG or (a) fragment(s) thereof and wherein said domain comprising an effector molecule is an anti-CD3 receptor or an Fc-part of an immunoglobulin. Described is also the use of the afore-mentioned (poly) peptide construct for the preparation of a pharmaceutical composition for the treatment and/or prevention of an autoimmune disease. In addition, the present invention relates to method for treating, ameliorating and/or preventing of an autoimmune disease.

2. Description of the Related Art

Several documents are cited throughout text of this specification. Each of the documents cited herein (including any manufacturer's specifications, instructions, etc.) are hereby incorporated by reference.

Autoimmunity results from the failure of the immune system in tolerating self-reactive lymphocytes, resulting in an adaptive immune response against self antigens. When such immune responses are sustained, they cause lasting tissue damage and are classified as autoimmune diseases.

Autoimmune diseases are generally divided into three types: B-cell dominant, T-cell dominant or combinational types. Pathogenic phenotypes of B-cell dominant autoimmune diseases are caused by circulating autoantibodies produced by autoreactive B-cells, while those of the T-cell dominant type are caused by direct tissue damage of activated T-cells against cells presenting autoreactive peptide-MHC complexes on their surface. Yet, these distinctions are not perspicuous, since B-cells and T-cells cooperate with and depend on each other in each type of autoimmune disease. Autoimmune diseases are classified as combinatorial when both autoreactive B- and T-cells contribute directly to the pathogenesis observed ("Immunobiology", $4^{th}$ edt. (1999), Chapter 13 pp 489-536, Janeway, C. A., Travers, P., Walport, M., Capra, J. D. eds and "Harrison's Principles in Internal Medicine", $14^{th}$ edt, Fauci, Braunwald, Isselbacher, Wilson, Martin, Kasper, Hauser, Longo, eds).

BRIEF SUMMARY OF INVENTION

The pathogenic effects of autoreactive B cells are caused by the secreted autoreactive antibodies. Antibody-mediated autoimmune diseases can be differentiated into two major groups based on their immunopathogenic mechanism. The first group comprises autoimmune responses against cell-surface or extracellular matrix antigens, while the second group consists of immune-complex diseases.

Examples of the first group of antibody-mediated autoimmune diseases are autoimmune hemolytic anemia, autoimmune thrombocytopenic purpura, myasthenia gravis, Goodpasture's syndrome, immunologically mediated blistering diseases like Pemphigus vulgaris and pemphigus foliaceus, and acute rheumatic fever. Examples of the second group comprise mixed essential cryoglobulinemia, subacute bacterial endocarditis, and several rheumatic autoimmune diseases.

Current treatment options for antibody-mediated autoimmune diseases include small molecule anti-inflammatory and immuno-suppressive agents, plasmapheresis, surgical treatments and/or cytokine administration.

For example, pemphigus vulgaris and pemphigus foliaceus are usually treated with glucocorticoids and, in some cases, also with immunosuppressive agents. Myasthenia gravis treatment options include anticholinesterase medications, immunosuppressive agents, thymectomy, plasmapheresis or intravenous unspecific immunoglobulin. Multiple sclerosis treatments include interferon beta, glucocorticoids, plasmapheresis.

Yet, current therapies for autoimmune diseases/disorders are not selective, treat essentially only symptoms and/or lead to broad immuno-suppression.

Experimental approaches to therapy include removal of the entire B cell compartment using monoclonal antibodies against pan-B cell surface antigens (CD19, CD20), or even pan-leucocyte antigens (CD52). Anti-CD52 monoclonal antibodies have been tested in clinical trials for their ability to ameliorate conditions of patients with multiple sclerosis. However, the indiscriminate elimination of B and T cells using anti-CD52 monoclonal antibody leads to a substantial release of pro-inflammatory cytokines, contributing to a progressive phase of disability (Coles (1999) Lancet 354, 1691-1695; Coles (1999) Ann. Neurol. 46, 296-304). Thus, highly selective removal of only the autoreactive B cells is needed to prevent the disasterous side effects. Other pan-B cell antibody based approaches include immuno-toxins (WO 96/36360). Recently, an approach combining an autoantigen with an immunotoxin has been tested in vitro. The construct was a desmoglein3 (dsg3)-toxin fusion protein for the treatment of experimental pemphigus vulgaris (Proby, Brit. J. Dermatol. (2000) 142, 321-330). This approach, however, lacks efficacy. In Proby (2000), a cytotoxic effect of the dsg3-PE toxin was determined in vitro at concentrations of 50 microgram/ml. Assuming a distribution in blood and lymph fluid (about 10 l volume total) and an average weight of 70 kg, such a concentration would correspond to a dose of about 5000 to 7000 micrograms/kg. In contrast, the maximal tolerated dose (MTD) in man for an anti-CD25scFv-PE toxin (LMB-2) compound was determined at 63 micrograms/kg. Side effects included elevated transaminase levels and cardiomyopathy (Kreitman, (2000) J. Clin. Oncol. 18, 1622-1636). Similar MTDs were determined for scFv-toxin LMB-1, an anti-LeY scFv-PE toxin compound (75 microgram/kg; Pai, (1996) Nat. Med. 2, 350-353). Thus, the doses theoretically required for specific activity by dsg3-PE toxin are about 100 times higher than the MTD determined for PE toxin compounds. It is conceivable that further harmful toxicity could result from binding of the autoantigen-toxin construct to anti-dsg3 autoantibodies. The complex could then be bound and internalized by any kind of FcR-bearing immune cells, killing thereby non-autoreactive immune cells and leading to a general immunosuppression.

In myasthenia gravis, approaches to downregulate autoimmune reactions using intact or portions of the acetylcholine receptor (AchR, Achr) has been the main goal of multiple studies in animal models. However, AChR is highly immunogenic and thus, frequent administrations of the molecule might lead to an immune response rather than tolerance induction. Therefore, short peptides that represent T cell epitopes of the AChR and especially altered T cell epitopes with less immunogenic potential than the native protein were tested in order to provide for an approach to therapy. In detail, dominant T cell epitope peptides of the Torpedo AChR were injected either before immunization with the Torpedo AChR or after priming suppressed disease manifestations. However, at least one of these studies reported lack of ability of the peptides to treat an ongoing disease in an animal model (Karachunski, (1999) *J. Neuroimmunol.* 93, 108-121).

Approaches to treat multiple sclerosis include treatments which affect the overall immune system, like treatment with anti-inflammatory agents, comprising azathioprine, cyclophosphamide, prednisone, corticosteroids, cyclosporin A, calcineurin, rapamycin, beta-interferon ("Harrison's Principles of Internal Medicine", $14^{th}$ edition, McGraw-Hill publisher, 2415-2419; Wang, J. Immunol. 165 (2000), 548-557). In addition, a number of non-specific treatments are administered that may improve the quality of life including physical therapy and psycho-pharmacological agents. Experimental approaches include peptide ligands to block T cell epitopes (Holz, J. Immunol. 164 (2000), 1103-1109; Krogsgaard, J. Exp. Med. 191 (2000), 1395-1412) and TNF alpha inhibitors (Klinkert, J. Neuroimmunol. 72 (1997), 163-168).

Autoreactive B cells occur at a very low frequency. For example, in a frequency of about $10^{-6}$ to $10^{-7}$ of total B cells circulating in the blood of individuals suffering from multiple sclerosis. This low frequency has been a major impediment in the isolation of such cells from patients. Elimination of autoreactive B cells in vivo can therefore only be monitored indirectly via the determination of autoreactive antibody titers and is further complicated by the long half-life of antibodies in serum. Direct in vitro testing of the proposed concept for the elimination of autoreactive B cells using human ex-vivo samples from patients suffering from B cell mediated autoimmune disease has not been possible due to the low abundance of these cells.

Therefore, the technical problem underlying the present invention was to develop and to provide for means and methods for preventing, treating and/or ameliorating antibody-mediated autoimmune diseases/disorders.

The solution to said technical problem is achieved by the embodiments characterized in the claims.

Accordingly, the present invention relates to a composition for the selective elimination of autoreactive B-cells comprising at least one (poly)peptide construct consisting of at least two domains wherein one of said domains comprises an autoreactive antigen or (a) fragment(s) thereof specifically recognized by the Ig receptors of said autoreactive B-cells and wherein one of said domains comprises an effector molecule capable of interacting with and/or of activating NK-cells, T-cells, macrophages, monocytes and/or granulocytes and/or capable of activating the complement system.

The present invention is based on the surprising finding that compositions as described herein are capable of selectively eliminating autoreactive B cells and thereby removing the pathological cell causing an autoimmune disorder/diseases. Autoreactive B-cells are described herein above and are known to the skilled person as, e.g., illustrated in Immunobiology, Janeway and Travers, 1996 by Current Biology Ltd/Garland Publishing Inc. B lymphocytes bear on their surface highly diverse receptors each of which is specific for a particular antigen and which together are capable of recognizing a wide diversity of antigens. The antigen receptor of B lymphocytes is a membrane-bound form of the antibody that these cells will secrete when activated, see, inter alia, p. 1:6 in Immunbiology, Janeway and Travers, 1996 loc. cit. In the case of autoreactive B cells, these antigens bound to the antigen receptors are self antigens. Autoimmune diseases are mediated by immune responses specific for self antigens; see p. 1:18 in Immunbiology, Janeway and Travers, 1996 loc, cit. In particular and preferably, autoreactive B-cells are B-cells of all differentiation states, resting or activated, which carry a B-cell Ig-receptor on this cell surface and which—due to this feature—are capable of binding to/interacting with (a) specific autoantigen(s). B-cell specific markers are also known in the art and comprise the whole family of membrane bound Ig molecules, preferably IgM+, IgD+ or IgG+, preferably in combination with any of the following markers B220+ (CD45R+), CD19+, CD20+, CD22+, CD21+, CD38+, CD49c+, CD72, CD79α, β+, CDw78+, MHC class II and CD43− (for resting B cells).

Here, it was surprisingly found that constructs comprising an autoreactive antigen or (a) fragment(s) thereof as described herein may be employed for the selective elimination of autoreactive B-cells and/or reduction of autoreactive immunoglobulins. This is surprising since the person skilled in the art would expect that the administration of autoantigen(s) and (a) fragment(s) thereof would lead to a more profound prevalence and/or disease state of autoimmune disorders.

The term "composition", in context of this invention, comprises at least one (poly) peptide construct as defined herein and/or at least one (poly) nucleotide comprising a nucleic acid molecule encoding for such one (poly) peptide construct. Said composition, optionally, further comprises other molecules, either alone or in combination, like e.g. molecules which are capable of modulating and/or interfering with the immune system. The composition may be in solid, liquid or gaseous form and may be, inter alia, in a form of (a) powder(s), (a) tablet(s), (a) solution(s) or (an) aerosol(s). In a preferred embodiment, said composition comprises at least two, preferably three, more preferably four, most preferably (poly)peptide constructs (and/or nucleic acid molecules encoding said constructs) as described in the invention.

The term "selective elimination" as used in accordance with the present invention means elimination of the above mentioned autoreactive B-cells in vivo as well as in vitro. Said term also comprises ex vivo elimination, inter alia, by dialysis approaches. It is preferred that said selective elimination does not hinder the immunological response and/or only minimally influences the natural immunological defense. Preferably, said elimination does not compromise the T-cell mediated immune response and/or does not interfere with non-autoreactive B-cells. It is preferred that said elimination is caused by cytolysis, most preferably said cytolysis is mediated by cytocidal cells, like, macrophages, monocytes, granulocytes, (cytolytic) T-lymphocytes, natural killer (NK) cells and/or lymphokine-activated killer (LAK) cells.

The term "at least one (poly)peptide construct" as employed herein above relates to at least one (poly)peptide construct, at least two, at least three, at least four or at least five (poly)peptide constructs which may be comprised in the composition of the present invention.

The term "at least two domains" as used herein above comprises at least two domains, at least three domains, at least four domains and at least five domains in accordance with the invention.

As employed in accordance with this invention, the term "autoreactive antigen or (a) fragment(s) thereof" means antigens or (a) fragment(s) thereof which are capable of elucidating and/or mediating an autoimmune response. Said fragment(s) thereof is/are preferably an epitope of said antigen. Preferably, said antigens and/or its fragment(s) comprise proteinaceous structures, yet, said autoreactive antigen or (a) fragment(s) may also comprise, either alone or in addition to said proteinaceous structures, inter alia, carbohydrate moieties or lipids. The term autoreactive antigen or (a) fragment(s) thereof" is not limited to antigens occurring in and/or deriving from the subjects own body (autologous and/or endogenic antigens) but furthermore comprises foreign molecules which are capable of eliciting an autoimmune-response by binding and/or interacting with molecules peculiar to one's own body (for example via hapten-carrier complexes). In addition, said term also comprises antigens, like microbial antigens/epitopes, that share properties, e.g. amino acid sequences, with mammalian molecules, e.g. proteins, and are capable of provoking an autoimmune-response. Examples of such antigenic mimicry are known in the art (see, inter alia, Paul, "Fundamental Immunology", Raven Press, 1989) and comprise exogenous antigens like, Steptococcal M protein, Klebsiella nitrogenase, Measels virus P3, retroviral p30 protein. It is preferred that the composition of the present invention comprises a (poly) peptide construct comprising a domain with at least one autoreactive antigen or at least one fragment thereof. However, it is also envisaged that said (poly)peptide construct comprises a domain comprising more than one autoreactive antigens and/or fragments and/or epitopes thereof. Said domain comprising said autoreactive antigen or (a) fragment thereof may therefore comprise several autoantigens and/or fragment(s) thereof. In a preferred embodiment said domain comprises at least one, more preferred at least two, more preferred at least three, more preferred at least four and most preferred at least five autoreactive antigen(s) or (a) fragment(s).

The term "effector molecule capable of interacting with and/or activating NK-cells, T-cells, macrophages, monocytes and/or granulocytes" relates, in accordance with this invention, to molecules capable of engaging, inter alia, lymphocytes and/or FcγR positive cells in effector mechanisms, like the cell-lysis and/or phagocytosis. Said lymphocytes and/or FcγR positive cells comprise the above mentioned NK-cells, macrophages, monophages, monocytes and/or granulocytes, as well as lymphokine-activated killer cells, neutrophiles, eosinophils.

In accordance with the present invention, the term "effector molecule capable of activating the complement system" relates to effector molecules which are capable of activating the classical as well as the alternative complement pathway. Furthermore, said term relates to effector molecules capable of activating any other form of complement mediated lysis.

Useful "effector molecules" in accordance with the present invention are, inter alia, disclosed herein and exemplified in the appended examples.

In a preferred embodiment, the present invention relates to a composition wherein the above described (poly)peptide construct is a fusion (poly)peptide or a mosaic (poly) peptide. Said fusion (poly)peptide may comprise merely the domains of the (poly)peptide construct as described herein above as well as several (a) functional fragment(s) thereof. However, it is also envisaged that said fusion poly)peptide comprises further domains and/or functional streches, Therefore, said fusion poly)peptide can comprise at least one further domain, said domain being linked by covalent or non-covalent bonds. The linkage (as well as the construction of the (poly)peptide constructs comprised in the composition of the present invention), can be based on genetic fusion according to the methods known in the art (Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the fusion poly)peptide may preferably be linked by a flexible linker, advantageously a (poly)peptide linker, wherein said (poly)peptide linker preferably comprises plural, hydrophilic, peptide-bonded amino acids of a length sufficient to span the distance between the C-terminal end of said further domain and the N-terminal end of the peptide, (poly)peptide or antibody or vice versa. Said linker may, inter alia, be a Glycine, a Serine and/or a Glycine/Serine linker. Additional linkers comprise oligomerization domains. Oligomerization domains facilitate the combination of two or several autoantigens or fragments thereof in one functional molecule. Non-limiting examples of oligomerization domains comprise leucine zippers (like jun-fos, GCN4, E/EBP; Kostelny, J. Immunol. 148 (1992), 1547-1553; Zeng, Proc. Natl. Acad. Sci. USA 94 (1997), 3673-3678, Williams, Genes Dev. 5 (1991), 1553-1563;Suter, "Phage Display of Peptides and Proteins", Chapter 11, (1996), Academic Press), antibody-derived oligomerization domains, like constant domains CH1 and CL (Mueller, FEBS Letters 422 (1998), 259-264) and/or tetramerization domains like GCN4-LI (Zerangue, Proc. Natl. Acad. Sci. USA 97 (2000), 3591-3595).

Furthermore, the (poly) peptide construct as described herein may comprise further domains, inter alia, domains which provide for purification means, like, e.g. histidine stretches.

It is also envisaged that the (poly) peptide construct as described herein comprises (a) further domain(s) which may function as immunomodulators. Said immunomodulators comprise, but are not limited to cytokines, lymphokines, T cell co-stimulatory ligands, etc.

Adequate activation resulting in priming of naive T-cells is critical to primary immunoresponses and depends on two signals derived from professional APCs (antigen-presenting cells) like dendritic cells. The first signal is antigen-specific and normally mediated by stimulation of the clonotypic T-cell antigen receptor that is induced by processed antigen presented in the context of MHC class-I or MHC class-II molecules. However, this primary stimulus is insufficient to induce priming responses of naive T-cells, and the second signal is required which is provided by an interaction of specific T-cell surface molecules binding to co-stimulatory ligand molecules on antigen presenting cells, further supporting the proliferation of primed T-cells. The term "T-cell co-stimulatory ligand" therefore denotes in the light of the present invention molecules, which are able to support priming of naive T-cells in combination with the primary stimulus and include, but are not limited to, members of the B7 family of proteins, including B7-1 (CD80) and 137-2 (CD86).

In the light of the present invention, proteinaceous compounds providing the primary activation signal for T-cells can comprise, but are not limited to, anti-CD3-svFv fragments, anti-T-cell receptor svFv fragments or superantigens. Superantigens directly bind to certain subfamilies of T-cell receptor variable regions in an MHC-independent manner thus mediating the primary T-cell activation signal.

Furthermore, the invention also relates to the effector molecule as defined herein, wherein the T-cell co-stimulatory ligand is a cell surface molecule or a fragment thereof expressed on antigen-presenting cells (APC).

Additionally, the effector molecule as defined herein, binding to an APC, may be a T-cell co-stimulatory factor like B7-1 (CD80) or B7-2 (CD86), or adhesion proteins like LFA-3 (CD58), ICAM-1 (CD54), ICAM-2 or ICAM-3 or like the CD137-ligand.

The effector molecule defined herein above may have receptor or ligand function, and may be an immuno-modulating effector molecule or a fragment thereof. An immuno-modulating effector molecule positively and/or negatively influences the humoral and/or cellular immune system, particulary its cellular and/or non-cellular components, its functions, and/or its interactions with other physiological systems.

Said immuno-modulating effector molecule may be selected from the group consisting of cytokines, chemokines, macrophage migration inhibitory factor (MIF; as described, inter alia, in Bernhagen (1998), Mol Med 76(3-4); 151-61 or Metz (1997), Adv Immunol 66,197-223), T-cell receptors and soluble MHC molecules. Such immuno-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). Clin Cancer Res 12, 2682-6; Taub, (1994) Ther. Immunol. 1(4),229-46 or Michiel, (1992). Semin Cancer Biol 3(1),3-15).

Particularly preferred are cytokines which are selected from the group consisting of interleukin(s), interferon(s), TNF(s) and VEGF (Veikkola Semin Cancer Biol 9(3), 211-20), wherein said interleukin(s) comprise, but are not limited to IL-1α, IL-2, IL-3, IL-4, IL-5, IL-6, IL-7, IL-8, IL-9, IL-10, IL-11, IL-12, IL-13, IL-14, IL-15, IL-16, IL-17 and IL-18, wherein interferon(s) comprise IFN-γ as well as IFN-β and IFN-α and wherein TNF(s) comprise members of the lymphotoxin superfamily like TNF-α and TNF-β (Gruss (1996) Int J Clin Lab Res 26(3),143-59). Other suitable cytokines are well known in the art and comprise, inter alia, GM-CSF, G-CSF, M-CSF. In a particular preferred embodiment, said immuno-modulating effector molecule is a chemokine and is selected from the group consisting of IL-8, Eotaxin, GROα, GROβ, GROγ, IP-10, MCP-1, MCP-2, MCP-3, MCP-4, MIG, MIP-1α, MIP-1β, NAP-2, RANTES, I309, Lymphotactin, SDF-1 and C5a.

Further effector molecules may be selected from the group of neuroprotective proteins, such as the neurotrophic growth factors. Examples of such molecules are the neurotrophins nerve growth factor (NGF), brain-derived neurotrophic factor (BDNF), neurotrophin-3 (NT-3), and/or the growth factors IGF-1 and bFGF, and/or the respective receptors of the aforementioned molecules (Connor B., Brain Res. Rev. 27 (1998), 1-39; Lewin, Annual Review of Neuroscience 19 (1996), 289-317; Tessarollo, Cytokine Growth Factor Rev. 9 (1998), 125-137; Snider, Cell 77 (1994), 627-638; Garcia-Estrada, Brain Res. 592 (1992), 3443-347; Lindsay, Trends in Neurosciences 17 (1994), 182-190; Minichiello, Genes Development 10 (1996), 2849-2858). The therapeutic potential of NGF treatment in autoimmune encephalomyelitis has been shown by Villoslada et al. in the marmoset EAE model (J. Exp. Med. 191 (2000), 1799-1806).

Within the scope of the present invention are furthermore effector molecule comprising, inter alia, different immuno-modulating effector molecules. Particularly preferred are effector molecules are cytokines, like IL-2 and GM-CSF.

The (poly)peptide constructs comprised in the composition of the present invention may be constructs which comprise domains originating from one species, preferably from mammals, more preferably from human. However, chimeric and/or humanized constructs are also envisaged and within the scope of the present invention.

In a particular preferred embodiment, the composition of the invention comprises a construct which is a cross-linked (poly)peptide construct. As mentioned herein above, said cross-linking may be based on methods known in the art which comprise recombinant as well as biochemical methods.

The present invention relates in a further embodiment to a composition as described herein above, wherein said autoreactive antigen or (a) fragment(s) thereof is selected from the group consisting of intracellular matrix proteins, extracellular matrix proteins, complement factors, nuclear antigens, cell surface receptors, nuclear receptors, lipids, soluble factors, membrane proteins, heat shock proteins, proteins with sequence similarity to microbial antigens, dietary components and proteins of intercellular structures.

In a more preferred embodiment, said intracellular matrix protein is selected from the group consisting of keratin, filaggrin, antiperinuclear factor 7.

So far, rheumatoid factor (RF), an IgM autoantibody directed against the Fc region of IgG2a, is still the only well-established serological disease marker for rheumatoid arthritis (Tighe (1997). in "Textbook of Rheumatology" W. B. Saunders Company, Philadelphia, Pa. 241-249.). However, rheumatoid factor is not specific for rheumatoid arthritis (RA) and is often negative in the early stages of the disease when a definite diagnosis is not always possible. In the past few years several new autoantibodies have been described which may be more specific for RA than rheumatoid factor. Among these are anti-A2/RA33 antibodies (Hassfeld (1989) Arthritis Rheum. 32: 1515-1520; Hassfeld (1993) Br. J. Rheumatol. 32: 199-203), antikeratin antibodies and the antiperinuclear factor 7 (Youinou (1995) Int. Arch. Allergy Immunol. 107: 508-518; Sebbag (1995) J. Clin. Invest. 95: 2672-2679), and anti-Sa antibodies (Despres, N., G. Boire, F. J. Lopez-Longo, and H. A. Menard (1994) J. Rheumatol. 21: 1027-1033). Anti-A2/RA33 autoantibodies are directed to the RNA binding region of the A2 protein of the heterogeneous nuclear ribonucleoprotein complex (Skriner, J. Clin. Invest. 100 (1997), 127-135). Antibodies to the Sa antigen (streptococcal antigen) cross-react in an example of molecular mimicry with a poorly soluble human protein that is present in normal tissues and that is distinct from all previously described RA-associated autoimmune systems (Depres, J. Rheumatol. 21 (1994), 1027-1033).

Furthermore, the cytokeratin filament-aggregating protein filaggrin is the target of the so-called "antikeratin antibodies," autoantibodies specific for rheumatoid arthritis (Simon (1993) J. Clin. Invest. 92,1387-93).

In yet another embodiment, the present invention relates to a composition as described herein above, wherein said extracellular matrix protein is collagen. It is particularly preferred that said collagen is collagen type IV or collagen XVII. In this context, the autoreactive antigen or (a) fragment thereof may also be the non-collagenous domain of collagen.

Goodpasture's syndrome results from antibodies directed against collagen type IV, in particular the non-collagenous domain of the basement membrane collagen type IV (Butkowski et al. (1987) J. Biol. Chem. 262, 7874-7877; Saus et al. (1988) J. Biol. Chem. 263, 13374-13380). The clinical manifestations of Goodpasture's syndrome are glomerulonephritis and pulmonary hemorrhage (Wilson, C., and Dixon, F. (1986) in the kidney (Berner, B., and Rector, F. eds) $3^{rd}$ Ed., pp800-889, W. B. Saunders Co., Philadelphia).

Serum levels of autoantibodies to hemidesmosomal collagen XVII/BP180 were reported to correlate with disease activity in patients with bullous pemphigoid (see herein below).

In a further embodiment of the present invention, the above mentioned complement factor is C5. It has been shown that the complement factor C5 is a potent autoantigen in rheumatoid arthritis (Volkman, J. Immunol. 158 (1997), 693-706; Grant, Cell Immunol. 167 (1996), 230-240).

Furthermore, in a more preferred embodiment, the present invention relates to the above described composition wherein said nuclear antigen is selected from the group consisting of DNA, histones, snRNPs, topoisomerase I, ro (SS-A-Ro), Ia (SS-B-La), Scl-70, centromer protein (CENP), large ribonuclear particles (RNPs), AL Sm proteins, tRNA synthetase and Ku antigen.

A characteristic feature of rheumatic autoimmune-diseases such as Systemic lupus erythematosus (SLE), progressive systemic sclerosis, polymyositis, mixed connective tissue disease (MCTD), or RA is the occurrence of autoantibodies to intracellular antigens (von Muehlen (1995) Semin. Erthritis Rhem. 24, 323-358; Peng (1997) in "Textbook of Rheumatology." W. B. Saunders Company, Philadelphia, Pa. 250-266). For reasons which are not yet fully understood, these autoantibodies are often directed to components of large ribonucleoprotein (RNP) structures such as the ribosome or the spliceosome (van Venrooij (1995) Curr. Opin. Immunol. 7: 819-824). Some of these autoantibodies specifically occur in only one disease, which makes them very useful for diagnosis and treatment. Thus, autoantibodies to double-stranded DNA or to the Sm antigen (Brahms, JBC 275 (2000), 17122) are highly specific for SLE, autoantibodies to topoisomerase (anti-Scl70) (Mukai, J. Rheumatol. 20 (1993), 1594-1497, van Venrooij, Curr. Opin. Immunol. 7 (1995), 819-824) are exclusively detected in patients with progressive systemic sclerosis, and autoantibodies to tRNA synthetases (e.g., anti-Jo1) (Marguerie, Q. J. Med. 77 (1990), 1019-1038) occur only in patients with poly- or dermatomyositis.

Systemic lupus erythematosus (SLE) is an idiopathic autoimmune disease in which self-reactive autoantibodies (Cabral (1997); Curr. Opin. Rheumatol. 9, 387-392) cause disease either by directly binding to self-antigens or following the deposition of antibody-antigen immune complexes in blood vessels leading to vasculitis, glomerulonephritis and arthritic tissue damage (Rothfield (1985) in "Arthritis and Allied Conditions", Lea & Febiger, Philadelphia, pp. 911-935). The estimated prevalence of SLE in the U.S. is 45/100,000, with the peak incidence in women ages 20-40 (Hochberg (1997) in "Dubois' Lupus Erythematosus", Williams & Wilkins, Baltimore, pp. 49-65). Proteins cleaved by interleukin-1 beta converting enzyme family proteases during apoptosis, as well as the Sm proteins B/B', D1, and D3 of the spliceosome, are common targets for autoantibody production in patients with systemic lupus erythematosus (SLE) (Brahms (2000) JBC 275, 17122 ff.). In addition, immune responses to SS-A 52-kDa and 60-kDa proteins and to SS-B 50-kDa protein have been shown in mothers of infants with neonatal lupus erythematosus (Yukiko (2000) Br. J. Dermatol. 142, 908-912). Photosensitivity of lupus erythematosus was correlated with the expression of SS-A/ Ro and SS-B/La antigens in skin biopsy specimens of patients (Ioannides (2000) Arch Dermatol 136, 340-346). Wang et al. (J. Clin. Invest. (1999) 104, 1265-1275) have identified a novel 75-kDa phosphoprotein associated with SS-A/Ro and distinct human autoantibodies directed against it. Circulating anticentromere CENP-A and CENP-B antibodies were identified in patients with diffuse and limited systemic sclerosis, systemic lupus erythematosus, and rheumatoid arthritis (Russo (2000) J Rheumatol. 27, 142-148). Ku is a heterodimeric protein composed of approximately 70- and approximately 80-kDa subunits (Ku70 and Ku80) originally identified as an autoantigen recognized by the sera of patients with autoimmune diseases (Tuteja (2000) Crit Rev Biochem Mol Biol 35, 1-33).

The present invention relates furthermore to a composition as described herein wherein said autoreactive antigen or (a) fragment thereof is a cell surface receptor and wherein said a cell surface receptor is selected from the group consisting of TSH-receptor, Ach-receptor, asialo-glycoprotein receptor and platelet integrin GpIIb:IIIa.

Grave's disease is an autoimmune condition characterized typically by hyperthyroidism, thyroid hyperplasia, and additional signs of ophthalmopathy, pretibial myxedema, or acropachy. The pathophysiological mechanisms responsible for thyrotoxicosis and thyroid hyperplasia are attributed to autoantibodies directed against the thyrotropin receptor (TSHr). Said antibodies activate the TSH receptor, which results in cAMP-dependent stimulation of thyrocyte function and growth (McKenzien (1995) in "Endocrinology". ";. W. B. Saunders Co. Philadelphia, Pa.; pp 676-711).

Autoantibodies directed against the acetylcholine receptor (Ach-receptor) are involved in Myasthenia gravis, an autoimmune disease which leads to a reduction of the number of (Ach-R) at the muscular motor endplate (see, inter alia, Heitmiller (1999) Semin. Thorac Cardiovasc. Surg., 11, 41-46 or Atassi (1997) Crit. Rev. Immunol.;17, 481-495). In addition, autoantibodies directed against the human asialo glycoprotein receptor are described in autoimmune hepatitis (Bojic (1997) Med. Pregl. 50, 363-8).

Furthermore, autoantibodies against platelet integrin GpIb:IIIa are the cause for autoimmune thrombocytopenic purpura resulting in abnormal bleeding (Beardsley and Ertem (1998) Transfus. Sci. 19, 237-244). Myasthenia gravis is caused by autoantibodies against the nicotinic acetylcholine receptors (AchR) leading to the downregulation of receptors and complement dependent lysis of the neuromuscular junction. The consequences are defects in neuromuscular transmission, culminating in weakness and fatigue of skeletal muscles in MG patients (Fambrough (1973) Science 182, 293-295; Kao (1977) Science, 196, 527-529; Heinemann (1977) Proc. Natl Acad. Sci. USA 7, 3090-3094).

In an even more preferred embodiment, the present invention provides for a composition wherein the soluble factor mentioned herein above is selected from the group consisting of I-antigen, Rh-blood group factor, 21-hydrolase enzyme, glutamic acid decarboxylase (GAD), insulin, (ICA) 512, ICAP-69, (tissue) transglutaminase (tTG), transaldolase, S100beta, oxidized low-density lipoprotein (ox-LDL), crystallin, CNPase, proteinase 3 and type I antigen.

Autoimmune hemolytic anemia is caused by antibodies against Rh blood group antigens and type I antigens, destroying red blood cells and resulting in anemia (Leddy (1993); J. Clin Invest. 91, 1672-1680; Leddy (1994); 84, 650-656) Celiac disease, also referred to gluten sensitive enteropathy is characterized by IgA autoantibodies against anti-tissue transglutaminase and antiendomysial antibodies (EMA). (Lock, R. J. (1999) J Clin Pathol April 1999;52(4): 274-277; Rose, C. (1999) J Am Acad Dermatol 41, 957-961; Vitoria, J. C. (1999) J Pediatr Gastroenterol Nutr 29, 571-574; Schuppan, D. (2000) Gastroenterology 119, 234-242).

Auto-antibodies to oxidized low-density lipoprotein (ox-LDL) are thought to play a pivotal role in the pathogenesis of atherosclerosis and can serve as a marker of coronary artery disease in patients with familial hypercholesterolaemia (Paiker (2000) Ann Clin Biochem 37, 174-178).

Insulin-dependent diabetes mellitus (IDDM) is traditionally classified as a T-cell dependent autoimmune disease. However autoreactive antibodies are present in patients with IDDM. Contributions of the humoral response to the onset of disease and disease progression of IDDM was shown (Bonifacio (2000) Diabetes 49, 202-208; Coleman (2000) Diabetologia 43, 203-209; Rulli, M. (1999) Autoimmunity 31, 187-193). Also a connection between autoantibodies to diabetes mellitus and celiac disease was shown (Galli-Tsinopoulou A (1999) Horm Res 52, 119-124). A major target of autoimmunity in preclinical type 1 diabetes is glutamic acid decarboxylase, GAD, specific examples are GAD65, GAD67 (Bonifacio (2000) Diabetes 49, 202-208). Islet cell autoantigen (ICA) 512 is an autoantigen of insulin-dependent diabetes mellitus (IDDM) which is homologous to receptor-type protein tyrosine phosphatases (++PTPases). ICA 512 is an intrinsic membrane protein of secretory granules expressed in insulin-producing pancreatic beta-cells as well as in virtually all other peptide-secreting endocrine cells and neurons containing neurosecretory granules (Solimena (1996) EMBO J 15, 2102-2014). Other autoantigens in IDDM are ICAp69, (Karges (1996) Diabetes 45, 513-521). Anti-insulin antibodies were shown to be linked to the onset of diabetes (Yu (2000) Proc Natl Acad Sci USA 97, 1701-1706).

Granulomatosis also known Morbus Wegener (Hewis, Curr. Opin. Rheumatol. 12 (2000), 3-10) is caused by autoantibodies against proteinase 3, a constituent of neutrophil azurophilic granules.

In addition, the present invention provides for a composition as described herein above, wherein said heat shock protein is selected from the group consisting of alpha B-crystallin, Hsp27, HSP70 and HSP60. Alpha B-crystallin and Hsp27 have been implied in multiple sclerosis (Agius, Acta Neurol. Scand. 100 (1999), 139-147). Furthermore, antibodies to mycobacterial heat shock proteins bind to human myelin and to oligodendrocytes recognizing human autoantigens, including HSP70 and myelin protein CNP (Salvetti, J. Neuroimmunol. 64 (1996), 143-153; Salvetti, J. Autoimmun. 5 (1992), 691-702; Birnbaum, Ann. N.Y. Acad. Sci. 835 (1997), 157-167; Jones, Immunol. Today 14 (1993), 115-118). Antibodies against *Escherichia coli* and chlamydial Hsp60 were shown to crossreact with human HSP60 (Mayr, Circulation 99 (1999), 1560-1566). Retinal autoantigens include Hsc70 (Ohguro, Invest. Ophthalmol. Vis. Sci. 40 (1999), 82-89).

As will be discussed in detail herein below, several proteins have been identified that can act as autoantigens in multiple sclerosis, including the soluble proteins CNPase, Transaldolase, S100β, B- crystallin and other heat shock proteins (see, Schmidt (1999) Multiple Sclerosis 5, 147-160 or Bajramovic (2000) J Neuroimmunol 106, 14-22).

The present invention relates, in a more preferred embodiment, to a composition as described herein above, wherein said membrane protein is selected from the group consisting of PLP, MAG, MBP, MOG, Golgi-proteins, cytochrome P450 (CYPs) and UDP-glucuronosyltransferase (UGTs).

Multiple sclerosis (MS) is a chronic inflammatory disease of the central nervous system (CNS) of autoimmune origin, characterized by focal demyelination, loss of oligodendrocytes, and astrocytic scar formation in advanced stages of the disease. Histopathologically, acute inflammatory lesions are characterized by infiltrating lymphocytes and macrophages scattered throughout the periventricular white matter, spinal cord, brainstem and optic nerves. In the later stages of the disease, vascular infiltrates are less prominent, and loss of myelin and oligodendrocytes predominates. While MS has been widely classified to be a majorly T-cell mediated disease, it is now recognized that MS has both a T-cell and a B-cell component (Ewing (1998) Immunology and Cell Biology 76, 47-54; Weckerle (1999) Nature Medicine 5, 153-154; Genain (1999) Nature Medicine, 5, 170-175; Schmidt (1999) loc.cit; Lindert (1999) Brain 122, 2089-2099). Eventually, myelin breakdown as the hallmark of the disease is brought about by the combined effects of autoantibodies against myelin proteins, complement activation, cytotoxic cells and cytokine-induced toxicity.

As mentioned herein above, several soluble proteins have been identified as being involved as autoantigens in multiple sclerosis, including the above discussed soluble proteins like, CNPase, transaldolase, S100β or B-crystallin and/or other heat shock proteins However further proteins play major roles in MS. These proteins comprise myelin basic protein (MBP), myelin oligodendrocyte glycoprotein (MOG), PLP, MAG, (Schmidt (1999) loc.cit.). While it was long thought that the major myelin component MBP was the major target antigen in MS, studies of the experimental animal model of MS, experimental autoimmune encephalomyelitis (EAE), have suggested that other candidate autoantigens may be more relevant to the disease. Indeed, the MOG protein, a minor constituent of myelin sheaths (0.05% of total myelin) and exclusively expressed as a cell-surface protein on their outermost surface layer, has been shown to be the only single protein able to induce Chronic relapsing EAE (CREAE) in the Lewis Rat. CREAE is thought to be the most appropriate animal model for MS. MOG is a membrane glycoprotein found predominantly in the outermost lamella of the myelin sheaths that wrap and insulate axons in the CNS. It is a minor protein component of myelin representing just 0.05% of the total protein content, in contrast to other myelin proteins with encephalitogenic potential such as proteolipid protein (PLP) making up 20% of myelin protein. Nonetheless, immunization with MOG induces severe chronic EAE characteristically accompanied by strong inflammatory and de-myelinating lesions of the CNS (Iglesias, Glia, in press (2001). It was demonstrated that MOG-induced EAE comprises an important pathogenic antibody component (Schluesener, J. Immunol. 139, (1987), 4016-4021 and Litzenburger, J. Exp. Med. 188, (1998), 169-180). Hence strategies aimed at treating MS should not neglect the targeting and possible elimination of MOG-specific B cell clones. While transfer of MOG-specific T-cells has no apparent consequences in the recipient animal, co-transfer of T-cells and antibodies against MOG can induce EAE in animal models, resembling multiple sclerosis in humans (Stefferl (1999) J. Immunol. 163, 40-49). These findings suggest that auto-antibodies against MOG play a central role in disease development and progression. Gold-labeled MOG peptides have been shown to bind specifically to disintegrating myelin around axons in lesions of acute multiple sclerosis and in MOG-induced EAE in the marmoset model for MS, providing direct evidence that autoantibodies against MOG mediate target membrane damage in central nervous system demyelinating disease (Genain (1999) Nature Medicine, 5, 170-175; Raine (1999), Ann. Neurol. 46, 144-160). In a comparative study, MOG antibodies were shown to be common in patients with multiple sclerosis (Reindl (1999) Brain, 122, 2047-2056). Therefore, and due to the central role of MOG-specific B-cells in MS in a further embodiment of the present invention, the composition of the present invention is particularly useful for the selective elimination of these autoreactive lymphocytes (see herein below).

Cytochromes P450 (CYPs) and UDP-glucuronosyltransferases (UGTs) are targets of autoantibodies in several hepatic and extrahepatic autoimmune diseases (Obermayer-Straup (2000) Can. J Gastroenterol 14, 429-39).

A number of Golgi proteins have been described as autoantigens, recognized by sera from patients with various forms of rheumatic diseases. Examples of Golgi autoantigens are golgin-67, golgin-95/gm130, golgin-160, giantin, golgin-97, p230, golgin245 and p210 (Eystathioy, (2000) J Autoimmun 14, 179-187; Mancini,. (2000) J Cell Biol 149, 603-12; Linstedt (1993) Mol Biol Cell 4, 679-93; Griffith (1997) Arthritis Rheum 40, 1693-1702; Erlich (1996) J Biol Chem 271, 18328-18337; Fritzler (1995) J Biol Chem 270, 31262-31268; Fritzler (1993) J Exp Med. 178, 49-62; Fritzler (1984) J Immunol. 132, 2904-2908; Rios (1994) J Cell Biol 125, 997-1013; Renier (1994) J Autoimmun 7, 133-143).

In yet a further embodiment, the present invention provides for a composition for the selective elimination of autoreactive B-cells as described herein above, wherein said proteins sharing sequence similarity with microbial antigens or dietary proteins/components are selected from the group consisting of antigens mimicking proteins, polypeptides and/or carbohydrate structures from Streptococcus, Klebsiella, Proteus, M. tuberculosis, adenovirus, poliovirus, measles virus, retrovirus, papilloma virus, gluten and/or butyrophilin.

Microbial antigens can share regions of amino acid sequences homology with mammalian proteins. Said microbial antigens can, therefore, elicit an autoimmune response, being an example of antigenic mimicry. The composition of the present invention is, inter alia, useful for treating, preventing and/or ameliorating autoimmune responses due to such an antigenic mimicry of microbial organisms. Examples of exogenous antigenic mimicry are known in the art and, inter alia, described in Paul, "Fundamental Immunology", Raven Press, 1989.

For example, acute rheumatic fever is caused by antibodies against streptococcal cell-wall antigens that cross-react with cardiac muscle and lead to arthritis, myocarditis and late scarring of heart valves (Khanna (1997) J. Autoimmun. 10, 99-106; Bronze (1993) J. Immunol. 151, 2820-2828; Quinn. (1998) Infect Immun 66, 4418-4424). As discussed herein above, antibodies directed against the Sa antigen (streptococcal antigen) have been described in rheumatoid arthritis (Depres (1994), loc. cit.).

Furthermore, cross-reactivities of autoimmune antibodies exist between HLA-B27 and some Klebsiella strains, in particular of *Klebsiella pneumoniae* (see, inter alia, Dominguez-Lopez (2000) J. Rheumatol. 27, 1453-1460). This cross-reactivities lead to ankylosing spondylitis.

Another example of antigenc mimicry which leads to autoimmune reactions, especially in rheumatoid arthritis, is the cross-reaction to HLA-DR antigens with proteins/(poly) peptides of Proteus mirabilis (see, eg. Ebringer (1992), Ann. Rheum. Dis. 51, 1245-6 or Ebringer (2000), J Med Microbiol 49, 305-11).

Furthermore, an autoimmune pathogenesis of atherosclerosis is described and a cross-reactivity with human heat shock protein 60 (hsp60), expressed by endothelial cells, is involved in said autoimmune disease (Wick (2000), Herz 25,87-90).

In addition, the measles virus P3 protein resembles the above described autoantigen MBP and may elucidate EAE.

In a further embodiment, the present invention provides for a composition as described herein above, when said dietary component is gluten or butyrophilin. In context of the present invention, dietary components are nutrients that share structural or sequence similarity with mammalian and/or human proteins or post-trnslational modifications of human proteins, like N- or O-linked glycans. Such dietary components can cause molecular mimicry and induce an autoimmune reaction. Examples of dietary components are gluten and the milk constituent butyrophilin. Celiac disease, also referred to as gluten sensitive enteropathy is characterized by IgA autoantibodies against anti-tissue transglutaminase and antiendomysial antibodies (EMA). (Lock, J Clin Pathol 52 (1999), 274-277; Rose, J Am Acad Derm 41 (1999) 957-961; Vitoria, J Pediatr Gastro Nutr 29 (1999), 571-574; Schuppan, Gastroent 119 (2000), 234-242). Butyprophilin shares sequence homology to MOG. Butyrophilin has been shown to modulate animal models of multiple sclerosis due to molecular mimicry with MOG (Stefferl, J Immunol 165 (2000), 2859-2865).

The present invention also relates to a composition wherein said protein of intercellular structures as described herein above is selected from the group consisting of desmoglein-1 (Dsy1), desmoglein-3 (Dsy3), desmocollin, desmoplakin, envoplakin, periplakin, BP180, BPAG-1, BPAG-2 and HD1/plectin.

*Pemphigus vulgaris* and pemphigus foliaceus are caused by antibodies against keratinocyte adhesion molecules desmoglein 3 (Dsg3) and desmoglein I (Dsg1), respectively (Amagai, (1991) Cell 67, 869-877; Allen(1993), J Invest Dermatol 100, 685-91).

Other desmosomal or hemi-desmosomal proteins have been implied in pemphigus-related autoimmune diseases, in addition to desmogleins, also antibodies against desmoplakin, desmocollin, envoplakin, periplakin have been reported (Gooptu, (1999) Br. J. Dermatol. 141, 882-886; Chorzelski (1999) J Am Acad Dermatol 41, 393-400; Anhalt (1999) J. Am. Acad. Dermatol. 5, 763-6). Additional auto antigens are bullous pemphigoid antigens 1 (BPAG 1) and 2 (BPAG 2), BP230 (Schmidt, (2000) Arch Dermatol 136, 174-178; Michelson (2000) J Histochem Cytochem 48, 535-544; Schuhmann (2000) Am J Pathol 156, 685-95; Dopp (2000) J. Am. Acad. Dermatol. 42, 577-583).

HD1/plectin, another member of the plakin family, has been described to be recognized by sera from PNP (paraneoplastic pemphigus) patients (Proby (1999), J. Invest. Derm. 112, 153-156).

In a yet more preferred embodiment, the present invention relates to a composition, as described herein wherein said T cells are cytotoxic T cells.

Furthermore, the present invention relates to a composition for the selective elimination of autoreactive B-cells comprising at least one (poly)peptide construct consisting of at least two domains wherein one of said domains comprises an autoreactive antigen or (a) fragment(s) thereof specifically recognized by the Ig receptors of said autoreactive B-cells and wherein one of said domains comprises an effector molecule capable of interacting with and/or of activating NK-cells, T-cells, macrophages, monocytes and/or granulocytes, wherein said effector molecule is a receptor-ligand or the Fc-part of an immunoglobulin. It is particularly preferred that said effector molecule specifically binds to a molecule of the CD3-receptor complex. It is even more preferred that said receptor-ligand is an antibody or (a) fragment(s) or derivative thereof or an aptamer.

In accordance with the present invention the term "antibody" relates to monoclonal or polyclonal antibodies. Polyclonal antibodies (antiserum) can be obtained according to conventional protocols. Antibody fragments or derivatives comprise F(ab')$_2$, Fab, Fv or scFv fragments; see, for example, Harlow and Lane, "Antibodies, A Laboratory Manual", CSH Press 1988, Cold Spring Harbor, N.Y., Furthermore, in accordance with the present invention, the derivatives of the antibodies can be produced by peptidomimetics. In the context of the present invention, the term "aptamer" comprises nucleic acid aptamers such as RNA, ssDNA (ss=single stranded), modified RNA, modified ssDNA or PNAs which bind a plurality of target sequences having a high specificity and affinity. Nucleic acid aptamers are well known in the art and, inter alia, described in Famulok, Curr. Op. Chem. Biol. 2 (1998), 320-327. The preparation of aptamers is well known in the art and may involve, inter alia, the use of combinatorial RNA libraries to identify binding sites (Gold, Ann. Rev. Biochem. 64 (1995), 763-797). Said other receptors may, for example, be derived from said antibody etc. by peptidomimetics.

In a particular preferred embodiment of the present invention, the above mentioned antibody derivative is a scFv directed against a molecule of the CD3 receptor complex.

In accordance with the present invention, the term "molecule of the CD3 receptor complex" comprises any invariable proteins and or fragments thereof, which comprise CD3α, CD3β, CD3γ, CD3δ, CD3ε and CD3ζ (CD3α and CD3β are also known as TCRα and TCRβ). It is particularly preferred that said scFv is directed against the CD3ε chain of the T-cell receptor complex. Single chain constructs comprising such a specificity are known in the art and, inter alia, described in Mack (1997), J. Immunol. 158, 3965-3970 or in the appended illustrative examples.

In a most preferred embodiment, the present invention relates to a composition for the selective elimination of autoreactive B-cells comprising at least one (poly)peptide construct consisting of at least two domains wherein one of said domains comprises an autoreactive antigen or (a) fragment(s) thereof specifically recognized by the Ig receptors of said autoreactive B-cells and wherein one of said domains comprises an effector molecule capable of interacting with and/or of activating NK-cells, T-cells, macrophages, monocytes and/or granulocytes, wherein said domain comprising an autoreactive antigen or (a) fragment thereof is MOG or (a) fragment(s) thereof and wherein said domain comprising an immunological effector molecule is an anti-CD3 receptor or an Fc-part of an immunoglobulin.

The compositions as disclosed herein are in particular useful for the elimination of autoreactive B-cells in vitro, in vivo and ex vivo. The appended examples illustrate that not only in vitro depletions but also ex vivo as well as in vivo depletions are envisaged with the composition of the present invention. In addition, it is illustrated that the present invention also provides for compositions which may be employed for the reduction of auto-reactive, antigen-specific immunoglobulins.

The above mentioned composition will be particularly useful in treating, preventing and/or ameliorating autoimmune diseases, like multiple sclerosis. As described herein above, MOG is one of the major autoantigens involved in multiple sclerosis.

The protein and/or nucleotides sequence of MOG are known to the person skilled in the art and described, inter alia, in WO 95/06727 or U.S. Pat. No. 5,532,351. Approaches to affect the T cell arm of multiple sclerosis include induction of tolerance using synthetic peptides against the activation of MOG-specific T-helper cells (see, WO 95/07096, WO 96/12737, WO 97/35879, WO 99/12966). However, these approaches do not influence, ameliorate and/or modify the B-cell related symptoms of the autoimmune reaction in multiple sclerosis.

The above described MOG belongs to the family of B7 homologous proteins, sharing the membrane topology and the extracellular immunoglobulin domain (Johns, (1999) J. Neurochem. 72, 1-9). Several human homologues to MOG have been identified, but none of them has been reported to be an auto-antigen in MS. One homologue to MOG has been described that is expressed in B lymphocytes (WO 98/33912). Furthermore, fusion proteins of MOG or MOG homologues with Fc portions have been described (WO 98/33912, WO 99/23867), yet, said Fc-portion fusion proteins have been designed to enhance protein expression and for use as an affinity tag for purification. Often a protease site is introduced to remove the Fc portion after purification. This approach has been described in (EP 0 464 533). The above recited approaches of MOG-Fc fusion proteins have neither been proposed nor envisaged the uses and compositions described herein, namely for the elimination of autoreactive B-cells via binding, inter alia, to the B cell receptor and interaction with, e.g. complement or an Fc-receptor bearing effector cell.

The present invention relates in a further embodiment to a composition for the selective elimination of autoreactive B-cells wherein said at least one (poly) peptide construct is encoded by (a) a polynucleotide comprising a nucleic acid molecule encoding the polypeptide as depicted in SEQ ID NO. 2 or 4; (b) a polynucleotide comprising a nucleic acid molecule having the DNA sequence as depicted in SEQ ID NO. 1 or 3; (c) a polynucleotide hybridizing to a sequence which is complementary to a nucleotide sequence of (a) or (b); or (d) a nucleotide sequence being degenerate to the sequence of the nucleotide sequence of (c).

The above mentioned polynucleotide may be a naturally occurring nucleic acid molecule as well as a recombinant nucleic acid molecule. Said polynucleotide/nucleic acid molecule may, therefore, be of natural origin, synthetic or semi-synthetic.

It is also immediately evident to the person skilled in the art that regulatory sequences may be added to the nucleic acid molecule of the invention. For example, promoters, transcriptional enhancers and/or sequences which allow for induced expression of the above described polynucleotide may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62).

The above described polynucleotide/nucleic acid molecules may either be DNA or RNA or a hybrid thereof.

With respect to the polynucleotides/nucleotide sequences characterized under (c) above, the term "hybridizing" in this context is understood as referring to conventional hybridization conditions, preferably such as hybridization in 50% formamide/6×SSC/0.1% SDS and 100 μg/ml ssDNA, in which temperatures for hybridization are above 37° C. and temperatures for washing in 0.1×SSC/0.1% SDS are above 55° C. Most preferably, the term "hybridizing" refers to stringent hybridization conditions, for example such as described in Sambrook., "Molecular Cloning: A Laboratory Manual", Cold Spring Harbor Laboratory Press, Cold Spring Harbor, N.Y., 1989.

Furthermore, said polynucleotide/nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which -allows for the transcription of said nucleic acid molecule in the cell.

The polynucleotide/nucleic acid molecule of the composition of the present invention may be a recombinantly produced chimeric nucleic acid molecule comprising any of the aforementioned nucleic acid molecules either alone or in combination. Preferably, the nucleic acid molecule of the invention is part of a vector.

In a particularly preferred embodiment, (poly)peptide construct of the composition of the present invention is a (poly)peptide comprising the amino acid sequence as depicted in SEQ ID NO. 2 or 4. Furthermore, (poly)peptide constructs are envisaged, wherein the sequence as shown in SEQ ID No.: 2 or 4 comprises at least one modification.

Said modification(s) may be selected from the group consisting of amino acid exchange(s), insertion(s), deletion(s), addition(s), substitution(s), inversion(s) and duplication(s). Said modification(s) also comprise conservative and/or homologue amino acid exchange(s). For example, guidance concerning how to make phenotypically/functionally silent amino acid substitution is given in Bowie (1990), Science 247, 1306-1310. Moreover, tolerated conservative amino acid substitutions involve replacement of the aliphatic or hydrophobic amino acids Ala, Val, Leu and lie; replacement of the hydroxyl residues Ser and Thr; replacement of the acidic residues Asp and Glu; replacement of the amide residues Asn and Gln; replacement of the basic residues Lys, Arg, and His; replacement of the aromatic residues Phe, Tyr, and Trp, and replacement of the small-sized amino acid substitution, variants of peptides of this invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature (poly)peptide construct with another compound, such as a compound to increase the stability and/or solubility of the polypeptide (for example, polyethylene glycol), or (iv) fusion of the (poly)peptide construct with additional amino acids, or leader or secretory sequence, or a sequence facilitating purification. Such variant (poly)peptide construct are deemed to be within the scope of those skilled in the art from the teachings herein.

Thus, the present invention also relates to peptides which are at least 60%, more preferably at least 70%, more preferably at least 80%, more preferably 90%, more preferably at least 95% and most preferably 99% identical or homologous to the (poly)peptide construct as shown in SEQ ID NO: 2 or 4. Specific strategies for obtaining (poly)peptide constructs described herein above are known in the art. These methods comprise recombinant and biochemical methods and are, inter alia, disclosed in Sambrook, loc. cit. Said methods also comprise protein engineering or direct synthesis.

Yet, in a further embodiment, the present invention relates to a composition for the selective elimination of autoreactive B-cells comprising at least one polynucleotide encoding at least one (poly)peptide construct as described herein. The embodiments described herein above may be applied, mutatis mutantis, for the polynucleotide/nucleic acid molecule encoding said at least one (poly)peptide construct. It is understood that compositions as described herein and comprising at least one polynucleotide encoding at least one (poly)peptide construct as described herein may also be employed for the selective reduction of autoreactive, antigen-specific immunoglobulins.

Additionally, in a more preferred embodiment of the composition of the invention said polynucleotide/nucleic acid molecule is part of a vector. In a particularly preferred embodiment said vector is an expression vector.

Said vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions. Particularly preferred vectors are vectors as, inter alia, described in the appended examples and comprise, e.g. the expression vector CD19xCD3 pEF-dhfr.

Furthermore, the vector of the composition of the present invention, may in addition to the polynucleotides/nucleic acid sequences described herein above, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymikine kinase promoter, SV40, RSV-promoter (*Rous sarcoma* virus), human elongation factor 1α-promoter, enhancers, like CMV enhancer or SV40-enhancer. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (Invitrogene), pSPORT1, pEF-dhfr or prokaryotic expression vectors, such as lambda gt11, pDS or pET. Beside the nucleic acid described herein, the vector may further comprise nucleic acid sequences encoding for secretion signals. Such sequences are well known to the person skilled in the art. Furthermore, depending on the expression system used leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusionprotein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the peptide(s) or fragments thereof of the invention may follow.

As mentioned herein above, the vector of the composition of the present invention may also be an expression vector. Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, -Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, vectors and/or gene delivery systems are also described in gene therapy approaches in immunology or in neurology, for example Linden, Proc. Natl. Acad. Sci. U.S.A. 93 (1996), 11288-11294; Maass, Hum. Gene Ther. 9 (1998), 1049-1059; Hallek, Cytokines Mol. Ther. 2 (1996), 69-79; Peel, Neurosci. Methods 98 (2000), 95-104; Chen, J. Neurosci. Res. 55 (1999), 504-513. The nucleic acid molecules and vectors described herein and comprised in the composition of the present invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention. As documented in the appended examples, (poly) peptide constructs comprised in the composition of the present invention may also be expressed in mammalian expression systems, for example in CHO-cells.

As will be discussed herein below, the composition of the present nivention comprising nucleic acid molecule as described herein above and/or the above described vectors/hosts may be particularly useful in treating, preventing and/or ameliorating an autoimmune desease/disorder. Therefore, said compositions may be employed in gene therapy approaches.

For gene therapy applications, said nucleic acids encoding the (poly)peptide constructs as described herein may be cloned into a gene delivering system, such as a virus Therefore, it is particularly preferred that the of the present invention comprises a host transformed with the vector described herein above. It is even more preferred that said host is a mammalian cell, most preferred is a human cell.

In yet a further embodiment, the present invention relates to a composition as described herein above which further comprises a compound capable of selectively eliminating plasma cells and/or a compound capable of selectively eliminating (an) auto-antibody(ies). Preferably, said compound capable of selectively eliminating plasma cells is an antibody or (a) fragment(s) or a derivative thereof specifically detecting an plasma cell-specific epitope. Even more preferably, said compound capable of selectively eliminating (an) auto-antibody(ies) is an anti-idiotypic antibody or (a) fragment(s) or a derivative thereof specifically reacting with said auto-antibody(ies).

Furthermore, the present invention provides for compositions as described herein for the selective reduction of autoreactive immunoglobulins/for the selective elimination of auto-antibody(ies). As documented in the appended examples the constructs as disclosed herein and employed in the compositions of the present invention are not only capable of selectively eliminating autoreactive B-cells but also of reducing titers of autoreactive immunoglobulins. Preferably, said selective reduction of autoreactive immunoglobulins leads to a titer-reduction of at least 20%, at least 40%, at least 50%, at least 60%, most preferably at least 70%. Titers of autoreactive immunoglobulins may be measured by methods known in the art and as shown in the appended examples, e.g. the measurement of circulating autoreactive immunoglobulins. Such methods, e.g., methods of detecting autoantibodies in sera comprise ELISA-tests, RIA, immunodiffusions, immunoprecipitations, Western blotting, affinity-chromatographie. Furthermore, in situ-methods are envisaged which comprise the use of labeled peptide, preferably immunogold-labeled peptides and high-resolution microscopy.

In a most preferred embodiment of the present invention, the composition of the present invention is a pharmaceutical composition optionally comprising a pharmaceutically acceptable carrier.

The pharmaceutical composition of the present invention may be particularly useful in preventing, ameliorating and/or treating autoimmune disorders/diseases, as described herein above and herein below.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in a brain artery or directly into brain tissue. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg per dose; however, doses below or above this exemplary range are envisioned, especially considering the aforementioned factors. If the regimen is a continuous infusion, it should also be in the range of 1 μg to 10 mg units per kilogram of body weight per minute, respectively. In context of the present invention, it is preferred that that the peptides of the present invention are employed in concentrations of less than 500 μg/ml, more preferred at less than 100 μg/ml, more preferred of less than 10 μg/ml and most preferred of less than 1 μg/ml.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be drugs acting on the immune system, like FK506, cyclosporin, IFNbeta, azathioprine, cyclophosphamide, prednisone, corticosferoids, cyclosporin A, calcineurin, rapamycin and neuroprotective agents such as the neurotrophins (NGF, BDNF, NT-3); see also Webster, Mult. Scler. 3 (1997), 113-120; Ebadi, Neurochem. Int. 30 (1997), 347-374.

The compositions, also the pharmaceutical compositions, of the present invention may be tested for functionality by different approaches. For example, as a surrogate test system several approaches can be chosen: 1) Establishment of a B-cell derived cell line expressing a membrane-bound Ig derived from a murine hybridoma cell line specific for the auto-antigen, 2) Hybridoma cells expressing membrane-bound Ig could be isolated using auto-antigen; 3) Alternatively, autoreactive B cells may be derived from transgenic mice with autoreactive B cells. Mouse models which may be employed are known in the art. For example, Litzenburger (see J. Exp. Med. (1998) 188, 169-180) has establised such a mouse model for multiple sclerosis using the DNA sequences of the heavy chain variable domain encoding the 8.18-C5 antibody to MOG. Further in-vivo models for B-cell dominant autoimmune diseases have been reviewed in Murakami and Tasuku (Curr. Opin. Immunol. (1997) 9, 846-850), Christadoss et al. (Clin. Immunol. (2000) 94, 75-87). Experimental autoimmune encephalomyelitis (EAE) in rats and marmorsets can be used as a surrogate model for multiple sclerosis ('t Hart et al. (2000) Immunol. Today 21, 290-297; Stefferl et al. (1999) J. Immunol. 163, 4049). It is also envisaged that the above mentioned functionality approach comprises the measurement of circulating immunoglobulins and in particular of autoreactive immunoglobulins after administration of a composition as defined herein. Such a measurement is shown in the appended examples and may easily be employed in samples from test animals, as well as in samples of humans. Preferably, said sample is a blood sample.

The present invention relates in another embodiment to the use of at least one (poly)peptide construct as defined herein, of at least one polynucleotide described herein above or encoding at least one (poly)peptide construct as defined herein or of at least one vector described herein above for the preparation of a pharmaceutical composition for the treatment, amelioration and/or prevention of an autoimmune disease, preferably of a human autoimmune disease. Said pharmaceutical composition may be useful for the autoimmune diseases and disorders mentioned herein above and are particularly useful for the treatment, prevention or amelioration of diseases selected from the group consisting of Pemphigus vulgaris, Bullous pemphigoid, Goodpasture's syndrome, autoimmune haemolytic anemia (AIHA), rheumatoid arthritis, Systemic Lupus erythematosus, Grave's disease (autoimmune hyperthyroidism), contact dermatitis, Myastenia gravis, juvenile diabetes, Sjögren's syndrome, autoimmune throiditis, primary hypoadrenalism (Addison's disease), multiple sclerosis, thrombocytopenic purpura, pemphigous foliaceous, Morbus Wegener (granulomatosis) and celiac disease.

The present invention also provides for a method of therapy, amelioration and/or prevention of an autoimmune disease comprising the administration to a subject in need of such therapy and/or prevention an effective amount of at least one (poly)peptide construct as defined herein, of at least one polynucleotide as defined herein, of at least one vector defined herein or of at least one host of described herein. It is particularly preferred that said method be employed for the treatment and/or prevention of autoimmune disorders as described herein, like, but not limited to, *Pemphigus vulgaris, Bullous pemphigoid*, Goodpasture's syndrome, autoimmune haemolytic anemia (AIHA), rheumatoid arthritis, Systemic Lupus erythematosuas, Grave's disease (autoimmune hyperthyroidism), contact dermatitis, Myastenia gravis, juvenile diabetes, Sjobgren's syndrome, autoimmune throiditis, primary hypoadrenalism (Addison's disease), multiple sclerosis thrombocytopenic purpura, pemphigous foliaceous, Morbus Wegener (granulomatosis) and celiac disease. It is particularly preferred that the subject to be treated by the method of the invention be a human subject.

The compositions, in particular the pharmaceutical compositions, uses and methods of the invention can be used for all kinds of diseases hitherto unknown as being related to or dependent on auto-antigens and/or the production of auto-antibodies. Said compositions, uses and methods of the invention may be desirably employed in humans, although animal treatment is also encompassed by the uses and methods described herein.

In accordance with this invention, the terms "treatment", "treating" and the like are used herein to generally mean obtaining a desired pharmacolocical and/or physiological effect. Said effect may be prophylactic in terms of completely or partially preventing a disease, in particular, an autoimmune disease, or a symptom thereof and/or may be therapeutic in terms of completely or partially curing a disease, in particular, an autoimmune disease, and/or (an) adverse effect(s) attributed to said disease. The term "treatment" as used herein includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

(A) Binding of MOG-Fc to B cells of anti-MOG transgenic mice. Splenocytes from wt (upper panel) and anti-MOG transgenic mice (lower panel) were prepared and incubated with MOG-Fc. MOG-Fc bound to IgM-positive cells was detected by FITC-labeled human Fcγ-specific antibody.

(B, C) Binding of MOG-Fc to Mac1- and CD5-positive mouse splenocytes. Single-cell suspensions of wt splenocytes were prepared. Cells were incubated with 50 µg/ml MOG-Fc protein (lower panel) or PBS (upper panel). Cell-bound MOG-Fc was detected with biotinylated, monoclonal anti-MOG antibody 8.18-C5, followed by counterstaining with streptavidin-FITC, and Mac1-phycoerythrin (PE) or CD5-PE.

(D) Binding of MOG-Fc to a murine macrophage cell line. The monocyte/macrophage cell line p388.D1 expressing murine Fc receptors was incubated with MOG-Fc. Bound MOG-Fc was detected via FITC-labeled anti-human Fcγ antibody by flow cytometry (left panel). Binding was quantitated and expressed as mean fluorescence intensity (MFI) (right panel).

FIG. 15. Specificity of MOG-Fc mediated cytotoxicity

A) Effect of non-specific human IgG1.

8.18-C5 target cells were incubated with human PBMCs and 10 µg/ml MOG-Fc protein in RPMI/10% FCS. Incubation was performed for 16 h at 37° C. and 5% $CO_2$. After incubation, target cells were labeled with anti-murine IgG1 antibody (mIgG) and analyzed for viability through propidium iodide (PI) staining. Column 1: incubation of PBMCs and target cells in the absence of isotype control and MOG-Fc. Column 2: the effect of a recombinant human IgG1 (isotype control). Column 3: the effect of MOG-Fc under identical assay conditions.

B) Effect of murine cell line expressing cell surface IgG1 of non-MOG specificity. Mouse B cell line TIB-208 is expressing cell surface IgG1 of non-MOG specificity. Column 1: unspecific lysis of TIB-208 cells in the presence of human PBMC. Column 2: the effect of MOG-Fc (10 µg/ml) on the viability of TIB-208 cells. Column 3: the effect of MOG-Fc (10 µg/ml) on hybridoma line 8.18-C5 under identical assay conditions. Error bars indicate S.D. values of triplicates.

Figure 16:
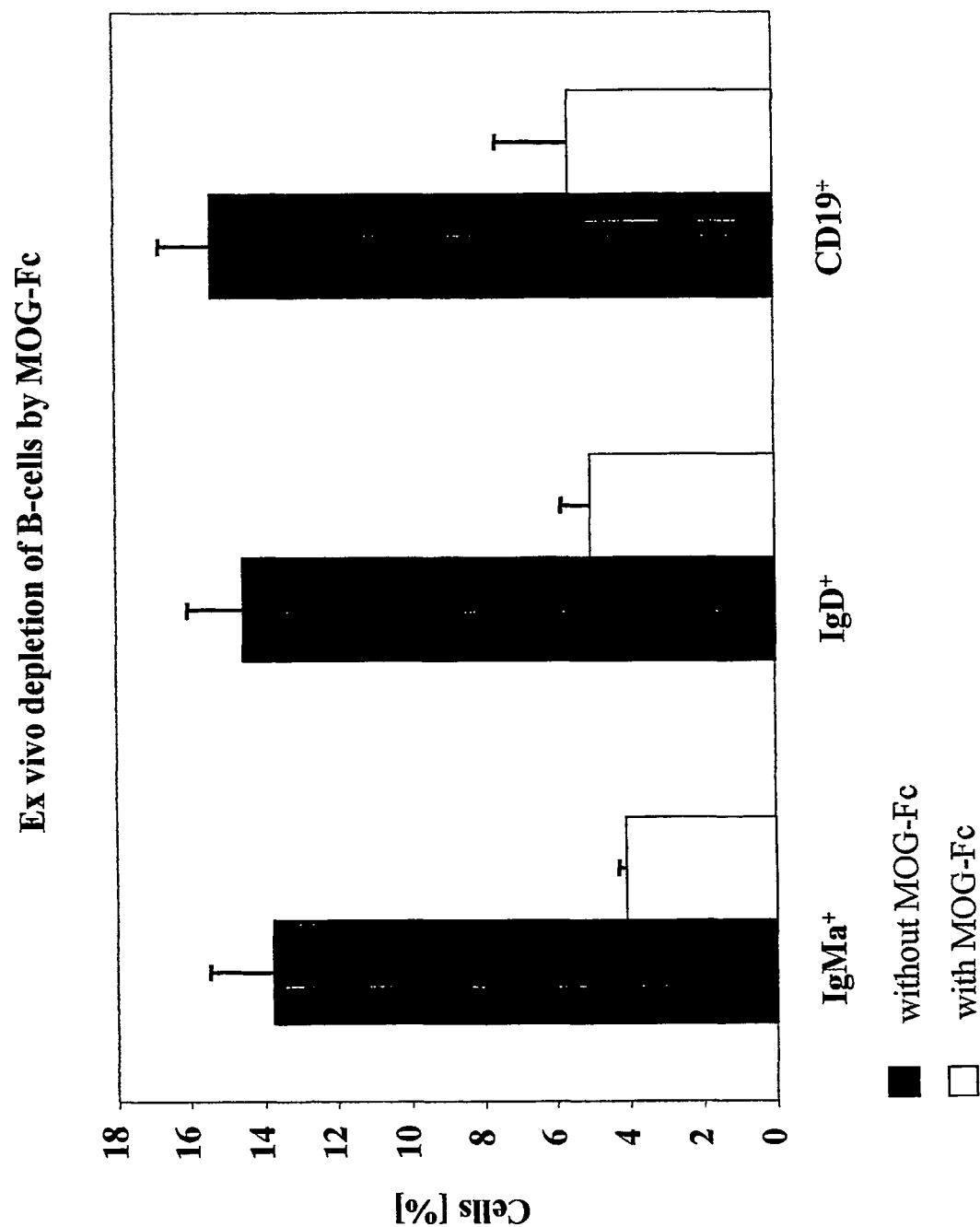

FIG. 16. Ex vivo depletion of B-cells from anti-MOG transgenic mice.

Single cell suspensions of spleens from anti-MOG transgenic mice were prepared. Splenocytes were cultured in the absence (dark columns) or presence (white columns) of MOG-Fc (10 µg/ml). After incubation, the B cell population was analyzed by flow cytometry using antibodies against the B cell markers IgM, IgD and CD19. The frequency of cell populations is expressed as percentage of total live cells within the lymphocyte gate. Error bars represent S.D. values of triplicates.

FIG. 17. In vivo depletion of MOG-reactive B cells by MOG-Fc.

Anti-MOG transgenic mice were left untreated (control) or treated i.p. with 100 µg of MOG-Fc protein on days 1 and 3.

(A) Flow cytometric analysis of B cells from MOG-Fc-treated anti-MOG transgenic mice.

Upper panel, the effect of MOG-Fc on IgM$^a$ (allotype a)-positive, rMOG-reactive B cells. Lower panel, analysis of MOG-Fc binding to B220-positive B cells as detected by an anti-human Fcγ antibody. Peripheral blood lymphocytes (PBLs) were prepared 1 day post-treatment and the MOG$^{high}$ B-cell population was analyzed as indicated. Five MOG-Fc-treated and three control animals were analyzed. Representative results are shown.

(B) The effect of MOG-Fc on the MOG$^{high}$ B-cell population in anti-MOG transgenic mice.

FACS data from five animals were quantitated and were shown as percentage of total B220$^+$ cells. Bars give S.D. values.

Figure 18A:
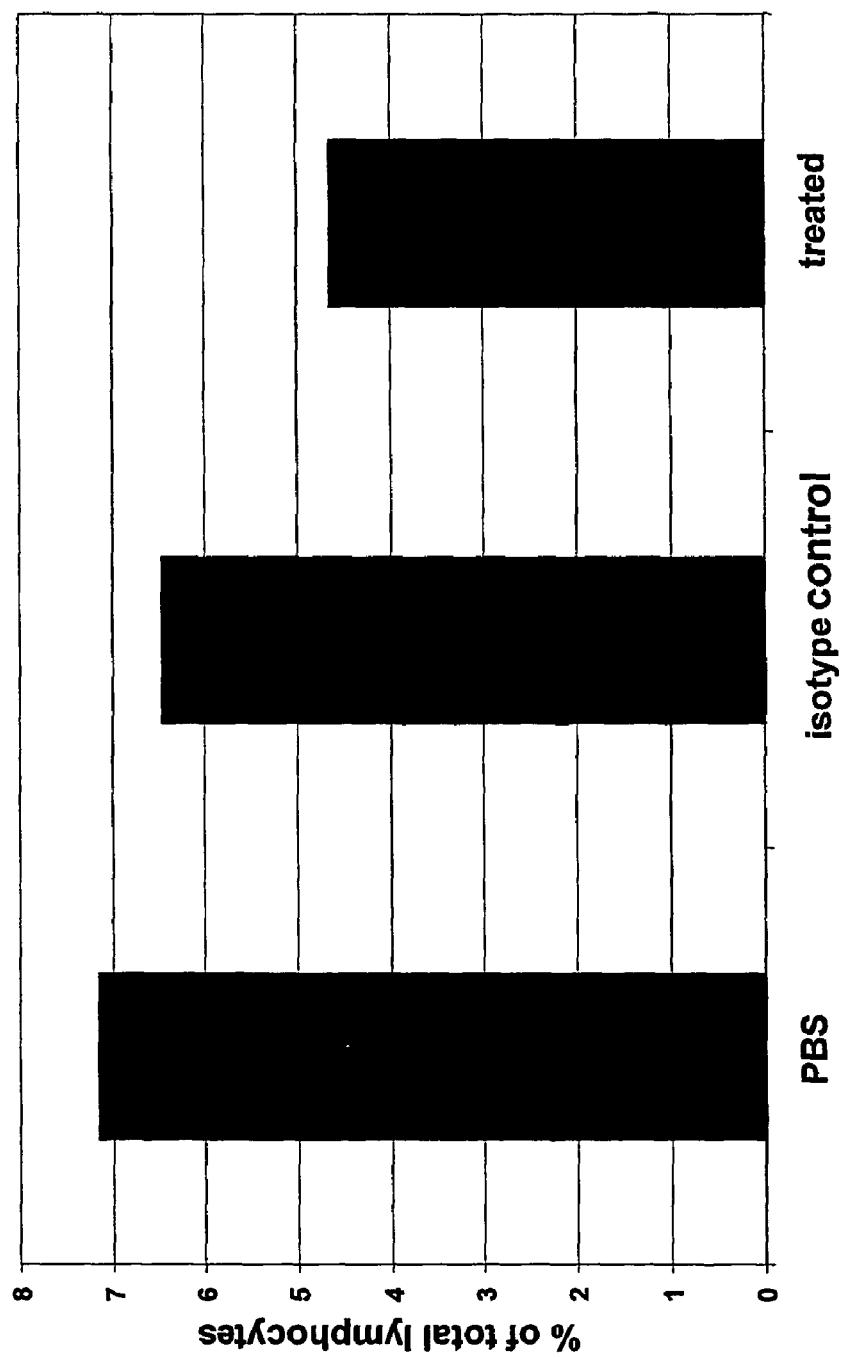

FIG. 18 In vivo depletion of anti-MOG reactive B cells in wildtype mice after cellular transfer 1.5×10$^7$ B cells derived from anti-MOG transgenic mice with BL/6 background were transferred intraveniously into wt BL/6. Mice were divided into 3 groups (N=5 per group) and treated with treated with MOG-Fc (100 µg each treatment) intraperitoneally 1, 2 and 3 days post-transfer (treated), with human IgG1 isotype (isotype control) and PBS (PBS).

24 h (A) and 72 h (B) after the last treatment, peripheral blood was collected by tail bleeding and analyzed for anti-MOG reactive B cells via FACS staining using recombinant MOG-Fc and PE-conjugated anti-human Fc antibody (ICN).

Figure 18B:
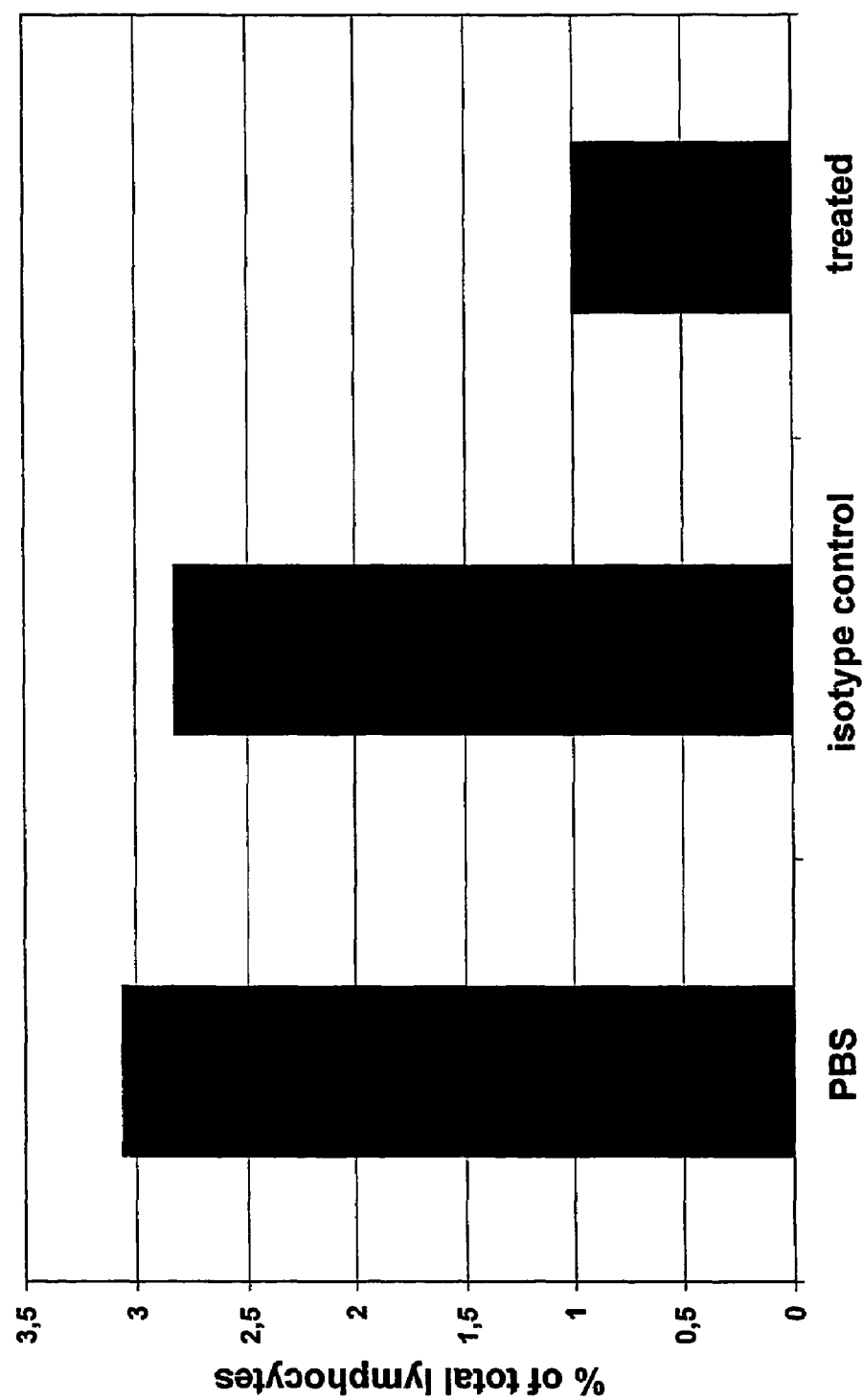

One day post-treatment with MOG-Fc depletion of MOG-reactive B cells (FIG. 18A) was observed. This effect was more prominent three days post-treatment showing a depletion af autoreactive B-cells in the order of 70% (FIG. 18B).

Figure 19A:
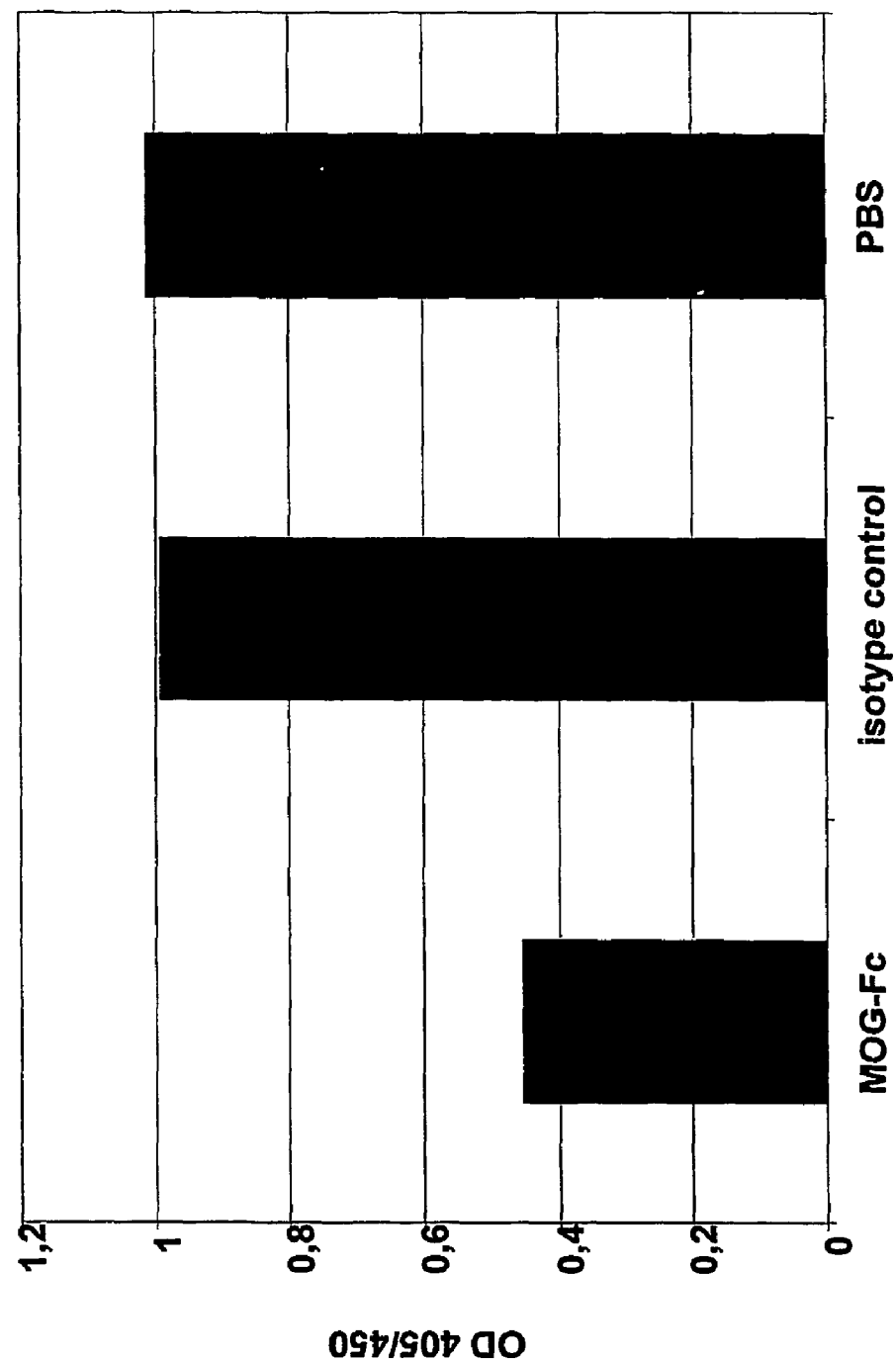
Figure 19B:
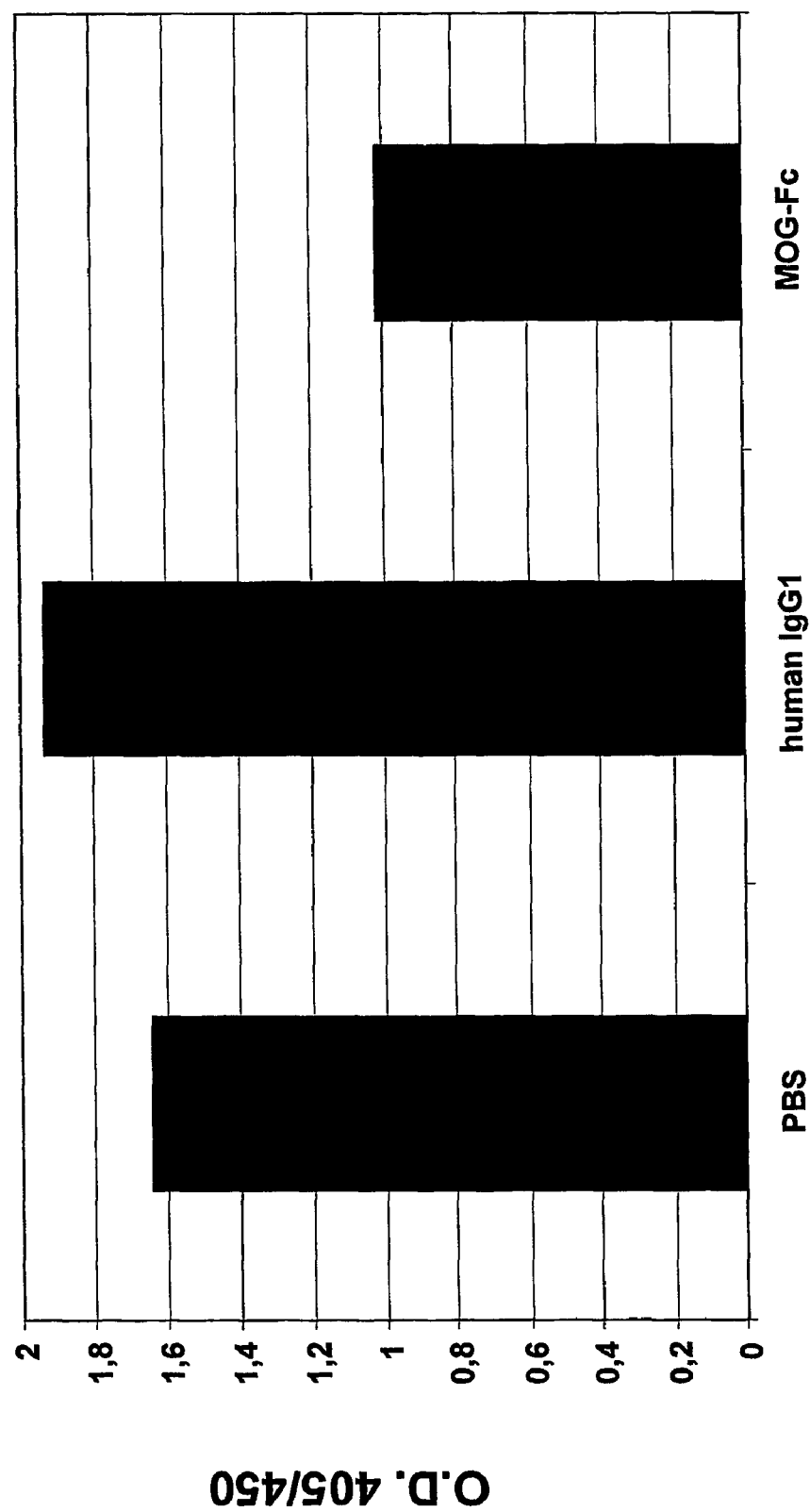

FIG. 19 Reduction of MOG-specific IgG in wildtype mice after cellular transfer 1.5×10$^7$ B cells derived from anti-MOG transgenic mice with BL/6 background were transferred intraveniously into wildtype BL/6. Mice were divided into 3 groups (N=5 per group) and treated with MOG-Fc, human IgG1 isotype control and PBS. Peripheral blood was collected by tail bleeding 24 h (FIG. 19A) and 72 h (FIG. 19B) post-treatment and serum was analyzed for anti-MOG specific IgG titers by ELISA.

BRIEF DESCRIPTION OF THE INVENTION

The present invention is additionally described by way of the following illustrative non-limiting examples, that provide a better understanding of the present invention and of its many advantages.

EXAMPLE 1

Expression Vectors for Autoantigen Fragment—αCD3 and -Fc Fusion Proteins

Expression of the construct of interest is driven by the promotor of the human elongation factor alpha (Kufer; PNAS 92 (1995): 7021). This promotor is known to be very efficient in virtually all eukaryotic cells, thereby making this expression system a powerful tool for high protein expression without limitations regarding the selected eukaryotic host cell line. A versatile multiple cloning site (MCS) facilitates the cloning of the construct. The expression of the construct of interest is linked to the expression of the selection marker dihydrofolate reductase (DHFR) via the internal ribosomal entry site (IRES). This arrangement assures that almost all stably transfected cells will express the construct, as both genes depend on the promotor of EFα. A strong polyadenylation signal for both genes is provided by the SV40 polyadenylation site, and the pUC18 backbone of the plasmid provides a well-characterized plasmid backbone with ampicillin resistance for bacterial selection.

EXAMPLE 2

Construction of an Exemplified Antigenxeffector Molecule; An Auto-antigen x αCD3 Fusion Protein: MOGxCD3

Figure 2:
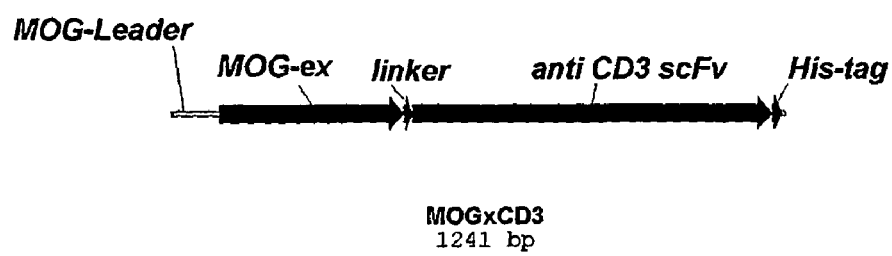
FIG. 2. Schematic representation of autoantigen—effector domain molecules. A. MOGxCD3 arrangement. B. MOG-Fc arrangement.
Figure 2:
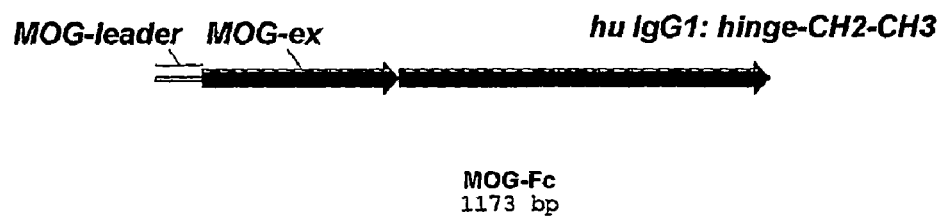

The expression vector pEF-dhfr CD19xCD3 (Löffler; Blood 95 (2000): 2098) was used as the basis for the construction of MOGxCD3 by removing the region coding for the single-chain αCD19 antibody. As described below, the remaining αCD3 expression cassette was used for insertion of cDNA coding for the auto-antigenic domain of the human MOG protein and provides an ideal system for further cloning of auto-antigen x αCD3 fusion proteins (FIG. 2A).

2.1. Isolation of RNA from MOG-transfected Fibroblasts and cDNA Synthesis

Total RNA was isolated from MOG-transfected fibroblasts (Schluesener, J. Immunol. 139 (1987), 4016-4021) using the Qiagen RNEasy RNA Extraction Kit according to the manufacturer's suggestions. RNA was dissolved in H$_2$O and stored at −80° C. cDNA was synthesized as follows: 2 µg total RNA were added to 0.5 µg Oligo-dT primer in a total reaction volume of 12 µl. The reaction mixture was incubated at 70° C. for 10 min. Then, 4 µl 5× First Strand Buffer (Gibco BRL), 2 µl 0.1M DTT and 1 µl 10 mM dNTPs were added. Incubation was performed at 42° C. for 2 min, after which 200 U of Superscript II Reverse Transcriptase (RT) (Gibco BRL) were added. The reaction mixture was incubated for 50 min. at 42° C. Then, RT was inactivated due to a 15 min incubation step at 70° C. Isolated cDNA was stored at −20° C.

2.2. Amplification of MOG-coding cDNA Fragments

The following primers were chosen to obtain the cDNA coding for the extracellular domain of the human MOG protein (MOG-ex):

```
Primer 1 (MOG-Ex 5'): 5'-TAGAATTCATGGCAAGCTTATCGAGACCC-3'  (Seq ID No 5)

Primer 2 (MOG-Ex 3'): 5'-CATCCGGATCCAGGGCTCACCCAGTAGA-3'  (Seq ID No 6)
```

Primers were designed to amplify the first 462 bases of the coding region for the leader sequence and extracellular domain of the human MOG protein. The primers contained EcoRI and BspEI restriction sites at 5' and 3' ends, respectively. Polymerase chain reactions (PCR) conditions were: 50 pmol primer, 1 μl dNTPs 10 mM, 4 μl cDNA, 5 μl Pfu-buffer 5× (Stratagene) and 5 U Pfu-Polymerase (Stratagene) in a final volume of 50 μl. The final product of 474 bp was verified on a ethidium bromide stained 2% agarose gel.

2.3 Construction of MOGxCD3 Fusion Protein

The expression vector CD19xCD3 pEF-dhfr was digested with EcoRI and BspEI, leading to removal of the fragment coding for the anti-CD19 scFv domain. The remaining vector-anti CD3 scFv portion was gel-extracted (gel extraction kit, Qiagen). Equally, MOG-ex was partially digested with BsaWI and EcoRI, and the corresponding fragment of 474 bp of length isolated via gel-extraction. BsaWI restriction was chosen due to this enzyme's insensitivity to dam-methylation at the original BspEI restriction site. DNA was eluted in 30 μl Tris pH 8.5 and stored at −20° C. Ligation of isolated DNA fragments was performed with equal volumes of extracted DNA and 5 U of T4 DNA Ligase in a total volume of 20 μl in 1× T4 buffer (Roche Biochemicals) for 30 min. at room temperature (RT). Of each ligation reaction, 3 μl were used to transform *E. coli* XL-1 Blue as described above. Colonies were picked and subjected to MiniPrep analysis. Following analytical restriction enzyme digestion, appropriate clones were sequenced (Sequiserve, Munich). Clones were grown in 300 ml LB-Amp medium, and plasmid DNA was isolated using the Qiagen plasmid prep kit. Corresponding nucleotide and amino acid sequences of this construct are depicted and illustrated in SEQ ID NOs: 1 and 2.

EXAMPLE 3

Construction of Auto-antigen—Fc Fusion Protein: MOG-Fc

3.1. Isolation of RNA from HD69-transfected CHO Cells and cDNA Synthesis.

Total RNA was isolated from HD69-transfected CHO cells (W09846645) using the Qiagen RNEasy RNA Extraction Kit according to the manufacturer's suggestions. RNA was dissolved in H2O and stored at −80° C. Complementary DNA synthesis was performed: briefly, 2 μg total RNA were added to 0.5 μg Oligo-dT primer in a total reaction volume of 12 μl. The reaction mixture was incubated at 70° C. for 10 min. Then, 4 μl 5x First Strand Buffer (Gibco BRL), 2 μl 0.1M DTT and 1 μl 10 mM dNTPs were added. Incubation was performed at 42° C. for 2 min, after which 200 U of Superscript II Reverse Transcriptase (RT) (Gibco BRL) were added. The reaction mixture was incubated for 50 min. at 42° C. Then, RT was inactivated due to a 15 min incubation step at 70° C. Isolated cDNA was stored at −20° C.

3.2. Amplification of IgG1-coding cDNA Fragments

```
In order to obtain cDNA coding for the Fc-domain of the human
IgG1 antibody backbone, the following primers were chosen:
Primer 3 (IgG1-Fc 5'): 5'-TATCCGGAGAGCCCACCTCTTGTGACAAAAC-3'      (Seq ID No 7)

Primer 4 (IgG1-Fc 3'): 5'-GTGTCGACTCATTTACCCGGAGACAGGG-3'        (Seq ID No 8)

Yet, an even more preferred primer (IgG1-Fc5') is the following:
Primer 5 (IgG1-Fc5'): 5'-TATCCGGAGAGCCCAAATCTTGTGACAAAAC-3'      (SEQ ID NO: 9)
```

Primers were designed to amplify the 699 bases coding for the Fc part of the human IgG1 backbone, while introducing BspEI and SalI restriction sites at 5' and 3' ends of the amplified fragment, respectively. Amplification was performed according to standard PCR protocols. Briefly, 50 pmol/each of appropriate primer, 1 μl dNTPs 10 mM, 4 μl cDNA, 5 μl Pfu-buffer 5x (Stratagene) and 5 U Pfu-Polymerase (Stratagene) were added to a final volume of 50 μl in H2O. The final product, containing the flanking restriction sites, was 711 bp in length.

DNA was recovered from PCR reaction mixture according to the manufacturer's suggestions (Boehringer High Pure PCR Product Purification Kit, cat. no. 1 732 676). Blunt-ended PCR products generated by Pfu DNA polymerase were ligated into pCR-script vector (Stratagene #211188) according to manufacturer's protocol (Stratagene). Plasmids were transformed into competent *E. coli* strain XL-1 Blue using 4 μl of ligation product added to 50 μl of *E. coli*. The mixture was incubated on ice for 10 min., 1 min. at 42° C., and then again on ice for 2 min. Thereafter, 150 μl LB-medium were added and expression of ampicillin resistance genes was induced due to 45 min at 37° C. while shaking. Reaction mixtures were plated on LB-Amp Agarose plates (50 μg ampicillin/ml) and incubated at 37° C. for 16 h. Colonies were picked and grown in LB-Amp medium (100 μg/ml) for 8-12 h. Bacteria were spun down, and plasmid DNA was isolated according to manufacturer's suggestions (Plasmid Mini-Kit, Qiagen). DNA was subjected to restriction enzyme analysis, and suitable clones were sequenced (SequiServe, Munich). Correct clones were grown in 300 ml LB-Amp medium, and plasmid DNA was isolated according to manufacturer's instructions (PLasmid Maxi Kit, Qiagen).

3.3. Construction of MOG-Fc Fusion Protein

In order to obtain the desired construct (FIG. 2B), expression vector CD19xCD3 pEF-dhfr was subjected to restriction with EcoRI and SaII, leading to removal of the fragment coding for CD19xCD3. The remaining linearized vector was gel-extracted (gel extraction kit, Qiagen). Equally, MOG-ex was partially digested with BsaWI and EcoRI, and the corresponding fragment of 474 bp of length was isolated via gel-extraction as described above. BsaWI restriction was chosen due to this enzyme's insensitivity to dam-methylation at the original BspEI restriction site. DNA was eluted in 30 µl Tris pH 8.5 and stored at −20° C. Ligation of isolated DNA fragments was performed with equal volumes of extracted DNA and 5 U of T4 DNA Ligase in a total volume of 20 µl in 1×T4 buffer (Roche Biochemicals). Ligation was allowed to proceed for 30 min. at room temperature (RT). Of each ligation reaction, 3 µl were used to transform E. coli XL-1 Blue as described above. Colonies were picked and subjected to MiniPrep analysis. Following analytical restriction enzyme digestion, appropriate clones were sequenced (Sequiserve, Munich). Correct clones were grown in 300 ml LB-Amp medium, and plasmid DNA was isolated using the Qiagen plasmid prep kit as described above.

The corresponding nucleotide and amino acid sequences of this specific, illustrative construct are depicted in SEQ ID NOs: 3 and 4, respectively.

EXAMPLE 4

Expression and Purification of MOGxCD3 Fusion Protein 4.1. Stable Transfection of CHO Cells CHO cells were plated at 3*10$^5$/well in tissue culture 6-well plates and incubated at 37° C. overnight. 3 µg of DNA were pipetted in sterile Eppendorf tubes, supplemented with 100 µl MEM-α medium (Gibco BRL) and 10 µl SuperFect transfection reagent (Qiagen) and incubated for 10 min. at RT. 600 µl of MEM-α medium were added, and the reaction mixture was transferred to CHO cells. Following a 2 h-incubation at 37° C., the supernatant was aspirated, cells were washed once with PBS, and 2 ml MEM-α medium (10% FCS, HT-supplement 1:100) were added to each well. Transfection efficiency was determined to be 10% via standard β-galactosidase control transfection. After 24 h at 37° C., transfected cells were transferred to 10 ml cell culture bottles (Nunclone Δ, Nalge Nunc International) and selected for expression of the dhfr vector via growth in non-supplemented MEM-α medium plus 10% dialysed FCS. Following 2 passages of confluent cells at 1:5 splitting ratios, transfectants were further selected by addition of 20 nM methotrexate (MTX) to the selection medium. Cells were passaged 3 times, whereafter MTX concentration was increased to 100 nM. Following a further 3 passages, MTX was added to a final concentration of 500 nM.

4.2. Purification of Expressed MOGxCD3 Fusion Protein

Stably transfected CHO-cells were transferred to 500 ml roller-bottles (Nalge Nunc International) in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotana 46 centrifuge, and recombinant protein was purified from cell culture supernatant in a three-step purification process including cation exchange chromatography, immobilized metal affinity chromatography (IMAC) and gel filtration. GradiFrac System (Pharmacia) was used for chromatography. All chemicals were of research grade and purchased from Sigma (Deisenhofen) or Merck (Darmstadt).

Cation exchange was performed on a HiTrap SP Sepharose column (Pharmacia) that was equilibrated with buffer A1 (20 mM MES pH 5.5). Cell culture supernatant was diluted 2:1 with buffer A1 and applied to the column (10 ml) with a flow rate of 4 ml/min. Unbound sample was washed out with buffer A1 and the bound protein was eluted with 100% buffer B1 (20 mM MES pH 5.5, 1M NaCl). Eluted protein fractions were pooled for further purification.

IMAC was performed, using a HisTrap column (Pharmacia) that was loaded with NiSO4 according to the manufacturer's protocol. The column was equilibrated with buffer A2 (20 mM NaPP pH 7.5, 0.4 M NaCl), and the sample was diluted 2:1 with buffer A2 to obtain a pH of 7. The sample was applied to the column (2 ml) with a flow rate of 1 ml/min and the column was washed with buffer A2 to remove unbound sample. Bound protein was eluted using a linear gradient of buffer B2 (20 mM NaPP pH 7.5, 0.4 M NaCl, 0.5 M Imidazol) (0-100% buffer B2 in 10 column volumes). Eluted protein fractions were pooled for further purification.

Gel filtration chromatography was performed on a Sephadex S200 HiPrep column (Pharmacia) equilibrated with PBS (Gibco). Eluted protein samples (flow rate 1 ml/min) were subjected to SDS-Page and western blotting for MOGxCD3 detection. The column was previously calibrated for molecular weight determination (molecular weight marker kit, Sigma MW GF-200).

Protein concentrations were determined using protein assay dye concentrate (BioRad) and IgG (Biorad) as standard protein.

Figure 3:
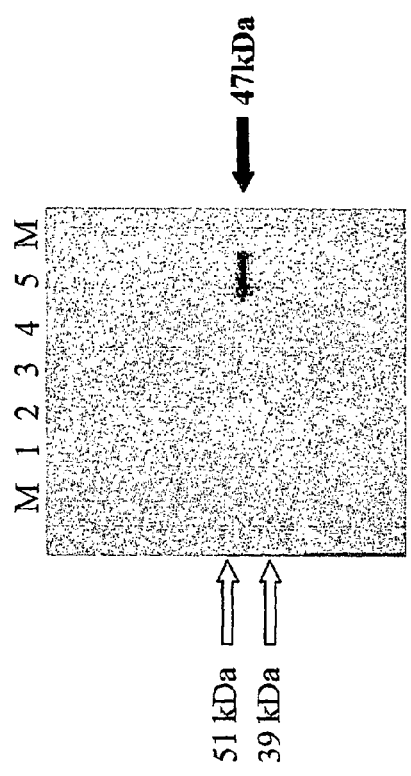
FIG. 3. Expression and purification of MOGxCD3. MOGxCD3 was expressed in CHO cells and purified by cation exchange, followed by nickel chelate chromatography and gel filtration. (A) 5 Gel filtration peaks are shown, separated by SDS-PAGE and analyzed by Coomassie-blue staining. Peak number 5 contains monomeric MOGxCD3 protein of a molecular weight of approximately 47 kDa. (B) Gel filtration peaks were separated on SDS-PAGE identical to A, transferred to a nitrocellulose membrane and incubated with an anti-MOG antibody (8.18-C5). Only peak 5 containing the 47 kDa monomeric MOGxCD3 reacts with monoclonal anti-MOG antibody (8.18-C5). Higher molecular weight bands present in peaks 1 to 4 are not recognized by anti-MOG antibody.
Figure 3:
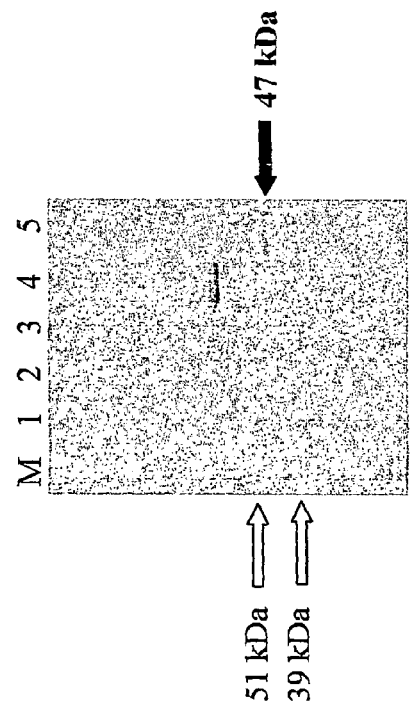

SDS-PAGE under non-reducing conditions was performed with precast 4-12% Bis-Tris gels (NOVEX). Sample preparation and application were according to the manufacturer's protocol. The molecular weight was determined with SeeBlue protein standard (NOVEX). The gel was stained with colloidal Coomassie (NOVEX protocol; FIG. 3A).

4.3. Western Blot

Fractions were analyzed by Western Blot and staining with anti-MOG antibody for the presence of MOGxCD3. Protein was blottet to reinforced nitrocellulose membrane (Optitran BA-S 83, Schleicher & Schuell) at 200 mA for 1 h (blotting buffer: 48 mM Tris, 39 mM Glycin, 0.01% SDS). Recombinant fusion protein was detected with anti-MOG monoclonal antibody (8.18C5) at 5 µg/ml in PBS; bound anti-MOG ab was detected via anti-mouse IgG antibody, AP-conjugated at 1:10000 in PBS (Sigma A-2429). The membrane was stained with BCIP/NBT (Sigma B-5655). (FIG. 3B).

The purity of the isolated protein was >95% as determined by SDS-PAGE. The molecule had an apparent mass of 45 kDa consistent with the predicted size. The final yield of purified protein was ca. 2.4 mg/l cell culture supernatant. The final product ran as an approximately 45 kDa protein under native conditions as determined by gel filtration in PBS. No higher molecular weight forms were detected, suggesting that MOGxCD3 is a monomer (see FIG. 3B).

EXAMPLE 5

Expression and Purification of MOG-Fc Fusion Protein 5.1. CHO Cells were Transfected as Described in Example 4.

Figure 4:
FIG. 4. Expression and purification of MOG-Fc fusion protein. MOG-Fc fusion protein was expressed in CHO cells and purified by affinity chromatography using Protein A sepharose. Purified protein was separated by SDS-PAGE and analyzed by coomassie-blue staining (A) in the presence of the reducing agent DTT, or by Western blotting on nitrocellulose (B), followed by detection using a monoclonal antibody against MOG (8.18-C5). As expected, MOG-Fc fusion protein has a molecular weight of approximately 50 kDa under reducing conditions (+DTT), but runs at a molecular weight of approximately 115 kDa in the absence of DTT (−DTT), indicative for a dimer under non-reducing conditions. Detection in (B) was with an anti-Fc monoclonal antibody.

Stably transfected CHO-cells were transferred to 500 ml roller-bottles (Nalge Nunc International) in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotanta 46 centrifuge, and recombinant protein was purified using a 1-step purification procedure via Protein A affinity chromatography (HiTrap Protein A column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound Protein was eluted with 20 mM citrate, pH 3, using a linear gradient. Fusion protein yield amounted to 10 mg/l. Protein was >95% pure as assessed by Coomassie staining (FIG. 4A).

5.2. Protein Analysis MOG-Fc

MOG-Fc fusion protein was analyzed via SDS-PAGE as described for MOGxCD3. Coomassie Brilliant Blue staining under reducing conditions (FIG. 4A) revealed a major band at 50 kDa, with a higher molecular weight lane at approximately 115 kDa. Western blotting under reducing and non-reducing conditions was performed for further analysis (FIG. 4B); under reducing conditions (FIG. 4B, +DTT), MOG-Fc runs as a monomer of 50 kDa, which corresponds to its predicted size. The native protein has a molecular mass of approximately 115 kDa (FIG. 4B, –DTT) under non-reducing conditions. This suggests that MOG-Fc is a disulfide-bridge linked dimer in its native state, presumably cross-linked via two cysteine residues in the hinge-region of the human IgG1 part of the protein.

EXAMPLE 6

Binding of Auto-antigen Fusion Proteins to Autoreactive B-cells 6.1. Source and Isolation of Autoreactive B-cells Litzenburger et al., J. Exp. Med. 188 (1) (1998) 169-180) generated a transgenic mouse strain with an anti-MOG heavy chain variable region, derived from the anti-MOG mAb 8.18-C5 "knocked in" for the germline $J_H$ locus. Such mice exclusively express the 8.18-C5 anti-MOG heavy chain, resulting in generation of approximately 30% MOG-reactivity in the B-cell pool, as assessed by binding to recombinant MOG. Whole lymphocytes from transgenic knock-in mice were prepared from spleen as described elsewhere (Iglesias J. Exp. Med. 188 (1): 169-180). Resting B-lymphocytes (CD43-) were isolated from whole lymphocyte preparations. Cells were suspended in 5 ml PBS, 1% BSA, and 150 µl biotinylated anti-CD43 ab (Pharmingen) were added. After 30 min. on ice, cells were washed twice with PBS/1% BSA, and streptavidin-conjugated Dynabeads were added to obtain a mean 3.3 beads/cell. The mixture was incubated at 4° C. for 30 min. while rotating, whereafter bound cells were separated magnetically.

Figure 6:
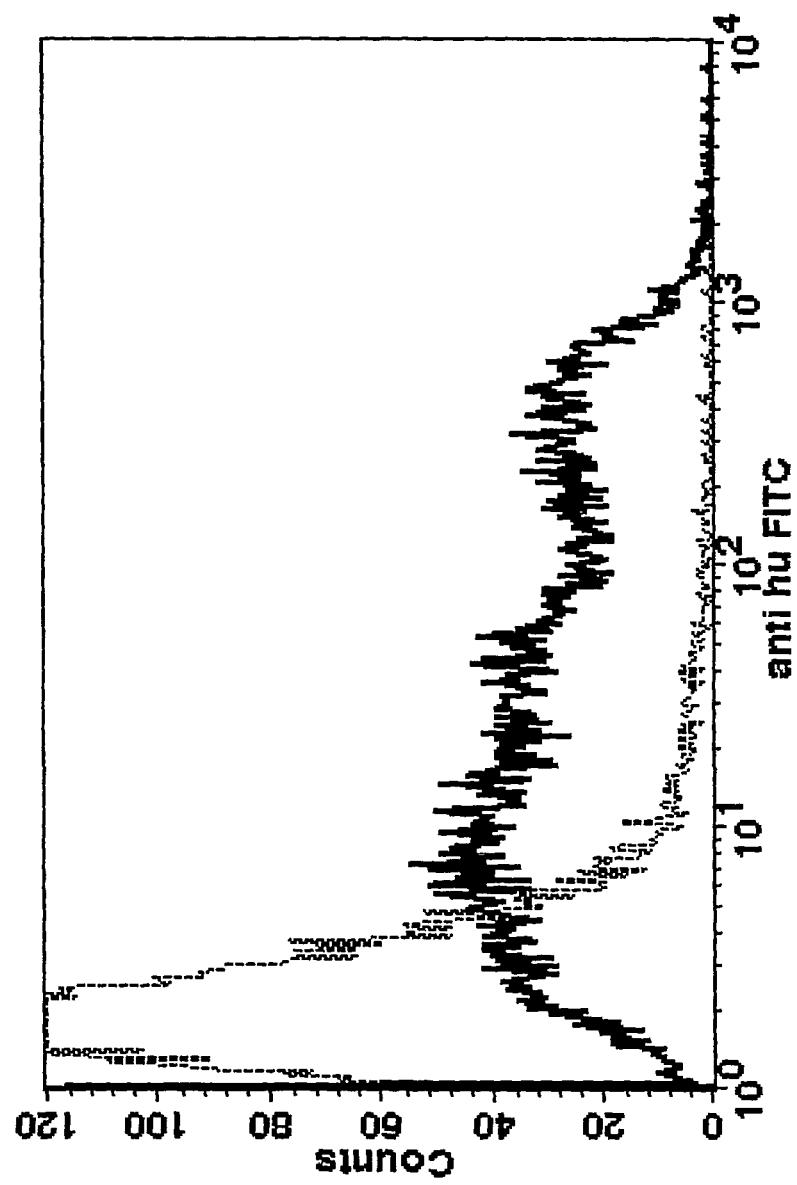
FIG. 6. Binding of MOG-Fc fusion protein to B-cells of a transg nic mouse. Resting B-lymphocytes (CD43⁻) were isolated and incubated with MOG-Fc. Bound fusion protein was detected by a FITC-labeled anti-human Fc-specific antibody. Only a subpopulation of transgenic B-cells express MOG-reactive B-cell receptors.
Figure 7:
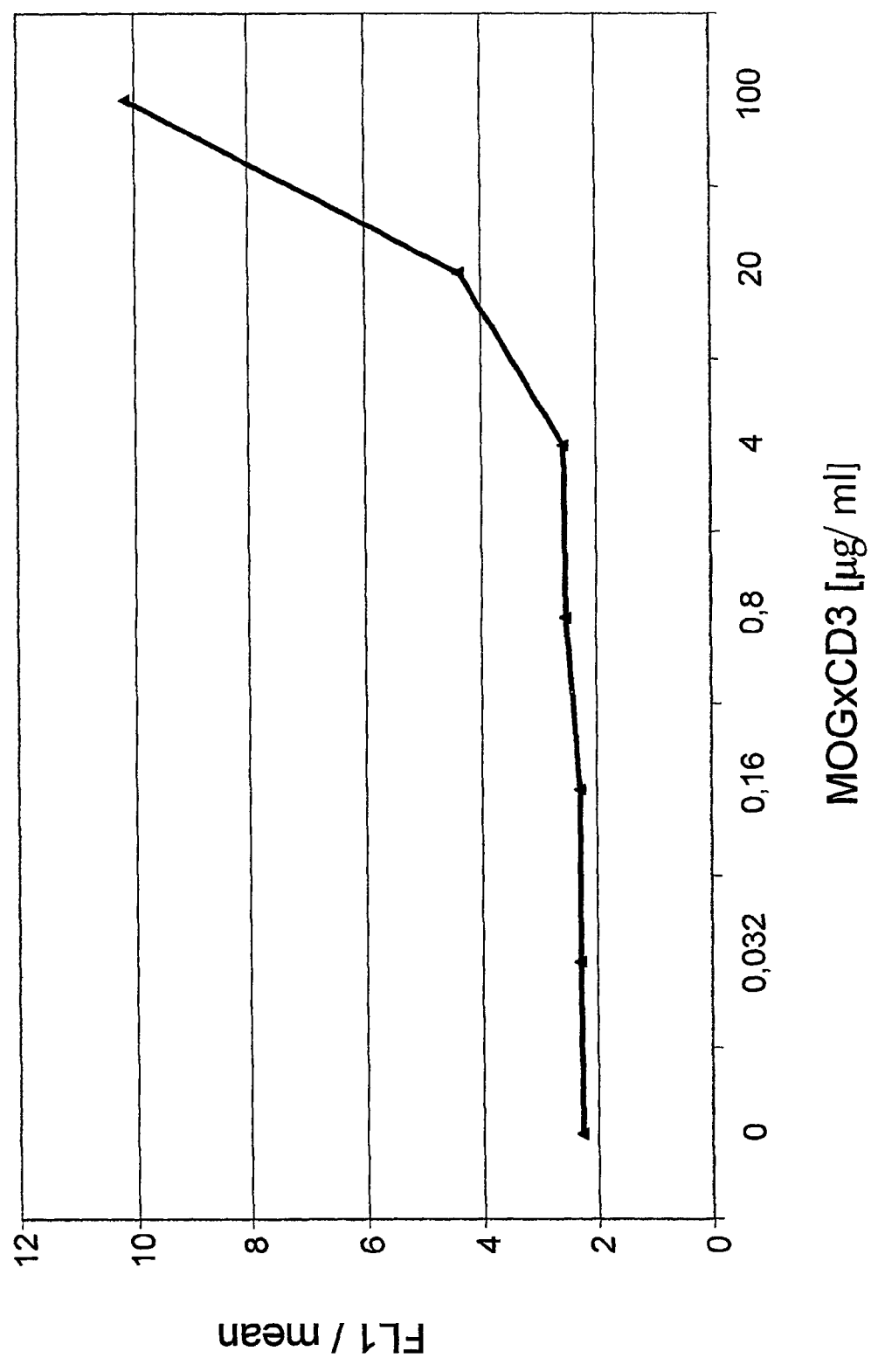
FIG. 7. Binding of MOGxCD3 to human T-cells. MOGxCD3 was incubated with human CD3-positive PBMCs, and bound fusion protein was detected with monoclonal anti-MOG antibody followed by FITC-labeled anti-mouse IgG1 antibody. Labeled cells were subjected to FACS analysis.

6.2. FACS-based Binding Assay of Auto-antigen Fusion Protein to Autoreactive B-cells Autoreactive B-cells were washed twice with FACS-buffer (PBS, 1% FCS, 0.05% NaN3). Cells were incubated with 50 gl fusion protein diluted to 1 and 10 µg/ml in FACS-buffer, respectively for 1 h at 4° C. Bound MOG-Fc fusion protein was detected with goat-α IgG FITC/hu, Fc-specific (ICN 67-217) at 1:50 (FIG. 6), while bound MOGxCD3 was detected with FITC-labeled a-HIS 6 antibody (Dianova; FIG. 7).

EXAMPLE 7

Binding of Auto-antigen Fusion Protein to Auto-antibody 7.1. Source of Auto-antibodies Hybridoma 8.18-C5 (Linington, MPI Neurobiology Martinsried) was cultivated in serum-free medium (Gibco). Cells were separated from supernatant by centrifugation, and mouse anti-MOG monoclonal IgG1 antibodies were purified using a 1-step purification procedure via Protein G affinity chromatography (HiTrap Protein G column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound Protein was eluted with 20 mM citrate, pH 3, using a linear gradient. Antibody yield amounted to 4.5 mg/l. Protein was >95% pure as assessed by Coomassie staining.

7.2. Sandwich-ELISA for Detection of MOG-Fc Fusion Protein

Isolated αMOG ab 8.18-C5 was used to detect purified MOG-Fc fusion protein and to verify existence of 1) functional extracellular domain of MOG protein and 2) Fc effector domain in the recombinant protein. MaxiSorp 96-well plates (Nalge Nunc International) were coated with αMOG at 5 µg/ml overnight at 4° C. Plates were blocked with 1% BSA for 1 h at RT, washed with PBS/0.05% Tween 20. Plates were incubated with various dilutions of MOG-Fc fusion protein in PBS for 1 h at RT, and bound fusion protein was detected using a-human IgG1 ab, Fc-specific and AP-conjugated (Sigma A-9544) at 1:10,000. Alkaline phosphatase-conjugated antibody was stained with pNPP (Sigma N-2770) and quantitated on the SpectraFluor ELISA reader (Tecan).

7.3. Sandwich-ELISA for Detection of MOGxCD3 Fusion Protein

Figure 5:
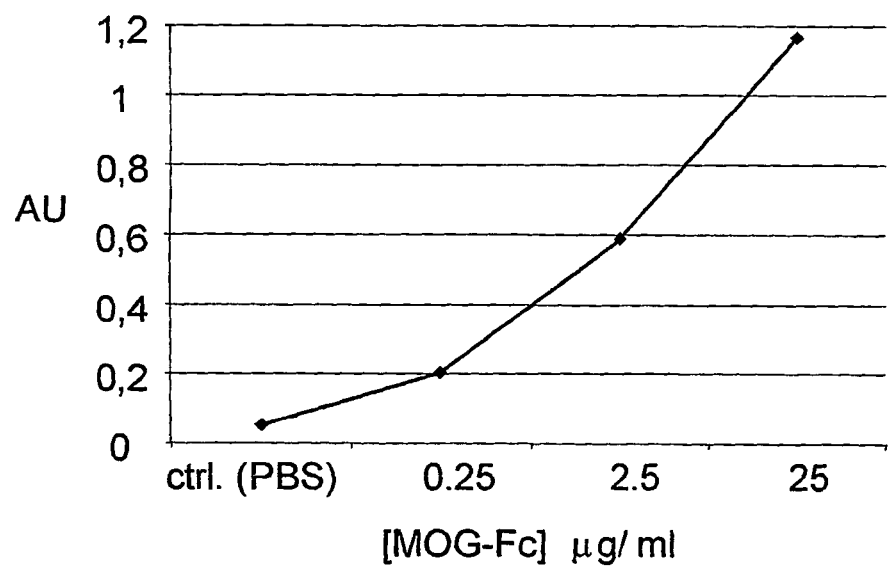
FIG. 5. Detection of MOG fusion protein in ELISA. ELISA plates were coated with anti-MOG antibody 8.18-C5 to capture the fusion proteins by their MOG domain. (A) Bound MOG-Fc fusion protein was detected with an AP-conjugated anti-human Fc antibody. (B) MOGxCD3 fusion protein was detected by an AP-labeled chicken versus singlechain Fv anti-CD3 polyclonal antibody.
Figure 5:
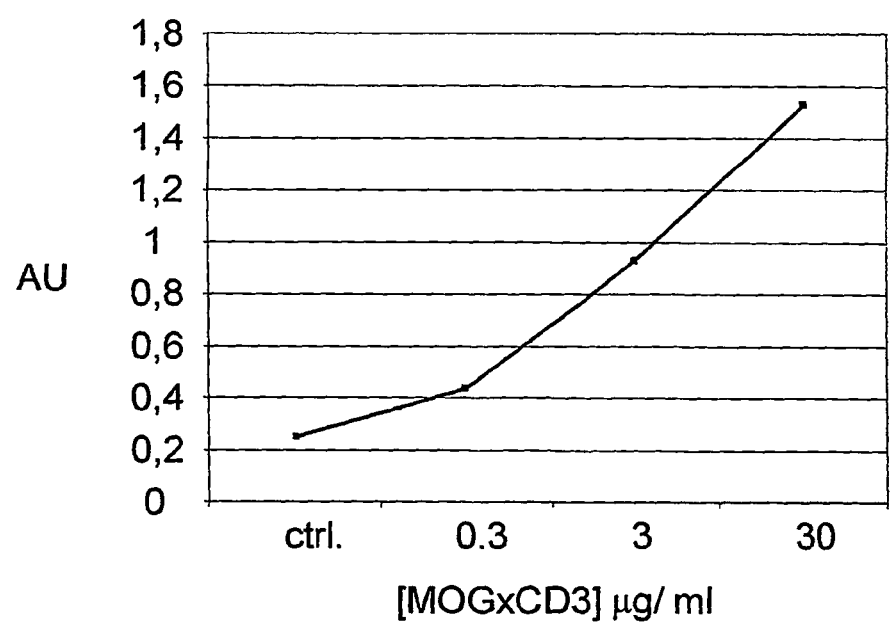

Isolated αMOG ab 8.18-C5 was used to detect purified MOGxCD3 fusion protein and to verify existence of 1) functional extracellular domain of MOG protein and 2) anti-CD3 effector domain in the recombinant protein. MaxiSorp 96-well plates (Nalge Nunc International) were coated with αMOG at 5 µg/ml overnight at 4° C. Plates were blocked with 1% BSA for 1 h at RT, washed with PBS/ 0.05% Tween 20. Plates were incubated with various dilutions of MOGxCD3 fusion protein in PBS for 1 h at RT, and bound fusion protein was detected using chicken polyclonal serum against scFv anti-CD3 (Davids Biotechnology). Bound chicken Ab was detected using alkaline phosphatase (AP)-coupled donkey-a-chicken ab at 1:10000 (Dianova 703-055-155). Alkaline phosphatase-conjugated antibody was stained with pNPP (Sigma N-2770) and quantified on the SpectraFluor ELISA reader (Tecan, FIG. 5B).

EXAMPLE 8

Binding of Auto-antigen Fusion Proteins to Immune Effector Cells 8.1. Isolation of PBMCs Buffy coats were diluted 1:2 in PBS and separated in Ficoll gradient of density 1.077 (Seromed Cat.No. L 6115). Lymphocytes were separated and washed twice with PBS. Erythrocytes were lysed with lysis buffer (8,29 g NH4Cl cell culture tested (Sigma A-0171), 1,0 g KHCO3 0,037 g EDTA, cell culture tested (Sigma E-6511);H2O add. 1L). Thrombocytes were separated during 20 min of centrifugation at 100×g. Remaining Lymphocytes were transferred to cell culture bottles and stored at 37° C./5% CO2.

8.2. Isolation of CD3+ Cells

Human T-cell enrichment columns (R&D Systems Cat. No. HTCC-500/525) were used for isolation of T-cells according to manufacturer's suggestions.

8.3. Binding Assay of MOGxCD3 to CD3+ PBMCs

To explore the binding of MOGxCD3 fusion protein to CD3+ cells, 200,000 CD3+ cells were added to each well of a V-bottom microtiter plate (Greiner Labortechnik). Recombinant MOGxCD3 protein was added to obtain final concentrations of 0.032 up to 100 μg/ml in a total volume of 50 μl per well. Bound fusion protein was detected via binding of 8,18-C5 diluted 1:1000 in FACS-buffer, whereafter bound mouse monoclonal antibody was stained with α-mouse IgG-FITC (Sigma F-6257) at 1:40 dilution (FIG. 6).

EXAMPLE 9

Figure 8:
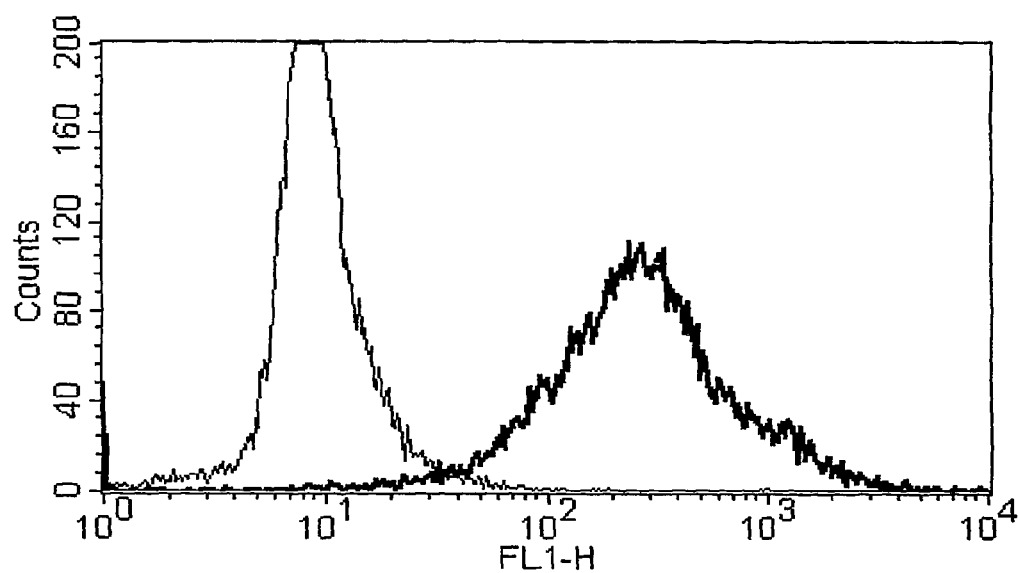
FIG. 8. 8.18-C5 hybridoma cells show surface expression of IgG1. Hybridomas were cultivated in serum-free medium for 4-5 months, and cell-surface IgG1 expression was examined by FACS analysis (A) with FITC-labelled anti-IgG1 antibody and (B) with biotinylated rMOG (recombinant MOG extracellular domain), followed by FITC-labeled streptavidin.
Figure 8:
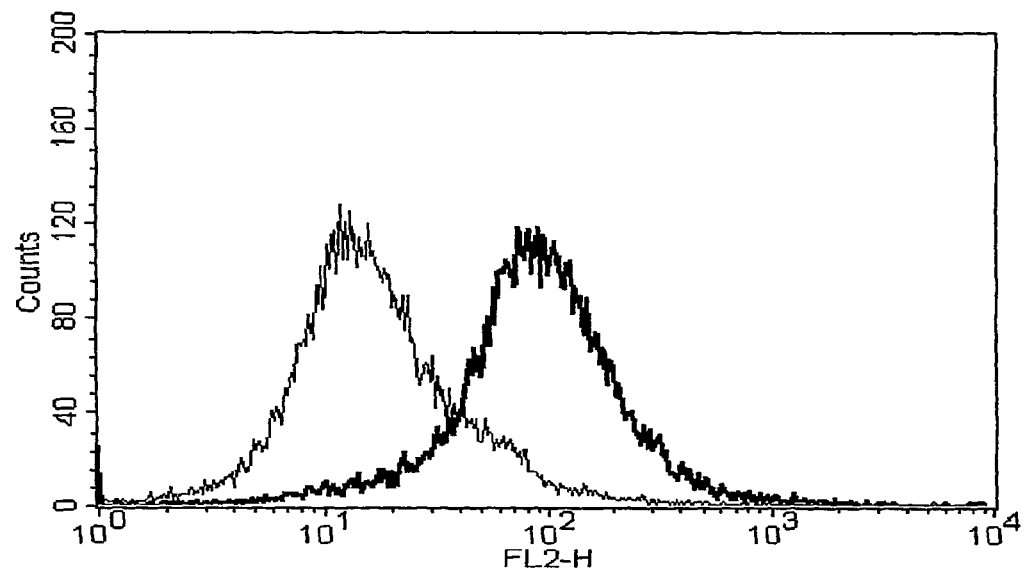

Establishment of a Cytotoxicity Assay for MOGxCD3 and MOG-Fc Fusion Proteins 9.1. Establishment of Cell-surface αMOG-positive Hybridoma Cell Line 8.18-C5 hybridoma cell line (Schluesener, J. Immunol. 139 (1987), 4016-4021) was adapted to serum-free medium (Hybridoma SFM, Gibco). Cells were passaged 1:5 every third day, and cultured in 100% SFM for a period of 4-5 months. Thereafter, MOG-reactivity in the hybridoma pool was assessed by FACS-analysis, using biotinylated MOG protein for staining. Positive cells were identified and isolated individually in 96-well plates by FACS-sorting. Clones were expanded for a period of approximately 2 weeks, and MOG-reactivity was checked again as described above. Anti-MOG positive clones were identified, and those showing the greatest amount of MOG-reactivity were expanded and used as targets for in-vitro cytotoxicity assays. More than 90% of cells show cell-surface expression of mIgG1 (FIG. 8A) and bound rMOG (FIG. 8B).

9.2. Selective Elimination of Autoreactive B-cells

Figure 9:
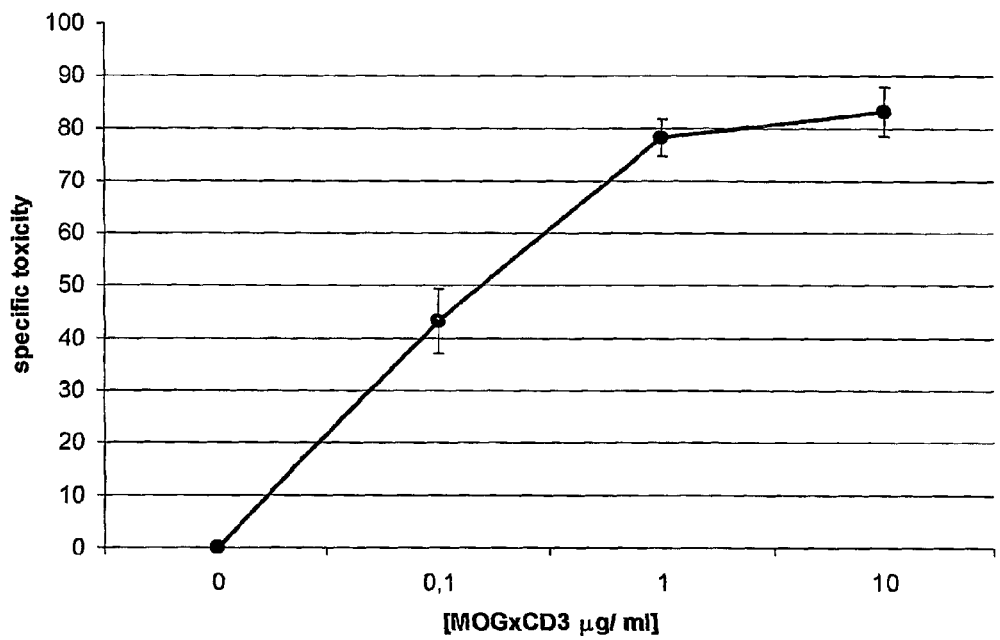
FIG. 9. Cytotoxic activity of autoantigen-effector proteins. FACS-based cytotoxicity assay with MOGxCD3 fusion protein. 8.18-C5 target cells were incubated with human CD3+ PBMCs and serial dilutions of MOGxCD3 protein in RPMI/10% FCS. Incubation was performed for 16 h at 37° C./5% $CO_2$. After incubation, target cells were labeled with anti-IgG1 antibody and analyzed for viability through propidium iodide staining. Viable murine IgG1(+) cells were counted and expressed as percentage of viable target cells in control: (A) MOGxCD3, (B) MOG-Fc fusion protein.
Figure 9:
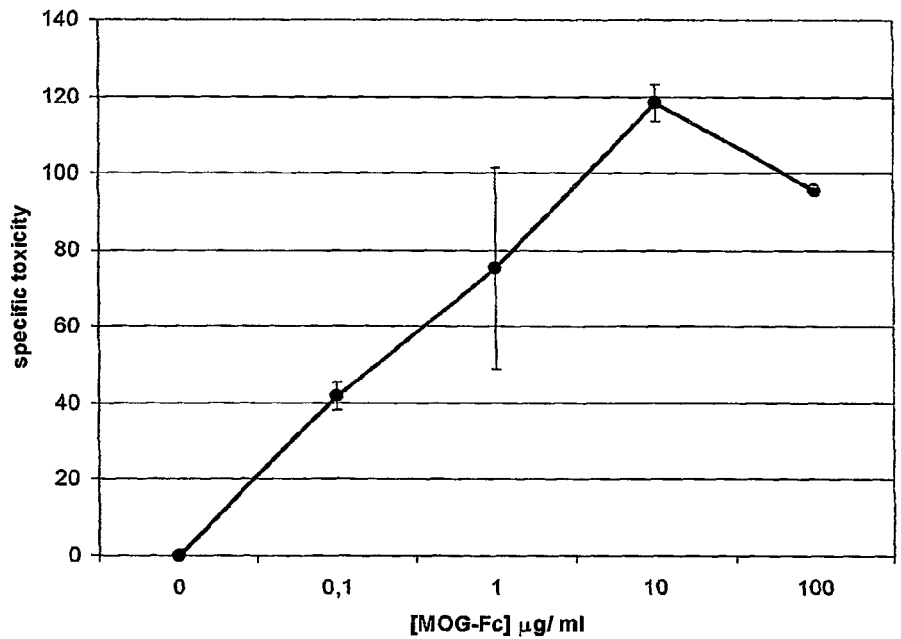
Figure 10:
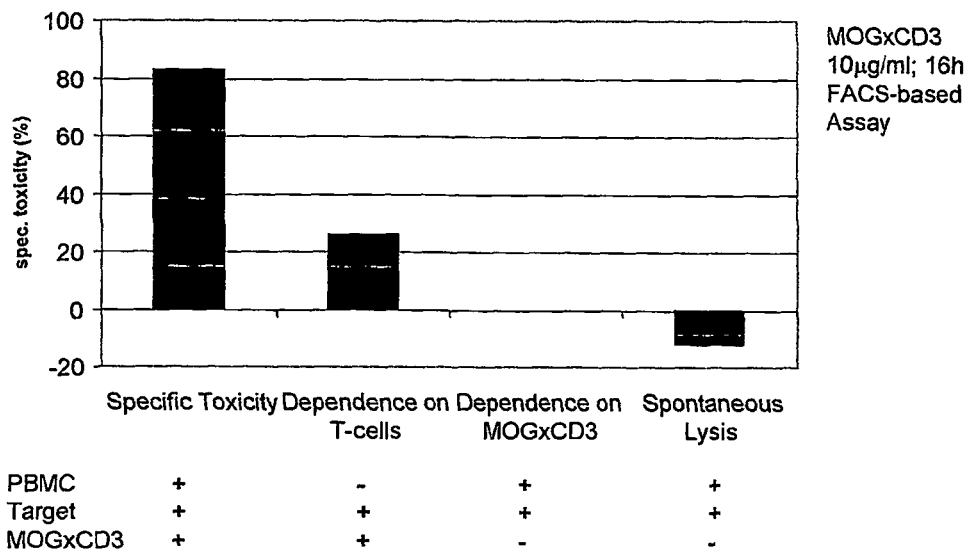
FIG. 10. Specificity of elimination of autoreactive B cells. MOGxCD3 cytotoxicities. Parameters shown represent: specific toxicity as described in FIG. 9; to measure spontaneous lysis target and effector cells had been incubated separately for the duration of the assay and were combined just prior to analysis: (A) MOGxCD3, (B) MOG-Fc.
Figure 10:
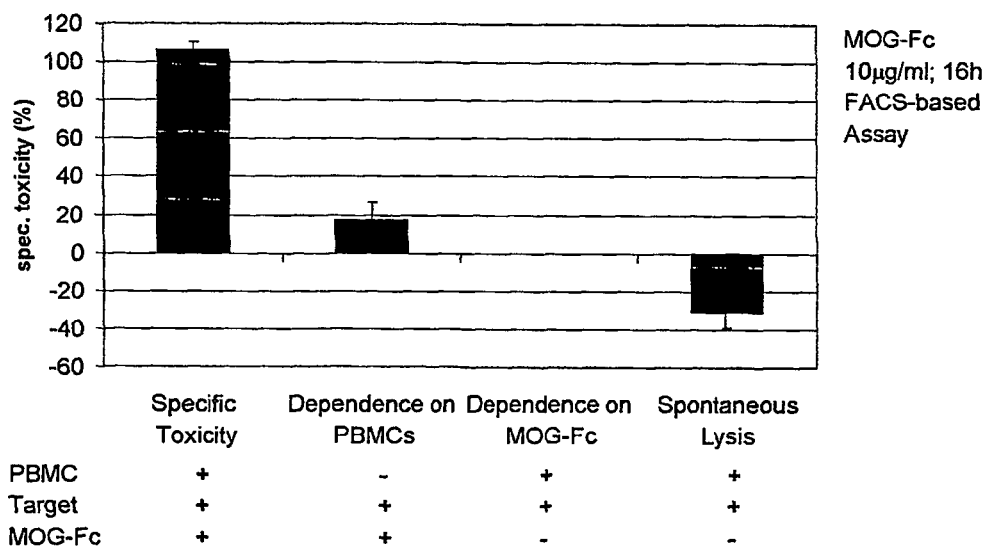

A FACS-based cytotoxicity assay was performed. Effector cells (500000), 8.18-C5 target cells and fusion protein were added in a total volume of 200 μl RPMI/10% FCS to each well of a sterile round-bottom multititre plate (CoStar) and incubated overnight at 37° C. Target cells were added to obtain E:T-ratios of 10:1, and MOGxCD3/-Fc fusion protein was added to attain final concentrations of 0.1, 1 and 10 μg/ml. Cells were incubated for 16 h at 37° C., washed with FACS-buffer, and target cells were labeled with anti-murin IgG1 antibody (Sigma 6257) at 1:50 dilutions in FACS-buffer; incubation was performed at RT for 30 min. Dead cells were excluded by staining with propidium iodide, and cells were analyzed with a FACSCalibur (Becton Dickinson). Dose-dependent cytotoxicity is shown for MOGxCD3 in FIG. 9A and for MOG-Fc in FIG. 9B. Specific toxicity is shown in FIG. 10 assay conditions were as described above, unspecific toxicity was defined cytotoxicity measured in the absence of protein. Spontaneous lysis was determined by separately incubated target and effector cells in the absence of protein, the cells were mixed prior to FACS analysis. The negative values reflect slight proliferation during the 16 h incubation.

EXAMPLE 10

Inhibition of MOGxCD3 Cytotoxicity by Recombinant MOG (rMOG)

Figure 11:
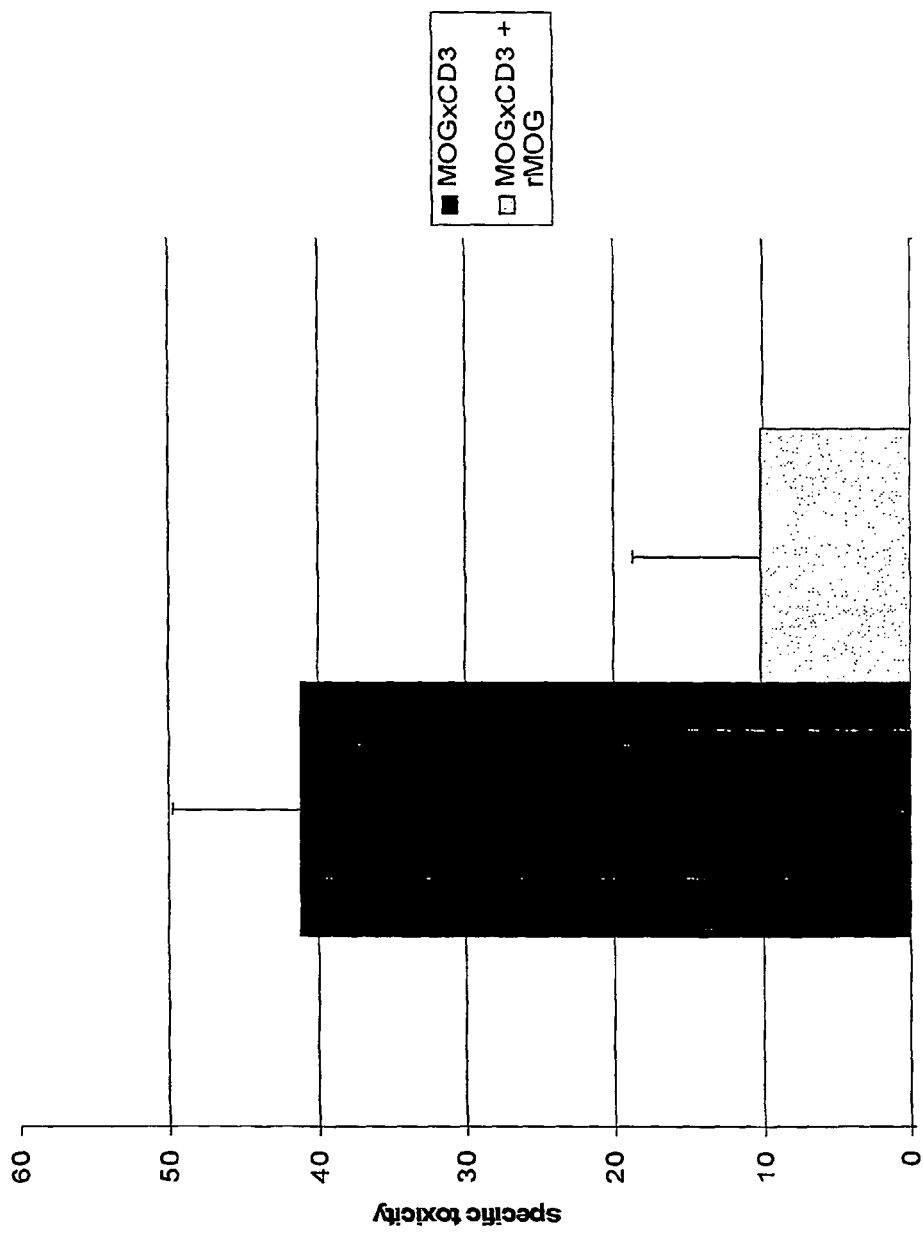
FIG. 11. Cytotoxicity of MOGxCD3 is inhibited by recombinant MOG. MOGxCD3 was used at 0.1 µg/ml in FACS-based cytotoxicity assay as described for FIG. 9. Recombinant, biotinylated MOG was added to obtain a final concentration of 20 µg/ml.

The specificity of MOGxCD3 based cytotoxicity was tested by addition of soluble recombinant MOG. A FACS-based cytotoxicity assay was performed as described in example 9, using MOGxCD3 at a concentration of 0.1 μg/ml. Recombinant, biotinylated MOG (rMOG) was added to a final concentration of 20 μg/ml and the cytotoxicity assay performed for 16 h. As shown in FIG. 11, cytotoxic activity can be inhibited by the addition of rMOG.

EXAMPLE 11

MOGxCD3 Binds to 8.18-C5 Target Cells

Figure 12:
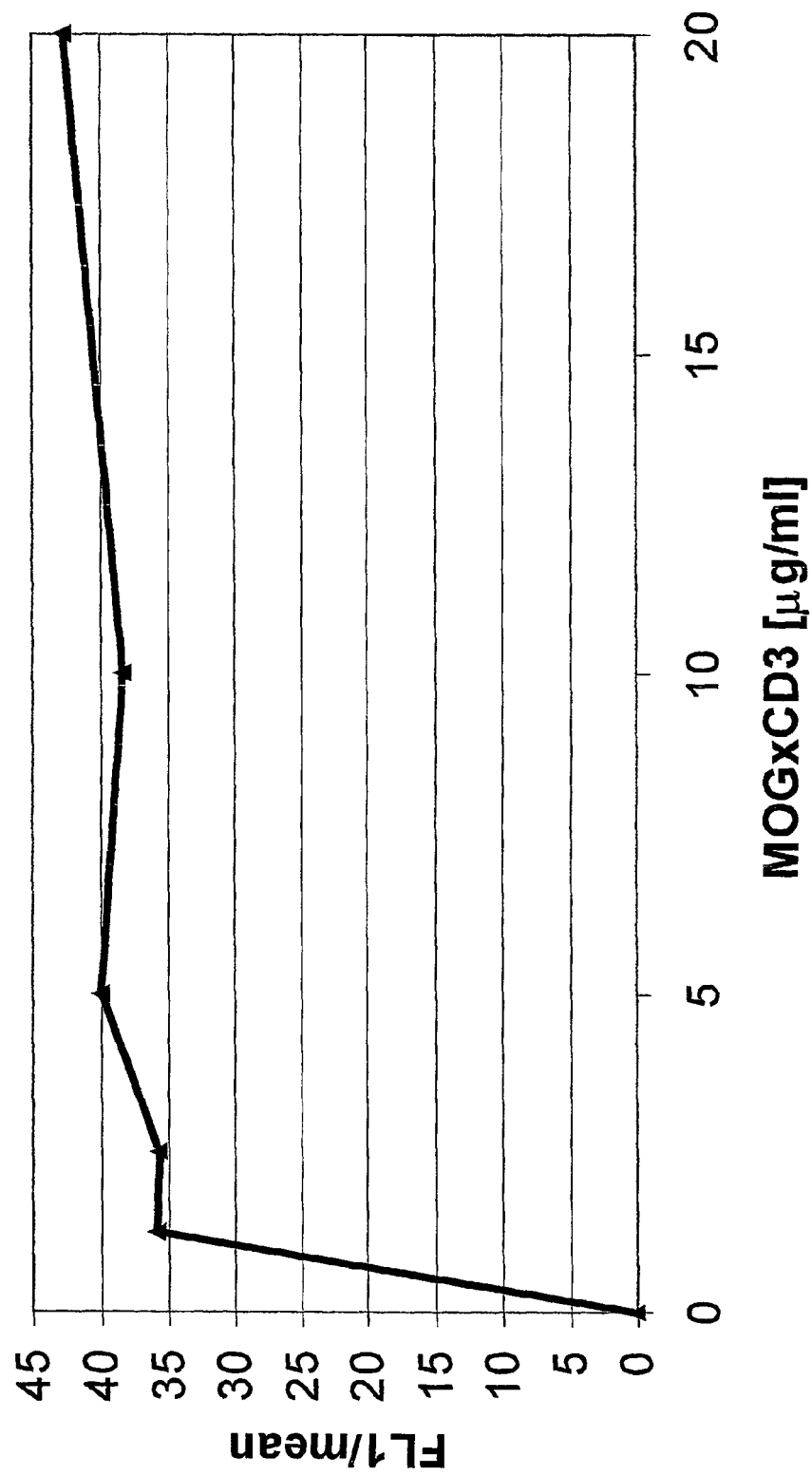
FIG. 12. MOGxCD3 binds to 8.18-C5 target cells. Binding was assessed with FITC-labeled anti-HIS antibody (Dianova) at 10 µg/ml.

Binding of MOGxCD3 to B cell carrying membrane Ig receptor specific for the MOG protein was tested by a FACS-based binding assay. 8.18-C5 target cells were incubated with purified MOGxCD3 fusion protein at various concentrations for 1 h at 4° C. Cells were washed twice with FACS-buffer, and bound fusion protein was detected through its C-terminal HIS-tag using FITC-labeled anti-HIS antibody (Dianova). Cells were analyzed by FACS scanning and mean fluorescence scores were calculated and are shown in FIG. 12. MOGxCD3 efficiently bound at concentrations below 5 μg/ml.

EXAMPLE 12

Selective Elimination of Autoreactive B-cells at Different Effector-to-target Ratios (E:T).

Figure 13:
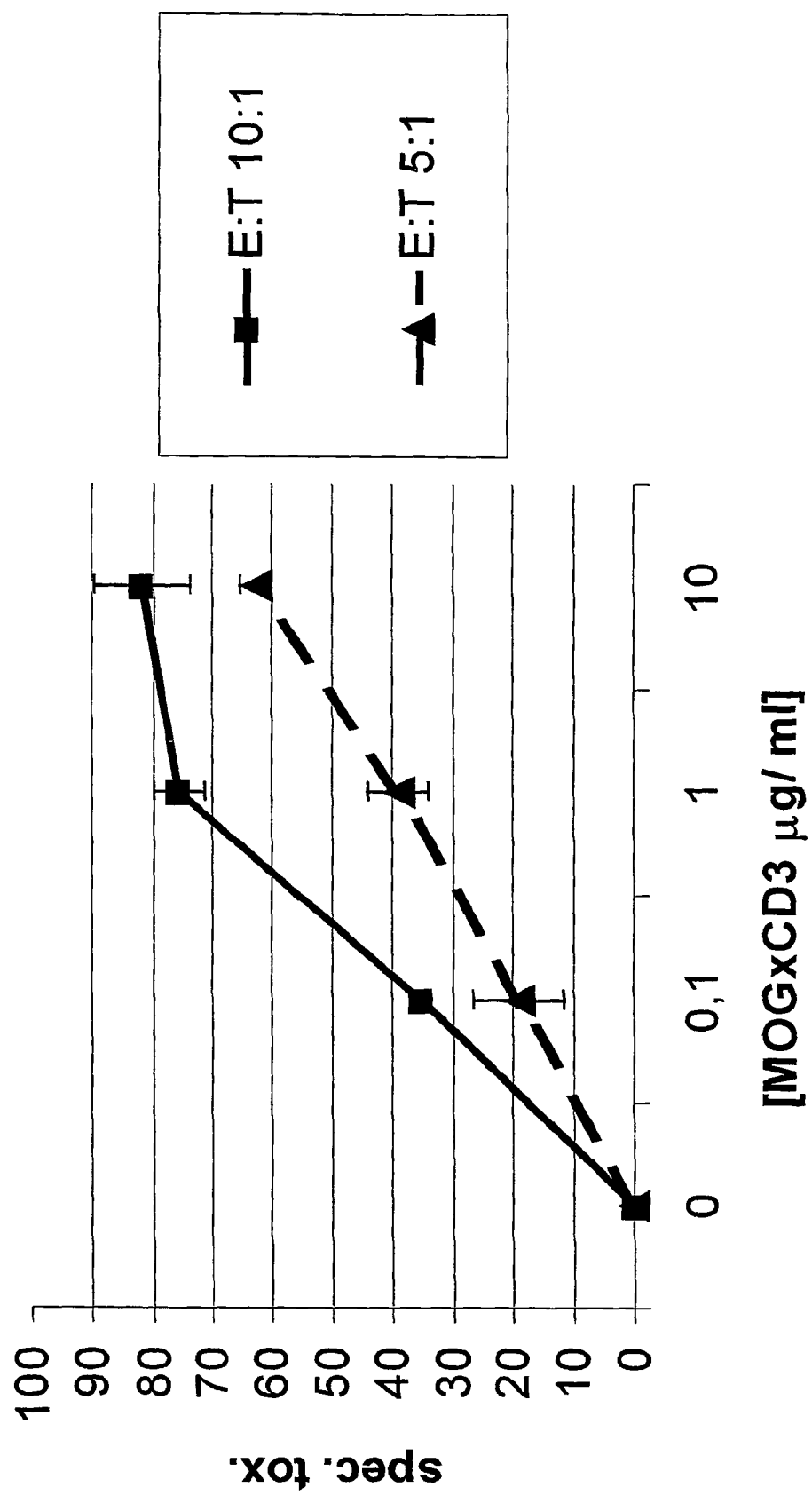
FIG. 13. Cytotoxic activity of MOGxCD3 is dependent on effector cell to target ratio. Assay was performed as described for FIG. 9 with varying concentrations of effector cells and a constant number of 8.18-C5 target cells.

The dependency of MOGxCD3 cytotoxicity on the availability of effector cells was determined by a FACS-based cytotoxicity assay as described in example 9. Target cells were seeded at a constant density of 50000 cells/well, while the CD3+ human effector cell concentration was varied in order to obtain the desired E:T ratio. FIG. 13 shows the corresponding specific toxicity, demonstrating that MOGxCD3 cytotoxicity is dependent on effector cell number.

EXAMPLE 13

Figure 14A:
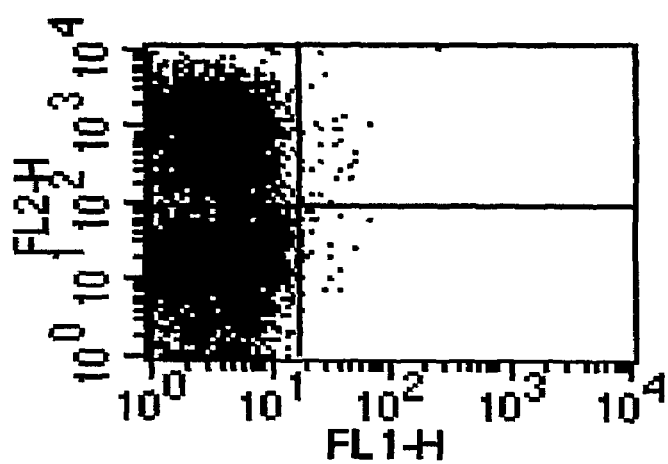
FIG. 14. Flow cytometric analysis of cell binding properties of MOG-Fc.
Figure 14A:
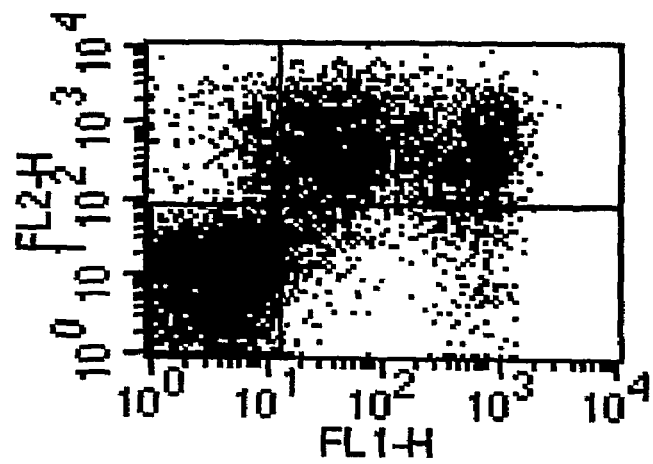
Figure 14D:
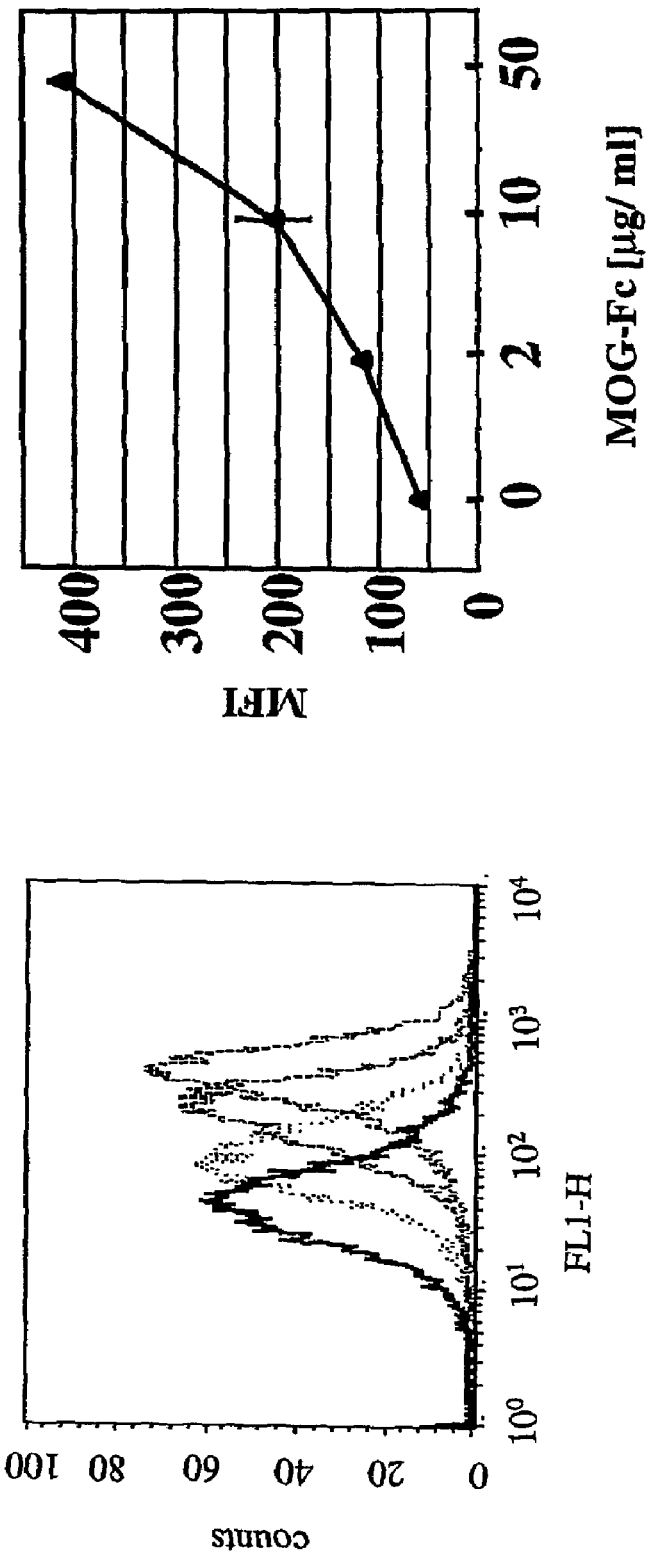

Binding Specificity of Auto-antigen Fusion Proteins to Autoreactive B-cells 13.1. Specific Binding of MOG-FC Fusion Protein to IgM+ B-cells Derived from Splenocytes from Anti-MOG Transgenic Mice Binding of MOG-Fc as described in Example 3 and FIG. 4 to MOG-reactive B cells was investigated using splenocytes from anti-MOG transgenic mice (FIG. 14A, lower panel). In these mice, the endogenous heavy chain-J region has been replaced by the rearranged 8.18-C5 anti-MOG VDJ segment using knock-in technology (Litzenburger, J. Exp. Med. 188 (1998), 169-180). As a result, almost all B cells of transgenic mice express the MOG-specific heavy chain in combination with endogenous light chains.

Whole lymphocytes from transgenic knock-in mice were prepared from spleen as described elsewhere (Litzenburger, J. Exp. Med. 188 (1998), 169-180). Cells were incubated with MOG-Fc fusion protein for 20 min on ice, and bound MOG-Fc was detected with goat-anti-human IgG FITC antibody (ICN 67-217). It was shown in FACS analysis that >90% of all IgM-positive splenocytes from the anti-MOG transgenic mice (FIG. 14A, lower panel) but not of control littermate mice (FIG. 14A, upper panel) did bind recombinant MOG-Fc. Two populations of B-cells were observed: Approximately one third of IgM-positive B cells in anti-MOG transgenic mice bound MOG-Fc with high intensity while two thirds bound MOG-Fc with low intensity (FIG. 14A, lower panel). This binding pattern was reminiscent of the one reported using biotinylated, bacterially produced, recombinant rat MOG (rMOG) (Litzenburger, J. Exp. Med. 188 (1998), 169-180 and Litzenburger, J. Immunol. 165, (2000) 5360-5366). In this report, however, two thirds of the B cells derived from anti-MOG transgenic mice did not bind rMOG at all or only poorly, and only one third of B cells bound rMOG with a broad range of intensities. Such differences are likely due to an intrinsically higher affinity of these B cells to MOG-Fc which, in contrast to the bacterially generated rMOG, is dimeric, properly folded, N-glycosylated and has not undergone biotinylation.

13.2. Selective Binding of MOG-Fc Fusion Protein to Wildtype Murine Splenocytes

Binding of MOG-Fc (as described in Example 3 and FIG. 4) to wildtype splenocytes was also investigated. Single-cell suspensions of wildtype splenocytes were prepared. Cells were incubated with 50 µg/ml MOG-Fc protein or PBS.

In order to allow binding to low-affinity Fc receptors, incubation with MOG-Fc was performed with 10-times the concentration of protein as with splenocytes from anti-MOG transgenic mice (Litzenburger, J. Exp. Med. 188 (1998), 169-180) and for a period of 45 minutes at room temperature compared to 20 minutes on ice. The subsequent incubation with anti-Mac1, anti-CD5 or biotinylated 8.18-C5 antibodies was performed on ice for 20 min. As shown in FIG. 14B, MOG-Fc did bind to the Mac1$^{high}$ (CD11b, BD Pharmingen) positive population, indicating a preferential binding to macrophages and myeloid CD8$^+$ dendritic cells (DCs). The upper panels of FIG. 14B and C show incubations on ice alone without prior incubation with MOG-Fc at room temperature. No binding of MOG-Fc to CD5$^+$ T cells could be detected emphasizing the selectivity for FcγR$^+$ cells.

13.3. Specific Binding of MOG-Fc Fusion Protein to Murine Macrophage Cell Line

Figure 1:
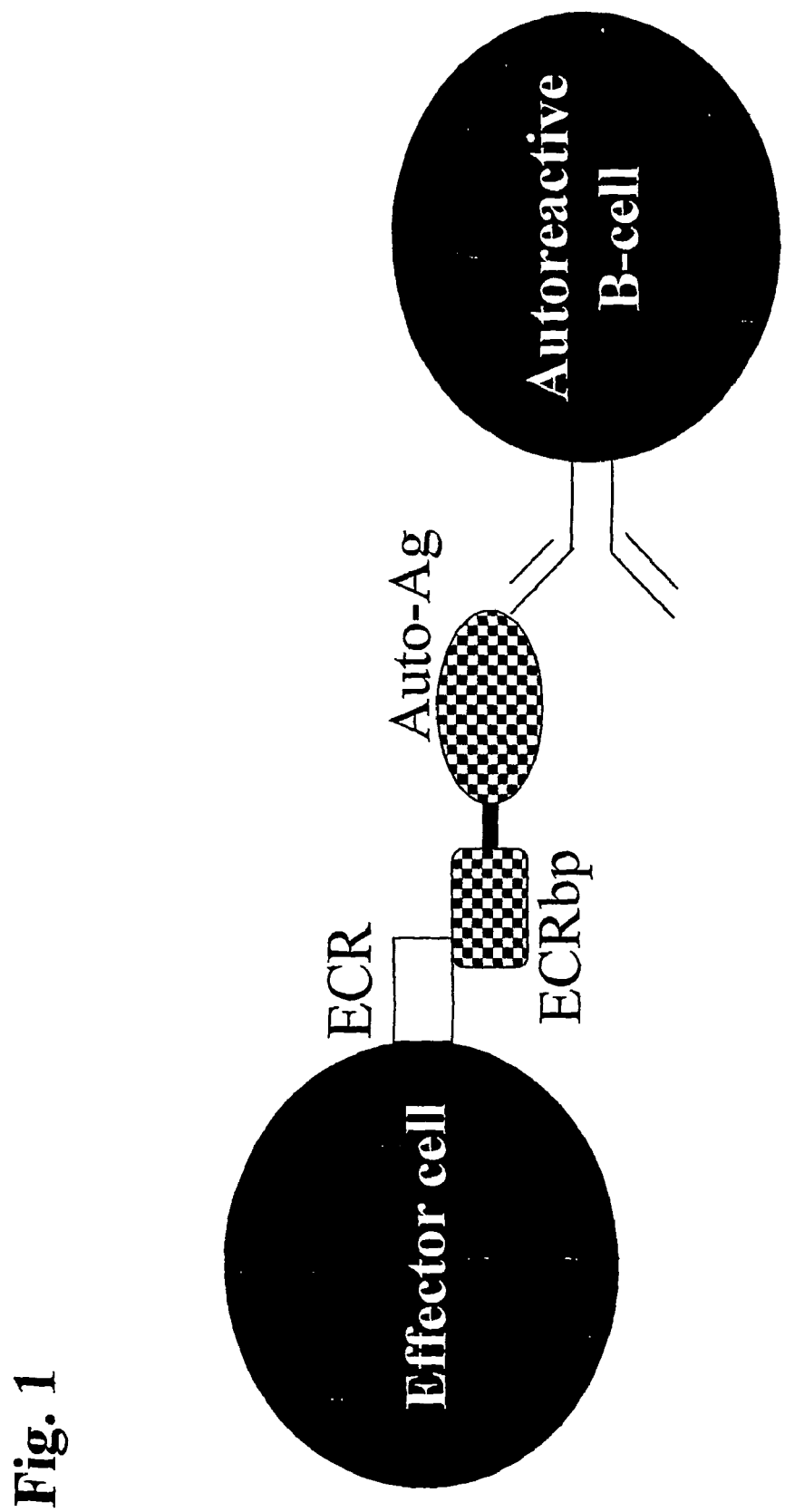
FIG. 1 Overview of concept for the elimination of autoreactive B cells. Overview of elimination of autoreactive B cells using molecules comprising an autoantigen and an effector molecule domain. Abbreviations are ECR: Effector cell receptor; ECRbp: Effector cell receptor binding protein; Ag: Antigen.

The murine monocyte/macrophage cell line p388.D1 also bound MOG-Fc (as described in Example 3 and FIG. 4) as shown by FACS detection of MOG-Fc via FITC-labeled anti-human Fcγ antibody (FIG. 1D). Mean fluorescence intensity (MFI) values observed for MOG-Fc were similar to those obtained with an isotype control IgG1 (Raum, Cancer Immunol Immunother. 50, (2001), 141-150) (data not shown).

EXAMPLE 14

Specificity of MOG-Fc Mediated Cytotoxicity

The specificity of cell lysis mediated by MOG-Fc (as described in Example 3 and FIG. 4) was investigated by using both unrelated human IgG1 (Raum, Cancer Immunol Immunother. 50, (2001), 141-150) and a mouse B cell line expressing unrelated IgG on its surface (TIB-208).

14.1. Effect of Non-specific Human IgG1

Figure 15A:
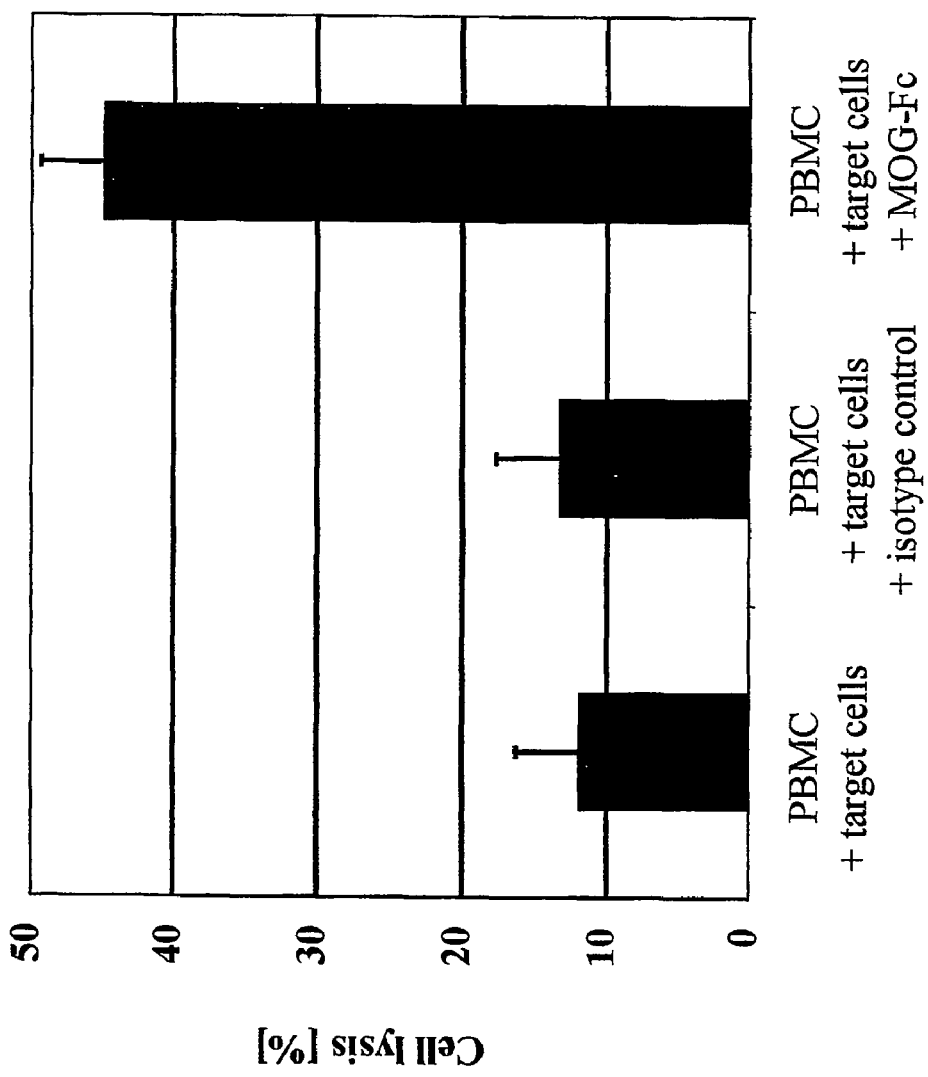

8.18-C5 target cells were incubated with human PBMCs and 10 µg/ml MOG-Fc protein (as described in Example 3 and FIG. 4) in RPMI with 10% FCS. Incubation was performed for 16 h at 37° C./5% CO$_2$. After incubation, target cells were detected with FITC-labeled anti-murine IgG1 antibody (mIgG, Pharmingen) and analyzed for viability through propidium iodide (PI) staining. The EpCAM antigen-specific recombinant human control IgG1 (Raum, Cancer Immunol Immunother. 50, (2001), 141-150) can bind to human effector cells via its Fc part but not to MOG-specific immunoglobulin on hybridoma cells. This isotype control did not lead to significant redirected lysis of 8.18-C5 cells (FIG. 15A).

14.2. Effect of an Unrelated Murine Cell Line Expressing Cell Surface IgG1

Figure 15B:
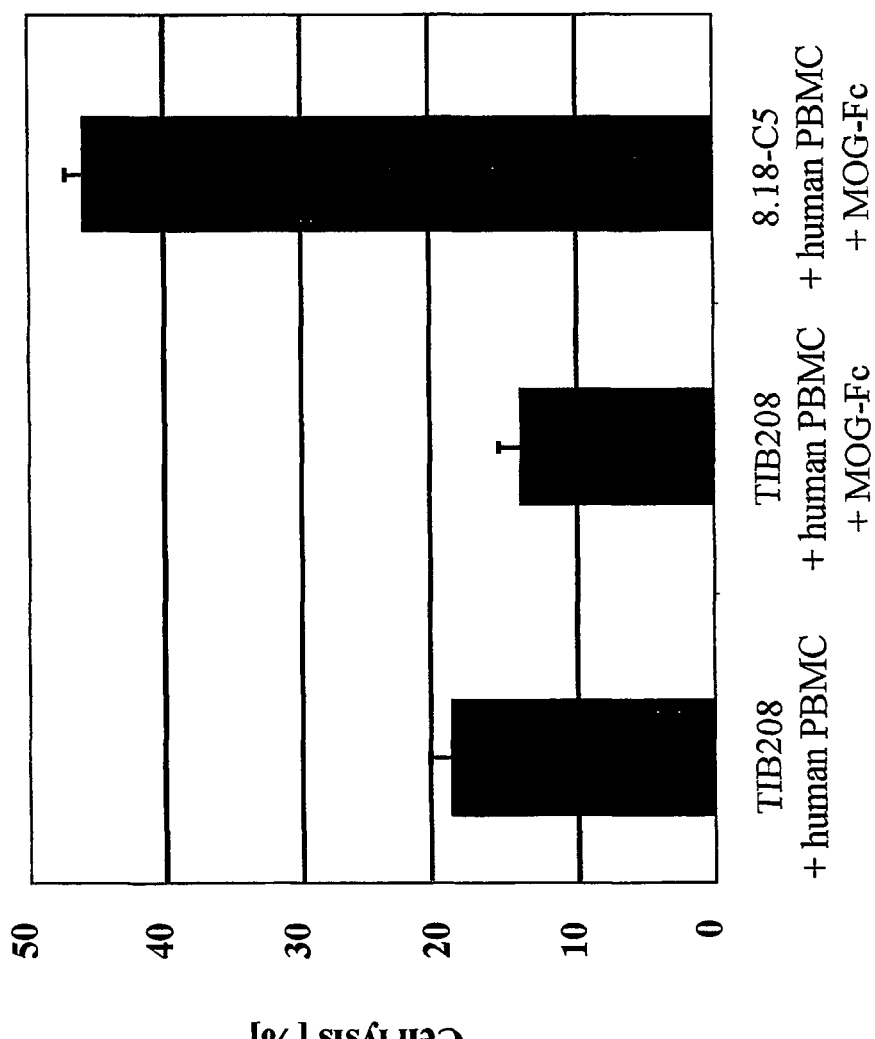

Mouse B cell line TIB-208 is expressing cell surface IgG1 of non-MOG specificity and was incubated with human PBMCs and 10 µg/ml MOG-Fc protein (as described in Example 3 and FIG. 4) in RPMI with 10% FCS. Incubation was performed for 16 h at 37° C. and 5% CO$_2$. The mouse B cell line TIB-208 expressing cell-surface IgG of non-MOG specificity was not sensitive to MOG-Fc mediated cell lysis (FIG. 15B).

EXAMPLE 15

MOG-Fc Mediated Depletion of Splenocytes of Anti-MOG Transgenic Mice ex vivo

To investigate the cytotoxic potential of MOG-Fc (as described in Example 3 and FIG. 4) on MOG-specific B cells in vivo, the fusion protein was tested in anti-MOG transgenic mice. Firstly, anti-MOG mice have an extremely high titer of circulating MOG-reactive antibodies (Litzenburger, J. Exp. Med., 188, (1998) 169-180) and secondly, almost all B cells in these mice do show MOG reactivity. MOG-Fc had the ability to deplete primary anti-MOG-positive B cells from anti-MOG transgenic mice ex vivo and in vivo. Elimination of MOG-reactive B cells ex vivo was efficient (on the order of 70% within 16 hours), while in vivo it was lower but still significant among the population of highly MOG-reactive B cells. MOG-reactive B cells are constantly replenished in the periphery by the bone marrow on the order of 10$^7$ cells/day. In contrast, the frequency of autoreactive B cells in human autoimmune disease is extremely low (Link, J. Clin. Invest., 87, (1991), 2191-2195 and Nishifuji, J. Invest. Dermatol., 114, (2000), 88-94). Therefore, the anti-MOG transgenic mouse model represented the most difficult situation and highest possible hurdle to test the in-vivo efficacy of a specific B cell-eliminating protein such as MOG-Fc.

In order to assess whether MOG-Fc (as described in Example 3 and FIG. 4) can also eliminate normal B cells expressing MOG-reactive cell-surface immunoglobulin, splenocytes from anti-MOG transgenic mice were isolated and incubated with 10 µg/ml of MOG-Fc fusion protein for 16 h at 37° C. and 5% $CO_2$ in DMEM with 10% FCS in 5 ml cell culture polypropylene vials (Becton-Dickinson, Pharmingen) at a density of $4\times10^6$ cells/ml. Lymphocyte analysis was carried out by FACS using biotinylated recombinant MOG protein and antibodies against $IgM^a$, IgD and CD19 (all Becton-Dickinson, Pharmingen). All tests were carried out in triplicate. The endogenous Fcγ receptor-bearing cells served as effectors. In FACS analysis, a highly significant depletion of B cells positive for $IgM^a$, IgD and CD19 was observed (FIG. 16). The average degree of B cell depletion was on the order of 70% and was comparable for all three B-cell markers.

EXAMPLE 16

In Vivo Depletion of Anti-MOG Specific B-cells in Transgenic Mice

The cytotoxic efficacy of MOG-Fc (as described in Example 3 and FIG. 4) was tested in vivo using the anti-MOG transgenic mouse. This mouse strain carries the anti-MOG heavy chain variable region, derived from the anti-MOG monoclonal antibody 8.18-C5 "knocked in" for the germline JH locus (Litzenburger, J. Exp. Med. 188 (1998), 169-180).

Figure 17A:
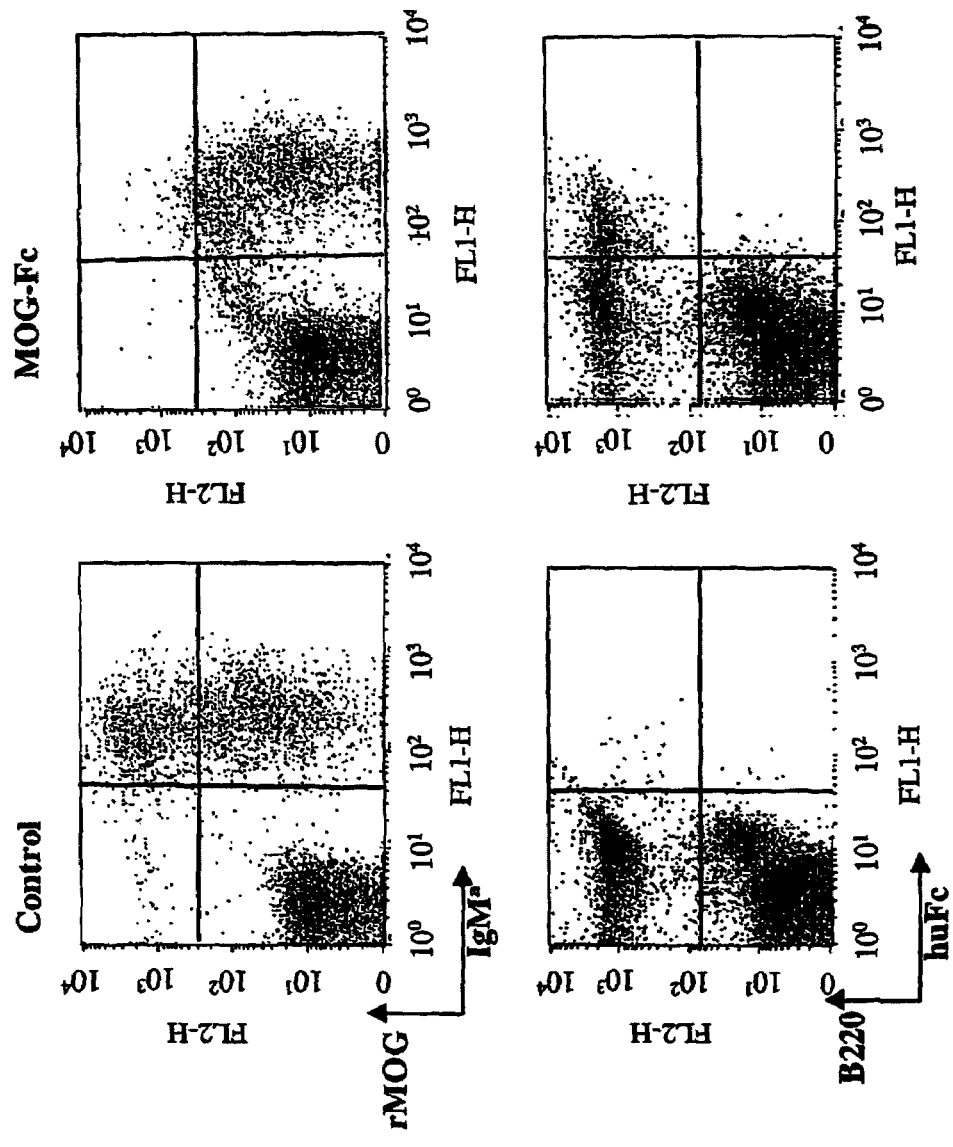

Female anti-MOG transgenic mice were treated twice with. 100 μg of recombinant MOG-Fc fusion protein in 500 μl PBS through i.p. injection (n=5) on day 1 and 3. Blood was collected each day after treatment, PBLs were prepared, and lymphocytes were analyzed via FACS (FACSCalibur, Becton-Dickinson) analysis one day post treatment. $MOG^+$ B cells were quantitated and normalized as percentage of total $B220^+$ B cells detected in the lymphocyte gate. MOG-Fc was efficient in depleting IgM-positive B cells in the fraction that strongly reacted with MOG (FIG. 17A, upper panel). MOG-FC was still bound to B cells 24 h post-treatment (FIG. 17B) as detected by staining of isolated B220-positive blood lymphocytes with anti-human Fcγ specific antibody.

Figure 17B:
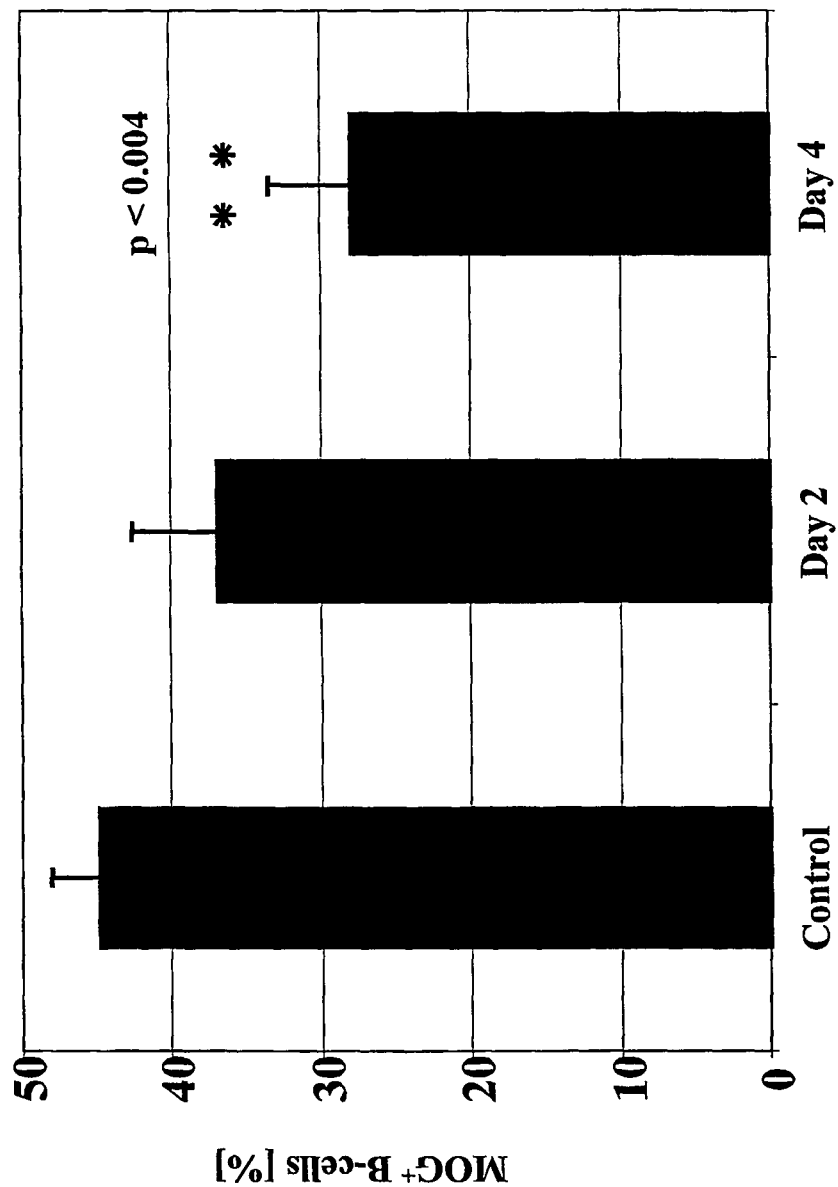

The percentage of highly MOG expressing B-cells decreased with statistical significance from 45% in control (untreated mice) to less than 30% on day 4 after the first treatment (FIG. 17B). The number of $B220^+$ B cells was decreased to the same extent as the number of IgM-positive B cells (data not shown), suggesting that the reduction of B cells measured by flow cytometry was due to a depletion of cells and not to a down-modulation of the B-cell receptor expression.

EXAMPLE 17

Depletion of Autoreactive B Cells and Reduction of MOG-specific IgG in Wildtype Mice After Cellular Transfer 17.1 In Vivo Depletion of Anti-MOG Reactive B Cells in Wildtype Mice After Cellular Transfer In order to study the depleting potential of MOG-Fc on a limited number of B-cells derived from anti-MOG transgenic mice in vivo, $1.5\times10^7$ B cells derived from anti-MOG transgenic mice with BL/6 background were transferred intraveniously into wt BL/6;

Wild-type mice transferred With a limited number of autoreactive B-cells can be used as a model system reflecting the situation in B-cell-mediated autoimmunity which is characterized by the presence of a limited number of autoreactive B-cells versus a high background of endogenous normal B lymphocytes. Thus, this system is very close to the real-life situation and confirms the data on depletion of MOG-reactive B cells obtained in the anti-MOG transgenic mice.

Mice were divided into 3 groups (N=5 per group). Group A was treated with MOG-Fc (100 ug each treatment) intraperitoneally 1, 2 and 3 days post-transfer. Control groups were treated with human IgG1 isotype control (Raum, Cancer Immunol Immunother. 50, (2001), 141-150, group B) and PBS (group C). For this purpose splenocytes derived from anti-MOG transgenic mice with BL/6 background were prepared as single-cell suspension and stimulated with LPS as described (Litzenburger, J. Exp. Med. 188 (1998), 169-180). Three days post-stimulation at 37° C./5% CO2, resting B-cells (CD43−) were isolated (Litzenburger, J. Exp. Med. 188 (1998), 169-180) and $1.5\times10^7$ cells were transferred intravenously into wildtype BL/6 mice on the same day. Mice were treated as described above on days 1, 2 and 3 following transfer. 24 h and 72 h after the last treatment, peripheral blood was collected by tail bleeding and analyzed for anti-MOG reactive B cells via FACS staining (FACS Calibur, Becton-Dickinson) with recombinant MOG-Fc (as described in Example 3 and FIG. 4) followed by detection with PE-conjugated anti-human Fc antibody (ICN).

One day post-treatment with MOG-Fc depletion of MOG-reactive B cells (FIG. 18A) was observed. This effect was more prominent three days post-treatment showing a depletion af autoreactive B-cells in the order of 70% (FIG. 18B).

17.2. Reduction of MOG-specific IgG in Wildtype Mice After Cellular Transfer $1.5\times10^7$ B cells derived from anti-MOG transgenic mice with BL/6 background were transferred intraveniously into wt BL/6 as described in Example 17.1. Mice were divided into 3 groups (N=5 per group) and treated with MOG-Fc (100 ug each treatment) intraperitoneally 1, 2 and 3 days post-transfer (A), human IgG1 isotype control (Raum, Cancer Immunol Immunother. 50, (2001), 141-150, group B) and PBS (group C). Peripheral blood was collected by tail bleeding and sera from day 1 and 3 post-treatment were analyzed for anti-MOG specific IgG titers by ELISA. ELISA plates were coated with recombinant MOG (10 μg/ml), serum samples collected 24 h post-treatment were applied at 1:100 dilution and serum samples collected at 72 h post-treatment were applied at 1:1000 dilution in PBS. Bound MOG-reactive IgG was detected with biotinylated rat-anti-mouse IgG antibody (Jackson Laboratories). Streptavidin-AP and pNPP (Sigma N-2770) were used for detection and OD values were quantified on a Dynatech MR4000 ELISA reader.

MOG-Fc had the ability to reduce the number of circulating, MOG-reactive IgG after 24 h (FIG. 19A) and 72 h (FIG. 19B), presumably via a combination of direct adsorption and neutralization of MOG-reactive immunoglobulin.

Both effects described in Example 17.1. and 17.2. are of high therapeutic value, since immunoadsorption of autoreactive immunoglobulin leads to a short-term effect through depletion of pathogenic antibodies, while elimination of autoreactive B cells depletes the pathogenic cellular reservoir.

The invention claimed is:

1. A composition comprising at least one polypeptide construct consisting of two domains wherein (i) one of said domains comprises an autoreactive antigen MOG specifically recognized by the Ig receptors of autoreactive B-cells and (ii) wherein one of said domains comprises an Fc part of an immunoglobulin effector molecule capable of interacting with and/or of activating NK-cells, T-cells, macrophages, monocytes, and/or granulocytes or capable of activating the complement systems, and wherein (a) said polypeptide construct comprises the amino acid sequence of SEQ ID NO:4; or (b) is encoded by a polynucleotide comprising the DNA sequence of SEQ ID NO: 3.

2. The composition of claim 1, wherein said T cells are cytotoxic T cells.

* * * * *

SEQUENCE LISTING

<160> NUMBER OF SEQ ID NOS: 9

<210> SEQ ID NO 1
<211> LENGTH: 1241
<212> TYPE: DNA
<213> ORGANISM: Homo sapiens

<400> SEQUENCE: 1

```
gaattcatgg caagcttatc gagaccctct ctgcccagct gcctctgctc cttcctcctc     60
ctcctcctcc tccaagtgtc ttccagctat gcagggcagt tcagagtgat aggaccaaga    120
caccctatcc gggctctggt cggggatgaa gtggaattgc catgtcgcat atctcctggg    180
aagaacgcta caggcatgga ggtggggtgg taccgccccc ccttctctag ggtggttcat    240
ctctacagaa atggcaagga ccaagatgga gaccaggcac ctgaatatcg gggccggaca    300
gagctgctga agatgctat tggtgaggga aaggtgactc tcaggatccg gaatgtaagg    360
ttctcagatg aaggaggttt cacctgcttc ttccgagatc attcttacca agaggaggca    420
gcaatggaat tgaaagtaga agatcctttc tactgggtga gccctggatc cggaggtggt    480
ggatccgata tcaaactgca gcagtcaggg gctgaactgg caagacctgg ggcctcagtg    540
aagatgtcct gcaagacttc tggctacacc tttactaggt acacgatgca ctgggtaaaa    600
cagaggcctg acagggtct ggaatggatt ggatacatta atcctagccg tggttatact    660
aattacaatc agaagttcaa ggacaaggcc acattgacta cagacaaatc ctccagcaca    720
gcctacatgc aactgagcag cctgacatct gaggactctg cagtctatta ctgtgcaaga    780
tattatgatg atcattactg cctttgactac tggggccaag gcaccactct cacagtctcc    840
tcagtcgaag gtggaagtgg aggttctggt ggaagtggag gttcaggtgg agtcgacgac    900
attcagctga cccagtctcc agcaatcatg tctgcatctc caggggagaa ggtcaccatg    960
acctgcagag ccagttcaag tgtaagttac atgaactggt accagcagaa gtcaggcacc   1020
tcccccaaaa gatggattta tgacacatcc aaagtggctt ctggagtccc ttatcgcttc   1080
agtggcagtg ggtctgggac ctcatactct ctcacaatca gcagcatgga ggctgaagat   1140
gctgccactt attactgcca acagtggagt agtaacccgc tcacgttcgg tgctgggacc   1200
aagctggagc tgaaacatca tcaccatcat cattagtcga c                       1241
```

<210> SEQ ID NO 2
<211> LENGTH: 409
<212> TYPE: PRT
<213> ORGANISM: Homo sapiens

<400> SEQUENCE: 2

```
Met Ala Ser Leu Ser Arg Pro Ser Leu Pro Ser Cys Leu Cys Ser Phe
  1               5                  10                  15

Leu Leu Leu Leu Leu Gln Val Ser Ser Ser Tyr Ala Gly Gln Phe
                 20                  25                  30

Arg Val Ile Gly Pro Arg His Pro Ile Arg Ala Leu Val Gly Asp Glu
             35                  40                  45

Val Glu Leu Pro Cys Arg Ile Ser Pro Gly Lys Asn Ala Thr Gly Met
         50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95
```

Arg Thr Glu Leu Leu Lys Asp Ala Ile Gly Glu Gly Lys Val Thr Leu
                100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Met Glu Leu Lys Val
130                 135                 140

Glu Asp Pro Phe Tyr Trp Val Ser Pro Ser Gly Gly Gly Gly Gly Ser
145                 150                 155                 160

Asp Ile Lys Leu Gln Gln Ser Gly Ala Glu Leu Ala Arg Pro Gly Ala
                165                 170                 175

Ser Val Lys Met Ser Cys Lys Thr Ser Gly Tyr Thr Phe Thr Arg Tyr
            180                 185                 190

Thr Met His Trp Val Lys Gln Arg Pro Gly Gln Gly Leu Glu Trp Ile
        195                 200                 205

Gly Tyr Ile Asn Pro Ser Arg Gly Tyr Thr Asn Tyr Asn Gln Lys Phe
    210                 215                 220

Lys Asp Lys Ala Thr Leu Thr Thr Asp Lys Ser Ser Ser Thr Ala Tyr
225                 230                 235                 240

Met Gln Leu Ser Ser Leu Thr Ser Glu Asp Ser Ala Val Tyr Tyr Cys
                245                 250                 255

Ala Arg Tyr Tyr Asp Asp His Tyr Cys Leu Asp Tyr Trp Gly Gln Gly
            260                 265                 270

Thr Thr Leu Thr Val Ser Ser Val Glu Gly Gly Ser Gly Gly Ser Gly
        275                 280                 285

Gly Ser Gly Gly Ser Gly Gly Val Asp Asp Ile Gln Leu Thr Gln Ser
    290                 295                 300

Pro Ala Ile Met Ser Ala Ser Pro Gly Glu Lys Val Thr Met Thr Cys
305                 310                 315                 320

Arg Ala Ser Ser Ser Val Ser Tyr Met Asn Trp Tyr Gln Gln Lys Ser
                325                 330                 335

Gly Thr Ser Pro Lys Arg Trp Ile Tyr Asp Thr Ser Lys Val Ala Ser
            340                 345                 350

Gly Val Pro Tyr Arg Phe Ser Gly Ser Gly Ser Gly Thr Ser Tyr Ser
        355                 360                 365

Leu Thr Ile Ser Ser Met Glu Ala Glu Asp Ala Ala Thr Tyr Tyr Cys
    370                 375                 380

Gln Gln Trp Ser Ser Asn Pro Leu Thr Phe Gly Ala Gly Thr Lys Leu
385                 390                 395                 400

Glu Leu Lys His His His His His His
                405

<210> SEQ ID NO 3
<211> LENGTH: 1173
<212> TYPE: DNA
<213> ORGANISM: Homo sapiens

<400> SEQUENCE: 3
atggcaagct tatcgagacc ctctctgccc agctgcctct gctccttcct cctcctcctc        60
ctcctccaag tgtcttccag ctatgcaggg cagttcagag tgataggacc aagacaccct       120
atccgggctc tggtcgggga tgaagtggaa ttgccatgtc gcatatctcc tgggaagaac       180
gctacaggca tggaggtggg gtggtaccgc cccccttct ctagggtggt tcatctctac        240
agaaatggca aggaccaaga tggagaccag gcacctgaat atcggggccg gacagagctg       300

-continued

```
ctgaaagatg ctattggtga gggaaaggtg actctcagga tccggaatgt aaggttctca    360
gatgaaggag gtttcacctg cttcttccga gatcattctt accaagagga ggcagcaatg    420
gaattgaaag tagaagatcc tttctactgg gtgagccctg gatccggaga gcccaaatct    480
tgtgacaaaa ctcacacatg cccaccgtgc ccagcacctg aactcctggg gggaccgtca    540
gtcttcctct tccccccaaa acccaaggac accctcatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgggtgg tcagcgtcct caccgtcctg caccaggact ggctgaatgg caaggagtac    780
aagtgcaagg tctccaacaa agccctccca gcccccatcg agaaaaccat ctccaaagcc    840
aaagggcagc cccgagaacc acaggtgtac accctgcccc catcccggga tgagctgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaatgagtc gac                                1173
```

<210> SEQ ID NO 4
<211> LENGTH: 388
<212> TYPE: PRT
<213> ORGANISM: Homo sapiens

<400> SEQUENCE: 4

```
Met Ala Ser Leu Ser Arg Pro Ser Leu Pro Ser Cys Leu Cys Ser Phe
  1               5                  10                  15

Leu Leu Leu Leu Leu Leu Gln Val Ser Ser Tyr Ala Gly Gln Phe
                 20                  25                  30

Arg Val Ile Gly Pro Arg His Pro Ile Arg Ala Leu Val Gly Asp Glu
             35                  40                  45

Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Ser Gly Glu Pro Lys Ser
145                 150                 155                 160

Cys Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220
```

-continued

```
Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
            245                 250                 255

Gly Lys Glu Tyr Lys Cys Lys Val Ser Asn Lys Ala Leu Pro Ala Pro
        260                 265                 270

Ile Glu Lys Thr Ile Ser Lys Ala Lys Gly Gln Pro Arg Glu Pro Gln
    275                 280                 285

Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
tagaattcat ggcaagctta tcgagaccc                                    29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 6
catccggatc cagggctcac ccagtaga                                     28

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
tatccggaga gcccacctct tgtgacaaaa c                                 31

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 8
```

-continued

```
gtgtcgactc atttacccgg agacaggg                                    28

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9
tatccggaga gcccaaatct tgtgacaaaa c                                31
```